(12) United States Patent
Kolaczkowski et al.

(10) Patent No.: US 12,319,682 B2
(45) Date of Patent: Jun. 3, 2025

(54) INDOLE AND BENZIMIDAZOLE DERIVATIVES AS DUAL 5-HT$_{2A}$ AND 5-HT$_6$ RECEPTOR ANTAGONISTS

(71) Applicant: Adamed Pharma S.A, Czosnow (PL)

(72) Inventors: Marcin Kolaczkowski, Wieliczka (PL); Adam Bucki, Przebieczany (PL); Joanna Sniecikowska, Wieliczka (PL); Monika Marcinkowska, Cracow (PL)

(73) Assignee: ADAMED PHARMA S.A., Czosnow (PL)

( * ) Notice: Subject to any disclaimer, the term of this patent is extended or adjusted under 35 U.S.C. 154(b) by 0 days.

(21) Appl. No.: 18/637,083

(22) Filed: Apr. 16, 2024

(65) Prior Publication Data

US 2024/0287056 A1    Aug. 29, 2024

Related U.S. Application Data

(63) Continuation of application No. 17/326,159, filed on May 20, 2021, now Pat. No. 11,981,668, which is a continuation of application No. 16/970,871, filed as application No. PCT/EP2019/054171 on Feb. 20, 2019, now Pat. No. 11,034,688.

(30) Foreign Application Priority Data

Feb. 21, 2018    (EP) .................................... 18461519

(51) Int. Cl.
| | | |
|---|---|---|
| C07D 417/14 | (2006.01) | |
| A61P 25/28 | (2006.01) | |
| C07D 403/10 | (2006.01) | |
| C07D 405/14 | (2006.01) | |
| C07D 409/14 | (2006.01) | |

(52) U.S. Cl.
CPC ............ *C07D 417/14* (2013.01); *A61P 25/28* (2018.01); *C07D 403/10* (2013.01); *C07D 405/14* (2013.01); *C07D 409/14* (2013.01)

(58) Field of Classification Search
None
See application file for complete search history.

(56) References Cited

U.S. PATENT DOCUMENTS

| 11,034,688 B2 | 6/2021 | Kolaczkowski et al. |
| 11,981,668 B2 * | 5/2024 | Kolaczkowski ........ A61P 25/18 |
| 2020/0377496 A1 | 12/2020 | Kolaczkowski et al. |
| 2021/0276995 A1 | 9/2021 | Kolaczkowski et al. |

FOREIGN PATENT DOCUMENTS

| WO | WO 2007/006677 A1 | 1/2007 |
| WO | WO 2008/055808 A1 | 5/2008 |
| WO | WO 2010/056644 A1 | 5/2010 |
| WO | WO 2013/001499 A1 | 1/2013 |

OTHER PUBLICATIONS

U.S. Appl. No. 17/326,159, filed May 20, 2021, Adamed Pharma S.A.
International Search Report issued Aug. 4, 2019 in connection with PCT International Application No. PCT/EP2019/054171.
Written Opinion (form PCT/ISA/237) issued Aug. 4, 2019 in connection with PCT International Application No. PCT/EP2019/054171.
Nov. 23, 2020 Non-Final Office Action issued in connection with U.S. Application No. 16/970, 871.
Jan. 25, 2021 Amendment in response to Nov. 23, 2020 Office Action issued in connection with U.S. Appl. No. 16/970,871.
Feb. 8, 2021 Notice of Allowance issued in connection with U.S. Appl. No. 16/970,871.
De La Fuente, T. et al. "Benzimidazole Derivatives as New Serotonin 5-HT6 Receptor Antagonists. Molecular Mechanisms of Receptor Inactivation," Journal of Medicinal Chemistry, vol. 53, No. 3, 2010, pp. 1357-1369.
Slassi, A. et al. "Recent progress in the 5-HT6 receptor antagonists for the treatment of CNS diseases," Expert Opinion on Therapeutic Patents, vol. 12, No. 4, 2002, pp. 513-527.

* cited by examiner

*Primary Examiner* — Brian J Davis
(74) *Attorney, Agent, or Firm* — Gary J. Gershik

(57) ABSTRACT

The invention relates to new 4-(piperazin-1-yl)-2-(trifluoromethyl)-1H-indoles and 4-(piperazin-1-yl)-2-(trifluoromethyl)-1H-benzimidazoles represented by formula (I), wherein all symbols and variables are as defined in the description. The compounds can find use in a method of prevention and/or treatment of diseases selected from the group consisting of Alzheimer's disease, Parkinson's disease, Levy body dementia, dementia-related psychosis, schizophrenia, delusional syndromes and other psychotic conditions related and not related to taking psychoactive substances, depression, anxiety disorders of various aetiology, sleep disorders of various aetiology.

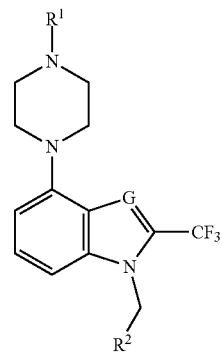

20 Claims, No Drawings

INDOLE AND BENZIMIDAZOLE DERIVATIVES AS DUAL 5-HT$_{2A}$ AND 5-HT$_6$ RECEPTOR ANTAGONISTS

This Application is a continuation of U.S. application Ser. No. 17/326,159, filed May 20, 2021, which is a continuation of U.S. application Ser. No. 16/970,871, filed Aug. 18, 2020, now U.S. Pat. No. 11,034,688, issued Jun. 15, 2021, which is a § 371 national stage of PCT International Application No. PCT/EP2019/054171, filed Feb. 20, 2019, claiming priority of European Patent Application No. 18461519.3, filed Feb. 21, 2018, the contents of each of which are hereby incorporated by reference herein.

The present invention relates to new 4-(piperazin-1-yl)-2-(trifluoromethyl)-1H-indoles and 4-(piperazin-1-yl)-2-(trifluoromethyl)-1H-benzimidazoles. The present invention relates also to pharmaceutical compositions comprising the compounds, and these compounds and the pharmaceutical composition for use as a medicament.

Dementia is a set of progressive deterioration of cognitive functions associated with behavioral and psychological disorders and difficulties in everyday functioning (Hersch and Falzgraf, 2007). The most important category of brain damaging factors to such an extent that the symptoms of dementia occur, are neurodegenerative diseases, leading to the progressive degeneration of nervous tissue. The ICD-10 classification distinguishes, inter alia, dementia of the Alzheimer type (DAT), as well as dementia in Pick's disease (frontotemporal), dementia in Huntington's disease, dementia in Parkinson's disease and very similar dementia with Lewy bodies. The reason of brain damage leading to dementia can be infectious diseases such as Creutzfeldt-Jakob disease (included concurrently to neurodegenerative diseases), HIV/AIDS infection or neuroborreliosis. Beside neurodegenerative and infectious diseases, the symptoms of dementia can also be related to vascular diseases such as stroke, which can cause so called acute onset of dementia or vascular dementia (after a series of strokes). In the elderly, the most common cause of dementia is Alzheimer's disease. Global prevalence of dementia is estimated to be about 3.9% of the population aged over 60 years (Ferri et al., 2005), which means that currently there are about 35.6 million people with different forms of dementia in the world. In light of the anticipated increase in life expectancy, this number will double by 2030, and triple by 2050. Dementia is therefore a very serious and growing medical and social problem.

In addition to the axial cognitive disorders, up to 60% of patients with dementia also experience so called behavioral and psychological symptoms of dementia (BPSD). The following can be distinguished among them: psychotic disorders (delusions and hallucinations), depression, apathy, sexual disinhibition, irritability, verbal and physical aggression, psychomotor agitation and anxiety (Carson et al., 2006; Jeste et al., 2008).

For example, from 40 to 60% of patients with dementia experience considerable depressive disorders at some stage of the disease (Hersch and Falzgraf, 2007), while the prevalence of psychotic symptoms can reach 63% of the patients in case of delusions, and 41% in case of hallucinations (Jeste et al., 2008). BPSD may occur at any stage of the disease, some symptoms are more common in mild dementia (depression, apathy, anxiety, irritability), while others are more common in the advanced stages of dementia (delusions, hallucinations, disinhibition) (Hersch and Falzgraf, 2007). It has been demonstrated many times that just BPSD are the major burden both for the patients with dementia and their carers, and may be experienced even more acutely than basic cognitive impairment. The occurrence of BPSD is also associated with poor prognosis of disease progresses, more rapid loss of cognitive function and specific impairment of everyday life. Psychosis, agitation, aggression, and depression accompanying dementia are the leading predictors of institutionalization of the patient, and are the main goals in the treatment of BPSD from clinical and social perspectives (Amano et al., 2009; Gauthier et al., 2010; Hersch and Falzgraf, 2007).

Until the mid-1990s, the drugs of choice in the treatment of BPSD were first-generation antipsychotics (i.e. typical neuroleptics), especially in the case of delusions and hallucinations. It was demonstrated that the main representative of this class of drugs, haloperidol, does not affect the excitation or behavioral symptoms as a whole, it reduces aggression. At the same time, a meta-analysis of clinical trials demonstrated lack of differences between first-generation antipsychotics in their efficacy to BPSD (Sink et al., 2005). In following years, the typical neuroleptics were partially replaced in BPSD treatment with antipsychotic second-generation drugs (i.e. atypical neuroleptics)(De Deyn et al., 2005), which are characterized by lower tendency for extrapyramidal disorders inducing (extrapyramidal symptoms—EPS), and higher efficiency as compared to first generation drugs (Liperoti et al., 2008). However, the effectiveness and safety of drugs currently used in BPSD treatment are not satisfactory (Nobili et al., 2009). The review of 16 clinical trials with second-generation antipsychotics application in the treatment of BPSD, performed within an activity of the Cochrane (Cochrane Library) revealed that risperidone and olanzapine were effective in the treatment of aggression, and risperidone was also more effective than placebo in the treatment of psychosis associated with dementia (Ballard and Waite, 2006). However, both drugs caused significant side effects of extrapyramidal disorders and cardiovascular events character. Meanwhile, aripiprazole showed no advantage over placebo in the treatment of delusions and hallucinations in patients with Alzheimer's disease related psychosis (De Deyn et al., 2005). The use of antipsychotics in the treatment of BPSD is additionally complicated by the fact that these drugs exacerbate existing cognitive impairments, which is particularly disadvantageous in patients with dementia (Fasano et al., 2012; Jeste et al., 2008; Vigen et al., 2011).

In light of these facts, since 2005, the US Food and Drug Administration Agency (FDA) require special warnings placing on the leaflets of the second-generation antipsychotics. These warnings (so called "boxed warnings") are associated with an occurrence of serious side effects and increased risk of death, in case of the use of atypical neuroleptics in patients with dementia (U.S. Food and Drug Administration, 2005). Since 2008, the requirement of similar warnings has been also applied in case of the first-generation antipsychotics (U.S. Food and Drug Administration, 2008).

Despite this, antipsychotics are still widely used in patients with BPSD (Schneider et al., 2006; Schulze et al., 2013b), mainly because there is no more favorable alternative (Schulze et al., 2013a). Currently, there are no drugs approved for the treatment of psychosis associated with dementia, as well as no antidepressants, anxiolytics, antiaggressive drugs, designed specifically to meet the therapeutic needs of the elderly.

Psychosis in dementia may have a different neurobiological substrate from that in schizophrenia. Indeed, psychotic Alzheimer patients often experience visual hallucinations and misidentifications of caregivers—symptoms that are not commonly found in schizophrenia patients. Conversely, bizarre or complex delusions that occur frequently in patients with schizophrenia are not often observed in dementia patients (Jeste and Finkel, 2000). The distinct nature of psychotic symptoms in dementia suggests that different neurotransmitter systems are at play. In particular, serotonergic systems may be involved because hallucinations in dementia are similar to those caused by serotonergic agonists such as mescaline or lysergic acid (Marsh, 1979). Strong visual hallucinations can be also evoked by NMDA receptor antagonists such as ketamine or phencyclidine (Siegel, 1978) but are less frequently evoked by dopaminomimetics such as amphetamine or cocaine, which are widely used in preclinical screening of new drugs for schizophrenia (Jones et al., 2011).

There are substantial data supporting the importance of the serotonin system in the development of BPSD. For example, serotonin receptor gene polymorphisms are associated with visual and auditory hallucinations in patients with Alzheimer's disease (AD) (Holmes et al., 1998). A genetic polymorphism of the serotonin transporter promoter region (L/L genotype) has been associated with aggressive behaviour (Sukonick et al., 2001). Other studies show involvement of $5HT_{2A}$ and $5HT_6$ receptors in the pathogenesis of AD (Lorke et al., 2006) as well as association of $5-HT_6$ receptors with psychotic symptoms in patients with AD (Marcos et al., 2008).

It has been observed that hallucinations, mainly visual, caused by psychotomimetic substances, such as LSD (D-lysergic acid diethylamide) or DOI (2,5-Dimethoxy-4-iodoamphetamine), are associated with activation of the $5-HT_{2A}$ receptors in the cerebral cortex (Nichols, 2004). Taking into account their clinical hallucinogenic similarity to those observed in dementia patients, the involvement of common pharmacological mechanisms, including serotoninergic dysregulation, has been suggested. The involvement of the blockade of $5-HT_{2A}$ serotonin receptors in antipsychotic activity was further confirmed by the activity of the $5-HT_{2A}$ receptor antagonists in glutamatergic models of psychosis, associated with facilitation of glutamatergic transmission in cerebral cortex (Varty et al., 1999). Consistent with the above is the fact, that pimavanserin, a selective inverse agonist of $5-HT_{2A}$ receptor, is the first antipsychotic drug that has been approved in 2016 for the treatment of Parkinson's disease psychosis. It is important to note, however, that pimavanserin has a significant affinity for hERG channels (about 210 nM), which may cause changes in ECG, potentially leading to life-threatening arrhythmias. Moreover, pimavanserin has no affinity for the $5-HT_6$ receptors.

Converging lines of evidence indicate that blockade of serotonin $5 HT_6$ receptors ($5 HT_6Rs$) may be implicated in: (i) pro-cognitive effects due to facilitation of cholinergic transmission (Liu and Robichaud, 2009; Riemer et al., 2003), (ii) antidepressant activity due to the increase in noradrenergic and dopaminergic tone, as well as (iii) an anxiolytic effect, mediated by interaction with GABA-ergic transmission (Wesolowska, 2010; Wesolowska and Nikiforuk, 2007). Those findings are further supported by the exclusive localization of $5-HT_6$ receptors in the central nervous system (CNS), especially in limbic and cortical brain areas involved in the control of mood and cognition (Woolley et al., 2004).

The cholinomimetic component of the $5-HT_6$ receptors blockade, in addition to its significance for procognitive activity, also appears to be significant from the point of view of potentially beneficial antipsychotic effects. Indeed, it has been shown that muscarinic receptor antagonists have antipsychotic properties (Maehara et al., 2008). Thus, although selective blockade of the $5-HT_6$ receptor does not induce antipsychotic activity alone, it may contribute to its augmentation. In line with the above, recent studies showed, that a combination of the $5-HT_{2A}$ and $5-HT_6$ receptor antagonism may produce a stronger antipsychotic effect than the independent use of a selective antagonist of each of those receptors (Fijał et al., 2014).

Increased therapeutic efficacy of dual $5-HT_{2A}$ and $5-HT_6$ receptor antagonists in patients with dementia may be due not only to augmented antipsychotic activity resulting from synergistic modulation of glutamatergic and cholinergic transmission, but also due to the $5-HT_6$ receptor blockade-mediated procognitive activity, mostly of cholinomimetic nature. These properties are crucial because the presence of psychosis in dementia is inextricably linked to cognitive impairment (Murray et al., 2014).

Therefore, dual antagonist of $5-HT_{2A}$ and $5-HT_6$ receptors, which joins both antipsychotic and procognitive activity in one molecule, addresses the most important therapeutic challenges in dementia-related psychosis.

International Application WO2007/006677 discloses certain benzimidazolone and hydroindolone derivatives as selective $5-HT_6$ antagonists, selective $5-HT_{2A}$ antagonists, or both. The description does not precise which compounds are dual antagonist of $5-HT_{2A}$ and $5-HT_6$ receptors, however in his reply to the Written Opinion, Applicant disclosed activities for four compounds for both receptors. Nonetheless, all compound disclosed having 4-piperazine substituted benzimidazolone derivatives have unsubstituted piperazine nitrogen as hydrogen bond donor. Furthermore, presence of carbonyl group in the position 2 adversely affects metabolic and chemical stability of such compounds, and in case of benzimidazole compounds there is a possibility of lactam-lactim tautomer formation that is unfavorable because of additional ionisation in certain pH ranges, and formation of additional hydrogen bond donor site. All this negatively affects penetration through biological membranes, and therefore hinders absorption from the gastrointestinal tract and penetration of the brain-blood barrier.

International Application WO2008/055808 discloses certain compounds as selective $5-HT_6$ antagonists, selective $5-HT_{2A}$ antagonists, or both. Compounds disclosed in this international application have optionally substituted amide group in the position 2.

The compounds have a low metabolic and chemical stability due to hydrolysis of the amide group to carboxylate. Furthermore, presence of the amide group does not allow to obtain compounds with a dual affinity, i.e. not only to $5-HT_6$, but also to $5-HT_{2A}$.

International Applications WO2010/056644 and WO2013/001499 disclose compounds having substitution in the position 2 with alkyl group or no substitution at all, i.e. there is hydrogen atom in the position 2. Again, compounds with a dual affinity, i.e. not only to $5-HT_6$, but also to $5-HT_{2A}$ cannot be obtained.

So far, there has been no compound identified that would be a potential drug joining antipsychotic and procognitive activity in one molecule, acting by antagonism of $5-HT_{2A}$ and $5-HT_6$ receptors, and, on the other hand, having favourable properties as to, for example, bioavailability, and ease of penetration of blood-brain barrier.

Thus, there is still a need in the art for such compounds.

Therefore, the present inventions provides new compounds with 4-(piperazin-1-yl)-2-(trifluoromethyl)-1H-indole or 4-(piperazin-1-yl)-2-(trifluoromethyl)-1H-benzimidazole core as dual antagonist of 5-HT$_{2A}$ and 5-HT$_6$ receptors having favourable both in vitro and in vivo characteristics, and therefore being promising candidates in clinical trials In first aspect, the present invention relates to a compound of general formula (I):

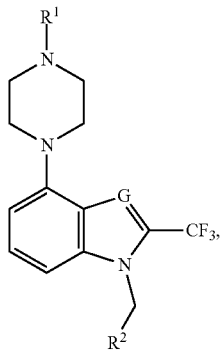

Formula (I)

wherein:
G is CH or N;
R$^1$ is H, C$_1$-C$_4$-alkyl, HO—C$_1$-C$_4$-alkyl or C$_1$-C$_4$-alkyl-O—C$_1$-C$_4$-alkyl;
R$^2$ is selected from group consisting of:
  phenyl group unsubstituted or substituted with at least one substituent, or
  5- or 6-membered heteroaryl group unsubstituted or substituted with at least one substituent,
    wherein the substituent is selected from F, Cl, Br, C$_1$-C$_4$-alkyl-', C$_1$-C$_4$-alkyl-O—, In first embodiment, in compounds of formula (I), G is CH.

In alternative embodiment, in compounds of formula (I), G is N.

Preferably, in compounds of formula (I), R$^1$ is H, methyl, or 2-hydroxyethyl.

In one preferable embodiment of compounds of formula (I), R$^2$ is selected from phenyl group unsubstituted or substituted with at least one substituent.

In another preferable embodiment of compounds of formula (I), R$^2$ is selected from 5- or 6-membered heteroaryl group unsubstituted or substituted with at least one substituent. In this preferable embodiment, preferably, 5- or 6-membered heteroaryl is selected from furyl, thienyl, thiazolyl, or pyridyl.

In yet another, the most preferable embodiment,
R$^2$ is selected from group consisting of:
  phenyl group unsubstituted or substituted with at least one substituent, or
  5- or 6-membered heteroaryl group unsubstituted or substituted with at least one substituent,
    wherein 5- or 6-membered heteroaryl is selected from furyl, thienyl, thiazolyl, or pyridyl
      wherein the substituent is selected from F, Cl, Br, C$_1$-C$_4$-alkyl-, C$_1$-C$_4$-alkyl-O—, In all embodiments, when R$^2$ is a substituted group, it is substituted with one or two substituents. More preferably, it is substituted with one substituent.

Preferably, in definitions of R$^2$ group, the substituent is selected from F, Cl, methyl or methoxy.

Alternatively, it is also preferable, when R$^2$ group is unsubstituted.

The following specific compounds of formula (I) of the invention can be mentioned:
1-benzyl-4-(piperazin-1-yl)-2-(trifluoromethyl)-1H-benzimidazole,
1-benzyl-4-(4-methylpiperazin-1-yl)-2-(trifluoromethyl)-1H-benzimidazole,
2-{4-[1-benzyl-2-(trifluoromethyl)-1H-benzimidazol-4-yl]piperazin-1-yl}ethanol,
1-(furan-2-ylmethyl)-4-(piperazin-1-yl)-2-(trifluoromethyl)-1H-benzimidazole,
1-[(5-methylfuran-2-yl)methyl]-4-(piperazin-1-yl)-2-(trifluoromethyl)-1H-benzimidazole,
1-(3-chlorobenzyl)-4-(piperazin-1-yl)-2-(trifluoromethyl)-1H-benzimidazole,
1-(3-fluorobenzyl)-4-(piperazin-1-yl)-2-(trifluoromethyl)-1H-benzimidazole,
1-(3,4-dichlorobenzyl)-4-(piperazin-1-yl)-2-(trifluoromethyl)-1H-benzo[d]imidazole,
1-(3-chloro-4-fluorobenzyl)-4-(piperazin-1-yl)-2-(trifluoromethyl)-1H-benzo[d]imidazole,
1-(3,4-difluorobenzyl)-4-(piperazin-1-yl)-2-(trifluoromethyl)-1H-benzo[d]imidazole,
1-(3,5-dichlorobenzyl)-4-(piperazin-1-yl)-2-(trifluoromethyl)-1H-benzo[d]imidazole,
1-benzyl-4-(piperazin-1-yl)-2-(trifluoromethyl)-1H-indole,
1-(3,4-dichlorobenzyl)-4-(4-methylpiperazin-1-yl)-2-(trifluoromethyl)-1H-indole,
1-(4-chloro-3-fluorobenzyl)-4-(4-methylpiperazin-1-yl)-2-(trifluoromethyl)-1H-indole,
4-(piperazin-1-yl)-1-(1,3-thiazol-2-ylmethyl)-2-(trifluoromethyl)-1H-indole,
1-(4-chloro-3-fluorobenzyl)-4-(piperazin-1-yl)-2-(trifluoromethyl)-1H-indole,
1-(furan-2-ylmethyl)-4-(piperazin-1-yl)-2-(trifluoromethyl)-1H-indole,
1-(3-methoxybenzyl)-4-(4-methylpiperazin-1-yl)-2-(trifluoromethyl)-1H-indole,
1-(3-fluorobenzyl)-4-(piperazin-1-yl)-2-(trifluoromethyl)-1H-indole,
1-(3-chlorobenzyl)-4-(piperazin-1-yl)-2-(trifluoromethyl)-1H-indole,
1-(furan-2-ylmethyl)-4-(4-methylpiperazin-1-yl)-2-(trifluoromethyl)-1H-indole,
1-(3,4-difluorobenzyl)-4-(4-methylpiperazin-1-yl)-2-(trifluoromethyl)-1H-indole,
1-(3-methoxybenzyl)-4-(piperazin-1-yl)-2-(trifluoromethyl)-1H-indole,
1-(3-fluorobenzyl)-4-(4-methylpiperazin-1-yl)-2-(trifluoromethyl)-1H-indole,
1-(3,4-difluorobenzyl)-4-(piperazin-1-yl)-2-(trifluoromethyl)-1H-indole,
1-benzyl-4-(4-methylpiperazin-1-yl)-2-(trifluoromethyl)-1H-indole,
1-(3-chlorobenzyl)-4-(4-methylpiperazin-1-yl)-2-(trifluoromethyl)-1H-indole,
1-[(5-methylfuran-2-yl)methyl]-4-(piperazin-1-yl)-2-(trifluoromethyl)-1H-indole,
1-[(5-methylthiophen-2-yl)methyl]-4-(piperazin-1-yl)-2-(trifluoromethyl)-1H-indole,
4-(piperazin-1-yl)-1-(thiophen-2-ylmethyl)-2-(trifluoromethyl)-1H-indole,
4-(piperazin-1-yl)-1-(thiophen-3-ylmethyl)-2-(trifluoromethyl)-1H-indole,
4-(4-methylpiperazin-1-yl)-1-(thiophen-3-ylmethyl)-2-(trifluoromethyl)-1H-indole,
4-(4-methylpiperazin-1-yl)-1-(thiophen-2-ylmethyl)-2-(trifluoromethyl)-1H-indole,
4-(4-methylpiperazin-1-yl)-1-[(5-methyl-1,3-thiazol-2-yl)methyl]-2-(trifluoromethyl)-1H-indole.

In one especially preferable embodiment,
G is N, R² is unsubstituted phenyl group, and R¹ is H, and the compound is

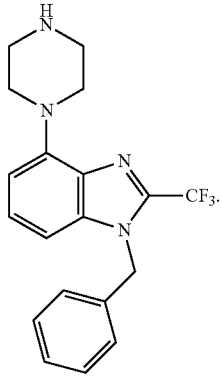 [SMILES: FC(F)(F)c1nc2c(N3CCNCC3)cccc2n1Cc1ccccc1]

In one another especially preferable embodiment,
G is CH, R² is unsubstituted 2-furyl group, and R¹ is H, and the compound is

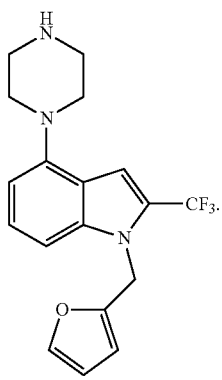 [SMILES: FC(F)(F)c1cc2c(N3CCNCC3)cccc2n1Cc1ccco1]

In one another especially preferable embodiment,
G is CH, R² is unsubstituted 2-furyl group, and R¹ is —CH₃,
and the compound is

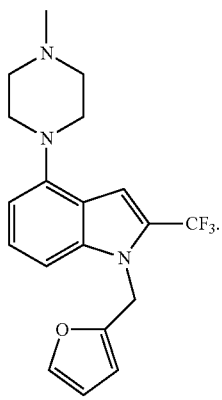 [SMILES: CN1CCN(c2cccc3c2cc(C(F)(F)F)n3Cc2ccco2)CC1]

And, in one another especially preferable embodiment,
G is CH, R² is 5-methyl-2-furyl group, and R¹ is H, and the compound is

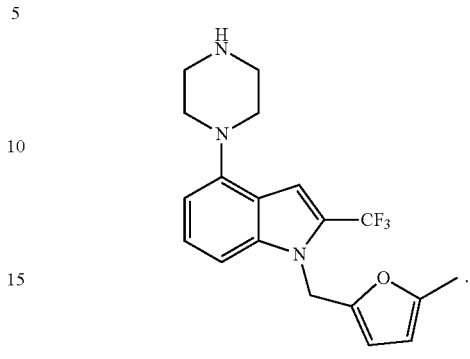

The mechanism of action of the compounds of invention is based on the selective blockade of both 5-HT$_{2A}$ and 5-HT$_6$ serotonin receptors which role in the pathomechanism and pharmacotherapy of psychotic and cognitive disorders has been well confirmed in both preclinical and clinical studies.

Therefore, the compounds of the invention may be useful in medicine as medicaments for treatment and/or prevention of conditions sensitive to control of serotonin system, especially the antagonism of 5-HT$_{2A}$ and 5-HT$_6$ receptors, such as: cognitive disorders of various types, e.g. Alzheimer's disease, Parkinson's disease, Levy body dementia, dementia-related psychosis, schizophrenia, schizoaffective disorders, schizophreniform disorders, delusional syndromes and other psychotic conditions related and not related to taking psychoactive substances, affective disorder, bipolar disorder, mania, depression, anxiety disorders of various aetiology, stress reactions, consciousness disorders, coma, alcoholic delirium and of various aetiology, aggression, psychomotor agitation, and other conduct disorders, sleep disorders of various aetiology, withdrawal syndromes of various aetiology, addiction, pain syndromes of various aetiology, intoxication with psychoactive substances, cerebral circulatory disorders of various aetiology, psychosomatic disorders of various aetiology, conversion disorders, dissociative disorders, urinary disorders, autism and other developmental disorders e.g. nocturia, stuttering, tics, psychopathological symptoms and neurological disorders in course of other diseases of the central and peripheral nervous systems are understood.

Thus, in the second aspect, the invention relates to the compound of the present invention for use as a medicament.

Preferably, the compound of the present invention can be used in treatment of cognitive disorders of various types, i.a. Alzheimer's disease, Parkinson's disease, Levy body dementia, dementia-related psychosis, schizophrenia, delusional syndromes and other psychotic conditions related and not related to taking psychoactive substances, depression, anxiety disorders of various aetiology, sleep disorders of various aetiology.

In the treatment of central nervous system disorders compounds of formula (I) may be administered in the form of a pharmaceutical composition or formulation containing it.

Therefore, in the third aspect, the invention relates to a pharmaceutical composition comprising a compound of formula (I) or a salt thereof and at least one pharmaceutically acceptable excipient.

DETAILED DESCRIPTION

The terms used in the present invention have the following meanings. Other terms not defined below have the meanings as those understood by those skilled in the art.

The term "$C_1$-$C_4$-alkyl" is a saturated, straight or branched chain hydrocarbon having 1 to 4 carbon atoms. Examples of $C_1$-$C_4$-alkyl are methyl, ethyl, n-propyl, isopropyl, n-butyl, tert-butyl, sec-butyl. More preferably, $C_1$-$C_4$-alkyl is a $C_1$-$C_3$-alkyl, $C_1$-$C_2$-alkyl, or $C_1$-alkyl. Notation $C_1$-$C_3$-alkyl, $C_1$-$C_2$-alkyl means a saturated, straight or branched chain hydrocarbon having 1 to 3 or 2 carbon atoms, respectively. Most preferably, the $C_1$-$C_4$-alkyl is $C_1$-$C_2$alkyl that is methyl group (abbreviated as $CH_3$) or ethyl group.

The term "5- or 6-membered heteroaryl group" is a monocyclic aromatic ring group having 1 to 4 hetero atoms selected from nitrogen, sulfur and oxygen atoms and include, for example, a furyl group, a thienyl group, a pyrrolyl group, an imidazolyl group, a pyrazolyl group, a thiazolyl group, an isothiazolyl group, an oxazolyl group, an isoxazolyl group, a triazolyl group, an oxadiazolyl group, a thiadiazolyl group, a tetrazolyl group, a pyridyl group, a pyrimidyl group, a pyridazinyl group and a pyrazinyl group. Preferably, the 5- or 6-membered heteroaryl group is selected form a furyl group, a thienyl group, a a triazolyl group, or a pyridyl group.

Since the compounds of the invention are basic they can form suitable acid addition salts.

Pharmaceutically acceptable acid addition salt refers to those salts which retain the biological effectiveness of the free bases and which are not biologically undesirable. Acid addition salts may be formed with inorganic (mineral) acids or organic acids. As examples of acids, may be mentioned hydrochloric, hydrobromic, hydroiodic, phosphoric, sulfuric, nitric, carbonic, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, pamoic, xinafoic, hexanoic acid.

Compounds of Formula (I) can be Obtained Using the Following Methods

Compounds of formula (I), when G is N, i.e. compounds based on 4-(piperazin-1-yl)-2-(trifluoromethyl)-1H-benzimidazole core may be obtained according to the following Reaction Scheme 1.

Reaction Scheme 1.

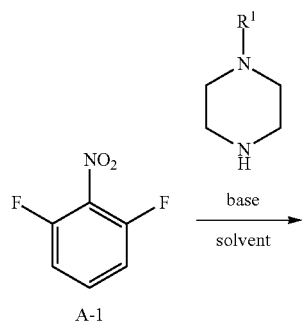

A-1

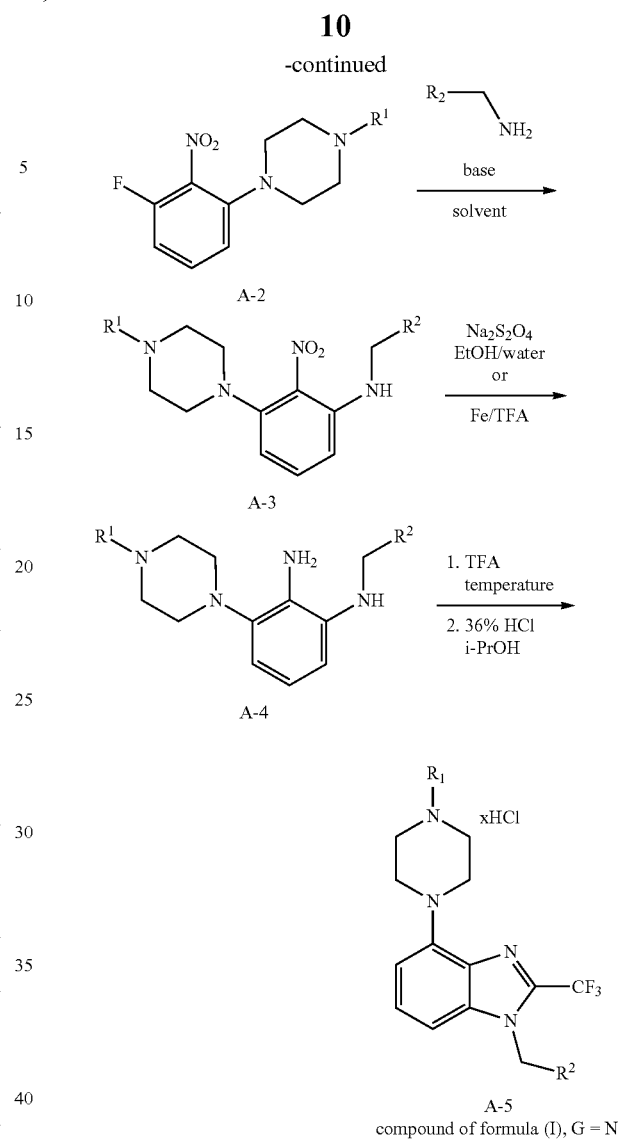

Initially, 2,6-difluoronitrobenzene A-1 was treated with piperazine derivative ($R^1$=Me, BOC) in the presence of a base (typically $K_2CO_3$). The resulting product A-2 was reacted subsequently with benzylamine ($R^2$=aryl, heteroaryl) in the presence of the base (typically $K_2CO_3$), providing compound A-3. Next, bisaniline A-4 was prepared by a reduction of the nitro group in A-3 with either sodium dithionite at elevated temperature or metallic iron. Finally, reaction of the bisaniline A-4 with TFA and subsequent HCl salt formation gave expected benzimidazoles A-5.

Reaction Scheme 2

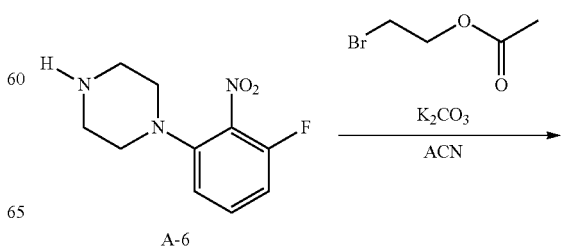

A-6

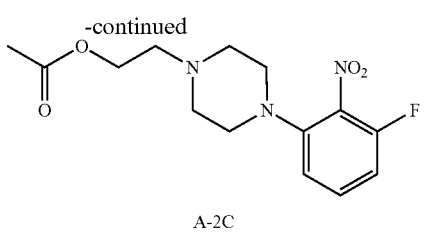

A-2C

Reaction Scheme 2 illustrates a representative example when 1-(3-fluoro-2-nitrophenyl)piperazine A-6 was reacted with 2-bromoethyl acetate in the presence of $K_2CO_3$ to obtain the piperazine derivative A-2C.

36% solution of HCl followed by basification, resulting desired benzimidazoles A-5, compound of formula (I) wherein G=N.

Alternatively, compounds of formula (I), when G is CH, i.e. compounds based on 4-(piperazin-1-yl)-2-(trifluoromethyl)-1H-benzimidazole core may be obtained according to the following Reaction Scheme 4.

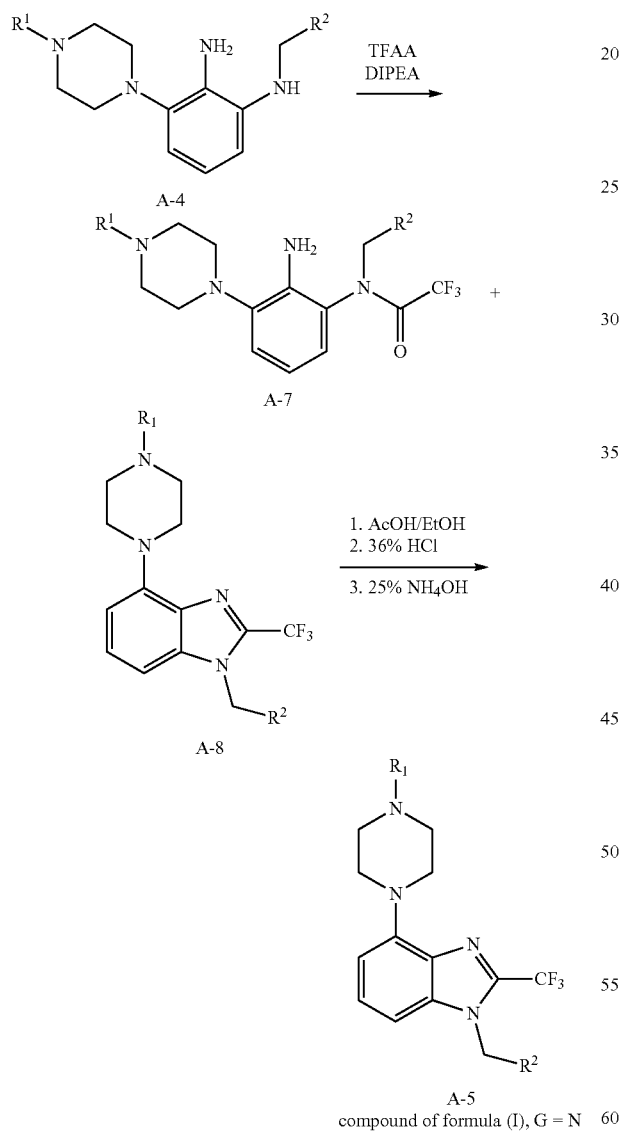

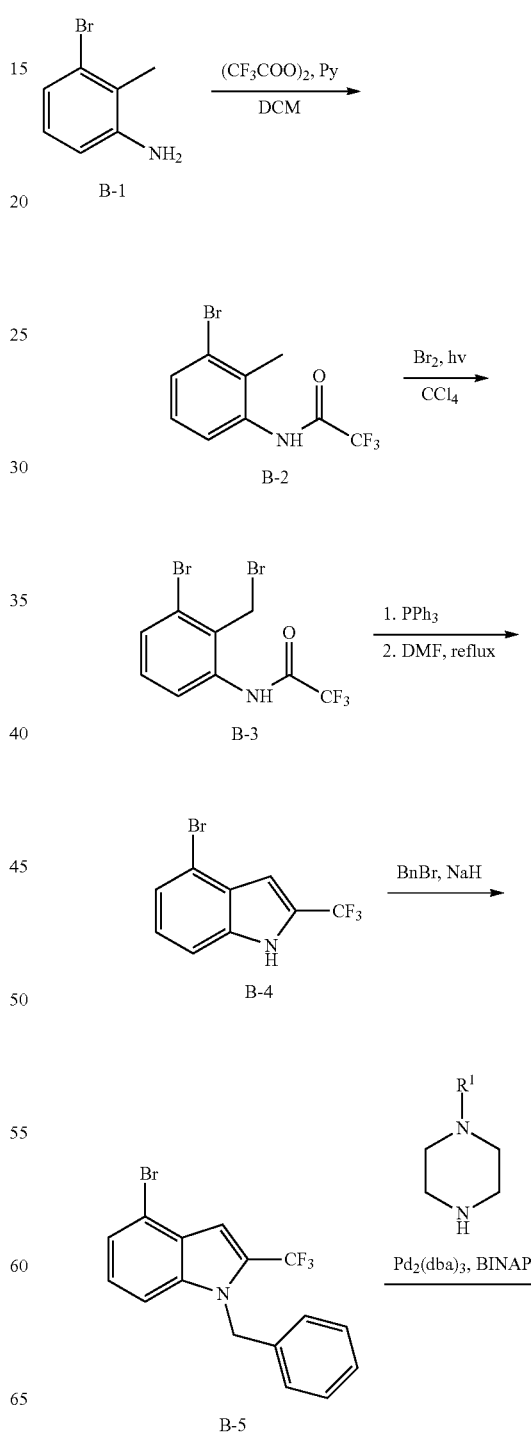

Reaction Scheme 3 illustrates examples when $R^2$=2-furyl or 5-methyl-2-furyl. In this case bisaniline A-4 was reacted with TFAA to give a mixture of compounds A-7 and A-8. Compound A-7 was quantitatively converted to A-8 using AcOH and such obtained compound A-8 was treated with -continued

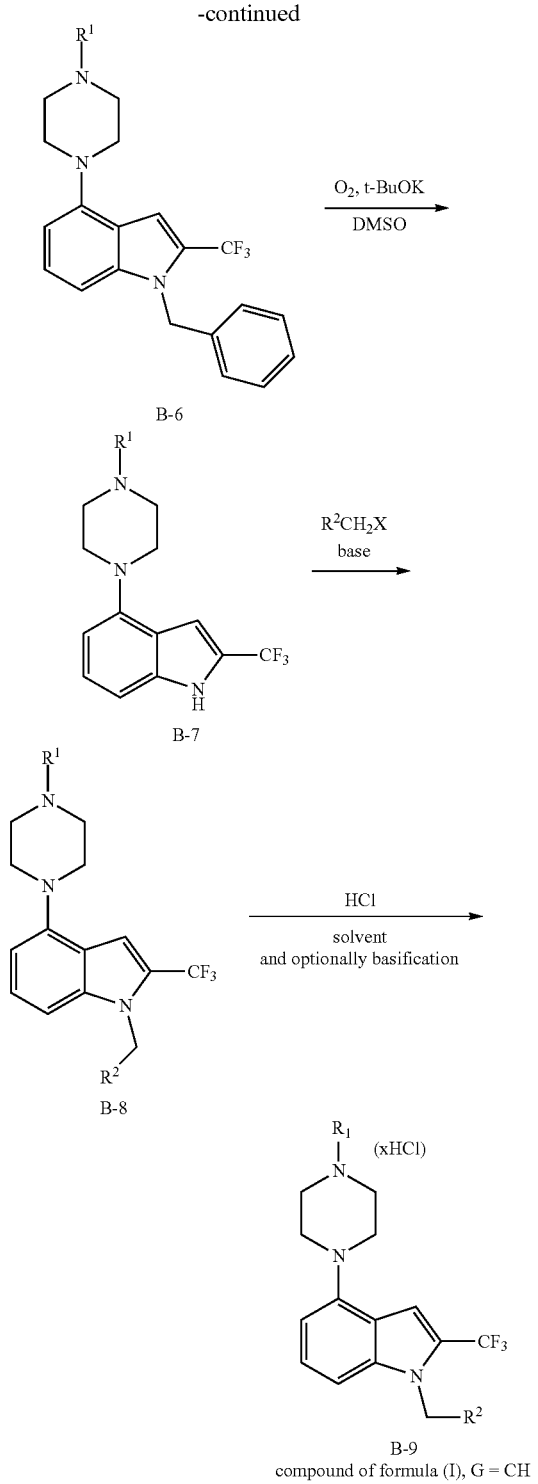

afforded building block B-7. Finally, reaction of the indole B-7 with benzyl bromide ($R^2$=aryl, heteroaryl) and in some cases subsequent HCl salt formation gave final trifluoroindoles B-9, compound of formula (I) wherein G=CH. Optionally, the HCl salts of the trifluoroindoles B-9 can be basified and transformed in other pharmaceutically acceptable salt or used as a free base.

Reaction Scheme 6.

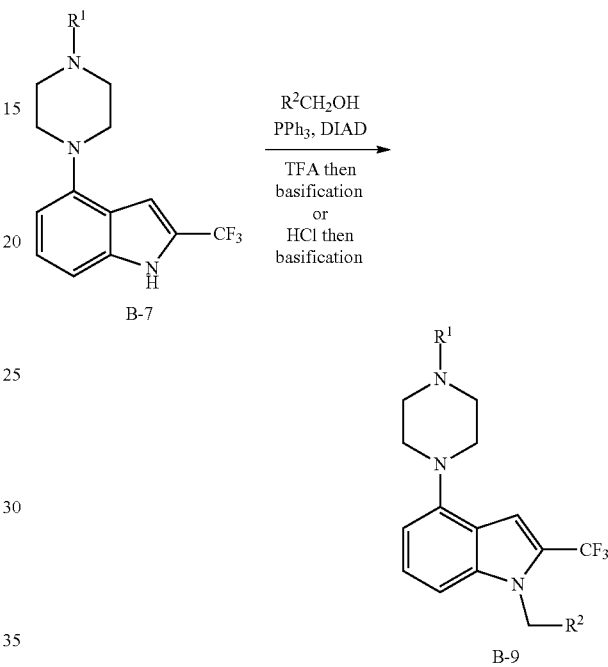

Reaction scheme 6 illustrates an alternative approach to compounds B-9 using Mitsunobu reaction conditions. Indole B-7 was reacted with proper benzyl alcohol in the presence of triphenylphosphine and diisopropylazadicarboxylate. Product B-8 of the reaction was treated with TFA or HCl in the chosen solvent followed by basification to produce compound B-9 as a free base.

An acid addition salt may be prepared in a simple manner by reacting a compound of formula (I) in a free base form with a suitable inorganic or organic acid in an amount substantially equimolar to the compound of formula (I), optionally in a suitable solvent such as an organic solvent to form a salt which is usually isolated for example by crystallization and filtration.

For example, a free base of a compound of formula (I) can be converted into corresponding hydrochloride salt by treating a solution of the compound, for example, in methanol, with a stoichiometric amount of hydrochloric acid or hydrogen chloride in methanol, ethanol, diethyl ether, or other suitable solvent, followed by evaporation of solvents.

Alternatively, hydrochloride salts can be obtained during deprotection of N-t-butoxycarbonyl group on piperidine nitrogen using hydrogen chloride in methanol, ethanol, diethyl ether or other suitable solvent, followed by evaporation of solvents, as exemplified on transformation of compound B-8 into compound B-9 In the treatment of the above-mentioned diseases, the compounds of formula (I) can be administered as a chemical compound, but typically they will be used in the form of pharmaceutical compositions, comprising a compound of formula (I) or a pharma- Initially, 3-bromo-2-methylaniline B-1 was treated with trifluoroacetic anhydride to afford amide B-2. The resulting product B-2 was reacted subsequently with bromine in the presence of the benzoyl peroxide and light, providing compound B-3. Next, benzyl bromide B-4 was converted to phosphonium derivative and cyclized in hot DMF to afford indole B-4. Protection on the indole nitrogen with benzyl group followed by coupling reaction with piperazine derivative ($R^1$=Me, BOC) gave compound B-6. Benzyl deprotection in the presence of oxygen and potassium tert-butoxide ceutically acceptable salt thereof as defined above as active ingredient, in combination with pharmaceutically acceptable carriers and/or excipients.

In the treatment of the abovementioned diseases, the compound of formula (I) or a pharmaceutical composition of the present invention can be administered by any route, preferably orally or parenterally, and will have the form of a formulation intended for use in medicine, depending upon the intended route of administration.

Solid formulations can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, sucrose, carboxymethylcellulose, microcrystalline cellulose or calcium hydrogen phosphate); lubricants (e.g., magnesium stearate, talc or silica); disintegrants (e.g., crospovidone, potato starch or sodium starch glycolate); wetting agents (e.g., sodium lauryl sulphate). The tablets may be coated according to methods well known in the art with conventional coatings, coatings for delaying/controlling release or enteric coatings.

Liquid formulations for oral administration may take the form of, for example, solutions, syrups or suspensions, or may be presented as a dry product for reconstitution with water or other suitable vehicle before use. Such liquid formulations may be prepared by conventional means with pharmaceutically acceptable excipients such as suspending agents (e.g., sorbitol syrup, cellulose derivatives or hydrogenated edible fats); emulsifying agents (e.g., lecithin or acacia); non-aqueous vehicles (e.g., olej almond oil, oily esters, ethyl alcohol or fractionated vegetable oils); and preservatives (e.g., methyl p- or propyl hydroxybenzoate or sorbic acid). Formulations may also comprise suitable buffers, flavoring agents, coloring agents, and sweeteners.

Formulations for oral administration may be suitably formulated by methods known to those skilled in the art to obtain a controlled release of the active compound.

Parenteral administration includes administration by intramuscular and intravenous injection or infusion. Formulations for parenteral administration may be in unit dosage form, for example, in ampoules or in multidose containers, with a preservative added. The compositions may take forms of suspensions, solutions or emulsions in oily or aqueous vehicles, and may contain formulating agents such as suspending, stabilizing and/or dispersing agents.

Alternatively, compounds of formula (I) can be in powder form for reconstitution with a suitable vehicle, e.g. sterile pyrogen-free water.

The method of treatment using the compounds of this invention will involve administration of a therapeutically effective amount of a compound of the invention, preferably in the form of a pharmaceutical composition to a subject in need of such treatment.

A proposed dose of the compounds of the present invention is from about 0.1 to about 1000 mg per day, in single or divided doses. The skilled person will appreciate that the selection of the dose required to achieve the desired biological effect will depend on a number of factors, for example the specific compound, the use, the mode of administration, the age and condition of the patient and the precise dosage will be ultimately determined at the discretion of the attendant physician.

EXAMPLES

Abbreviations
AcOEt ethyl acetate
AcOH acetic acid
ACN acetonitrile
br s broad singlet
$CHCl_3$ chloroform
d doublet
dd doublet of doublets
ddd doublet of doublet of doublets
dq doublet of quartets
DCM dichloromethane
$Et_2O$ diethyl ether
DIPEA N,N'-diisopropyl-N"-ethylamine
DMSO dimethylsulfoxide
EtOH ethanol
eq equivalents
ESI electrospray ionization
h hour(s)
HCl hydrogen chloride
HPLC High-Performance Liquid Chromatography
LiOH lithium hydroxide
L Litre(s)
m multiplet
MeOH methanol
$MgSO_4$ magnesium sulfate
mL milliliter(s)
$NaHCO_3$ sodium bicarbonate
$Na_2S_2O_4$ sodium dithionite
NaOH sodium hydroxide
$Na_2SO_4$ sodium sulfate
NMR Nuclear Magnetic Resonance
$K_2CO_3$ potassium carbonate
i-PrOH 2-propanol, iso-propanol
q quartet
RP-HPLC Reversed-Phase High-Performance Liquid Chromatography
s singlet
sep septet
SQD MS Single Quadrupole Detector Mass Spectrometer
t triplet
TFA trifluoroacetic acid
TFAA trifluoroacetic anhydride
THF tetrahydrofuran
TLC Thin-Layer Chromatography
UPLCMS Ultra Performance Liquid Chromatography Mass Spectrometry TLC were performed with silicagel 60 $F_{254}$ on aluminum foils (Sigma-Aldrich, Merck) using appropriate solvent systems. Visualization was generally done by UV light (254 nm).

UPLC-MS Method:
Method A:

UPLCMS analyses were performed on a UPLC liquid chromatograph equipped with PDA detector and SQD MS detector, operating under ESI(+) or ESI(−) using $C_{18}$ column, 2.1 mm×100 mm, 1.7 μm (AQUITY UPLC BEH or equivalent). HPLC or LC/MS grade methanol, HPLC grade water, HPLC or LC/MS grade formic acid, p.a. grade 25% solution of ammonia and mixture of them were used as a mobile phase. Operating conditions were the following: mobile phase flow 0.45 mL/min, wavelength 210-400 nm, injection volume 1 μL, column temperature 60° C., autosampler temperature 5° C.

The analysis was conducted 3.3 min+0.5 min for the delay of the next injection. Gradient elution with a linear course:

| Time [min] | % A | % B | Gradient curve |
|---|---|---|---|
| 0.0 | 95 | 5 | — |
| 1.8 | 5 | 95 | linear (6) |
| 3.3 | 95 | 5 | immediate (11) |

The analysis was conducted 5.5 min+1.5 min for "the delay of the next injection". Gradient elution with a linear course:

| Time [min] | % A | % B | Gradient curve |
|---|---|---|---|
| 0.0 | 80.0 | 20.0 | — |
| 4.0 | 0.1 | 99.9 | linear (6) |
| 5.5 | 80.0 | 20.0 | immediate (11) |

The Solutions were Prepared as Follows:

Preparation of the mobile phase A1—basic gradient: 25 µL of formic acid and 250 µL of 25% ammonia solution were added to 250 mL of water. Degas using an ultrasonic bath for 10 min.

Preparation of the mobile phase A2—acidic gradient: 50 µL of formic acid was added to 250 mL of water. Degas using an ultrasonic bath for 10 min.

Mobile phase B: Methanol Super Gradient.

Method B:

The UPLC-MS or UPLC-MS/MS analyzes were run on UPLC-MS/MS system comprising Waters ACQUITY UPLC (Waters Corporation, Milford, MA, USA) coupled with a Waters TQD mass spectrometer (electrospray ionization mode ESI with tandem quadrupole). Chromatographic separations were carried out using the Acquity UPLC BEH (bridged ethyl hybrid) $C_{18}$ column: 2.1 mm×100 mm and 1.7 µm particle size. The column was maintained at 40° C. and eluted under gradient conditions using 95% to 0% of eluent A over 10 min, at a flow rate of 0.3 mL/min. Eluent A, water/formic acid (0.1%, v/v); eluent B, acetonitrile/formic acid (0.1%, v/v). A total of 10 µL of each sample were injected, and chromatograms were recorded using a Waters eλ PDA detector. The spectra were analyzed in the range of 200-700 nm with 1.2 nm resolution and at a sampling rate of 20 points/s. MS detection settings of Waters TQD mass spectrometer were as follows: source temperature 150° C., desolvation temperature 350° C., desolvation gas flow rate 600 L/h, cone gas flow 100 L/h, capillary potential 3.00 kV, and cone potential 20 V.

Nitrogen was used for both nebulizing and drying. The data were obtained in a scan mode ranging from 50 to 1000 m/z at 0.5 s intervals; 8 scans were summed up to obtain the final spectrum. Collision activated dissociation (CAD) analyzes were carried out with the energy of 20 eV, and all the fragmentations were observed in the source. Consequently, the ion spectra were obtained in the range from 50 to 500 m/z. MassLynx V 4.1 software (Waters) was used for data acquisition. Standard solutions (1 mg/mL) of each compound were prepared in a mixture comprising analytical grade acetonitrile/water (1/1, v/v).

Synthetic Procedures

A. Compounds Based on Benzimidazole Core:

Compound A-2A: Tert-Butyl 4-(3-Fluoro-2-Nitrophenyl)Piperazine-1-Carboxylate

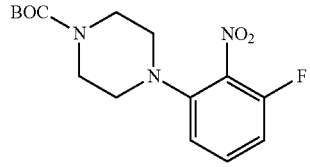 [SMILES: CC(C)(C)OC(=O)N1CCN(c2cccc(F)c2[N+](=O)[O-])CC1]

To a 1 L flask equipped with mechanical stirrer, 2,6-difluoronitrobenzene (16.5 g, 104 mmol) was added and flask was filled with DMSO (170 mL). Then, dried $K_2CO_3$ (31.6 g, 229 mmol) and N-BOC-piperazine (21.2 g, 114 mmol) were added. The reaction mixture was heated to 40° C. and stirred for 2.5 h at this temperature. The reaction was poured into water (400 mL) and diluted with DCM (500 mL). Phases were separated and the organic phase was washed with water (2×150 mL), brine (100 mL), dried under $MgSO_4$ and the solvent was removed in vacuo. The solid residue was dissolved in MeOH (120 mL) then water (15 mL) was added dropwise and the whole mixture was cooled to 5° C., and stored at this temperature for 2 h. After this time, solid product A-2A (21.9 g) was filtered and washed with the mixture of MeOH:water (10:1, 20 mL). The filtrate was reduced to the half of its volume and stored at 5° C. for 16 h. Additional portion of compound A-2A (6.3 g) was filtered and combined with previously obtained solid. As a result, product A-2A was obtained as the yellow solid (28.2 g, 83% yield) with 95% of purity, according to UPLCMS analysis (Method A).

Compound A-3A: Tert-Butyl 4-[3-(Benzylamino)-2-Nitrophenyl]Piperazine-1-Carboxylate

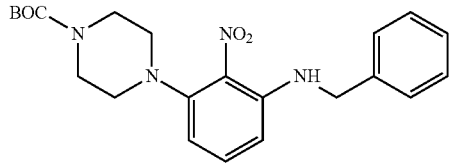 [SMILES: CC(C)(C)OC(=O)N1CCN(c2cccc(NCc3ccccc3)c2[N+](=O)[O-])CC1]

To a 250 mL flask equipped with magnetic stirring bar, compound A-2A (12 g, 45 mmol) was added under argon atmosphere and flask was filled with dry DMSO (100 mL). Then, dried $K_2CO_3$ (9.31 g, 67.5 mmol) and benzylamine (5.82 g, 54 mmol) were added, and the reaction mixture was heated to 120° C. and stirred for 2 h at this temperature. After this time UPLCMS analysis showed 1% of substrate peak area. The reaction was poured into ice (around 150 g) and diluted with AcOEt (300 mL). Phases were separated and the water phase was extracted with AcOEt (2×300 mL). Combined organic phases were washed with water, brine and solvent was removed in vacuo. As a result, the product A-3A was obtained as the yellow solid (11.9 g, 84% yield) with 95% of purity, according to UPLCMS analysis (Method A) and was used in the next step without any further purification.

Compound A-4A: Tert-Butyl 4-[2-Amino-3-(Benzylamino)Phenyl]Piperazine-1-Carboxylate

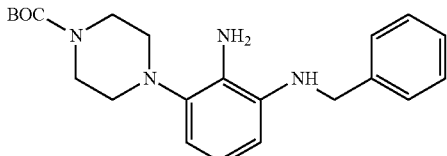

To a 500 mL flask equipped with magnetic stirring bar, compound A-3A (4 g, 9.7 mmol) and EtOH (200 mL) were added and the reaction mixture was heated to 80° C. Then, a freshly prepared solution of sodium dithionite (5.06 g, 29.1 mmol) in water (50 mL) was added within one minute. The reaction mixture was stirred for additional 15 minutes at 80° C. and then it was cooled to the room temperature. EtOH was removed and AcOEt (30 mL) was added. Phases were separated and the water phase was extracted once more with AcOEt (30 mL). Combined organic phases were washed with water, brine, dried under $Na_2SO_4$ and solvent was removed in vacuo. The crude product A-4A was obtained as a dark brown oil (3.01 g) and was used in the next step without any further purification.

Compound A-5A. Compound 1: 1-Benzyl-4-(Piperazin-1-Yl)-2-(Trifluoromethyl)-1H-Benzimidazole, in Form of Hydrochloride Salt

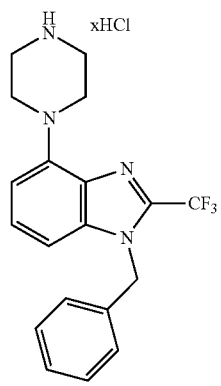 [SMILES: FC(F)(F)c1nc2c(N3CCNCC3)cccc2n1Cc1ccccc1]

To a 10 mL flask equipped with magnetic stirring bar, compound A-4A (382 mg, 1 mmol) and TFA (2 mL) were added and the reaction mixture was heated to 80° C. The reaction mixture was stirred for 16 hours. After this time UPLCMS analysis showed full consumption of the substrate. The reaction mixture was cooled to room temperature and diluted with DCM (50 mL), and saturated solution of $NaHCO_3$ was added dropwise to achieve pH~8. Then, water and DCM were added and phases were separated. Water phase was extracted with DCM (2×20 mL) and combined organic phases were washed with water, brine, dried under $Na_2SO_4$ and solvent was removed in vacuo. The residue was purified using column chromatography (10% to 20% of MeOH in DCM). Fractions with product were concentrated, redissolved in 20 ml of i-PrOH and 0.5 mL of 36% solution of HCl was added. Solvents was removed in vacuo and the residue was dissolved in 5 ml of i-PrOH, and then 20 ml of $Et_2O$ was added. The solid product was filtered and washed with $Et_2O$ (5 mL). As a result, the final product A-5A, Compound 1 in form of hydrochloride salt was obtained as the beige solid (141 mg, 39% yield) with 99.24% of purity, according to UPLCMS analysis (Method A).

$^1$H NMR (500 MHz, DMSO-$d_6$)δ9.53 (d, J=6.7 Hz, 2H), 7.37-7.25 (m, 4H), 7.19 (d, J=8.2 Hz, 1H), 7.11-7.03 (m, 2H), 6.78 (d, J=7.8 Hz, 1H), 5.67 (s, 2H), 3.80 (dd, J=6.6, 3.8 Hz, 4H), 3.30 (m, J=4.9 Hz, 4H).

$^{13}$C NMR (125 MHz, DMSO-$d_6$)δ143.20, 137.63, 137.46, 137.31 (q, J=38.2 Hz), 132.61, 129.22, 128.20, 127.05, 126.51, 119.40 (q, J=271.1 Hz), 108.98, 104.74, 48.12, 46.39, 42.92.

Compound A-3B: N-Benzyl-3-(4-Methylpiperazin-1-Yl)-2-Nitroaniline

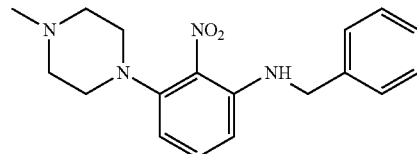

To a 100 mL flask equipped with magnetic stirring bar, 2,6-difluoronitrobenzene A-1 (5 g, 31 mmol) was added under argon atmosphere and flask was filled with dry DMSO (50 mL). Then, dried $K_2CO_3$ (8.5 g, 62 mmol) and 1-methylpiperazine (3.3 g, 33 mmol) were added. The reaction mixture was heated to 30° C. and stirred for 16 h. After this time UPLCMS analysis showed no substrate peak. Another portion of $K_2CO_3$ (5.1 g, 37 mmol) was added to reaction mixture followed by benzylamine (3.96 g, 37 mmol). The reaction mixture was heated to 70° C. and stirred for 16 h. After this time UPLCMS analysis showed 70% conversion of compound A-2B. One more portion of $K_2CO_3$ (3 g, 22 mmol) was added and stirring was continued overnight at 70° C. After this time UPLCMS analysis showed no compound A-2B in the reaction mixture. The reaction was poured into ice (around 400 g) where product began to crystallize. Solid was filtered and rinsed with water. Such obtained, crude, wet compound A-3B was used in the next step without further purification.

Compound A-4B: N$^1$-Benzyl-3-(4-Methylpiperazin-1-Yl)Benzene-1,2-Diamine

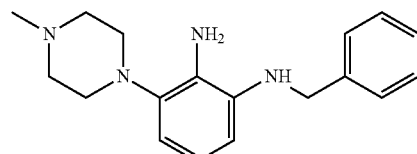

To a 1 L flask equipped with magnetic stirring bar, wet compound A-3B from previous step and EtOH (500 mL) were added and the reaction mixture was heated to 80° C. Then, a freshly prepared solution of sodium dithionite (16.2 g, 93 mmol) in water (100 mL) was added within 5 minutes. The reaction mixture was stirred for additional 15 minutes at 80° C. and then it was cooled to the room temperature. EtOH was removed under vacuum and AcOEt (200 mL) was added. Phases were separated and the water phase was extracted once more with AcOEt (30 mL). Combined organic phases were washed with water, brine, dried under Na₂SO₄ and solvent was removed in vacuo. The crude product A-4B was obtained as a dark brown oil (4.2 g) and was used in the next step without any further purification.

Compound A-5B. Compound 2: 1-Benzyl-4-(4-Methylpiperazin-1-Yl)-2-(Trifluoromethyl)-1H-Benzimidazole, in Form of Hydrochloride Salt

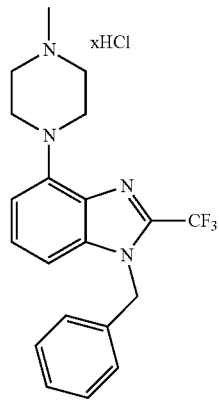 [SMILES: CN1CCN(c2cccc3c2nc(C(F)(F)F)n3Cc2ccccc2)CC1]

To a 90 mL flask equipped with magnetic stirring bar, compound A-4B (600 mg, 2 mmol) and TFA (5.8 g, 51 mmol) were added under argon atmosphere and a reaction mixture was heated at 80° C. for 2 h. Excess of acid was removed under vacuum. Residue was dissolved 15 ml of dry IPA and 5 ml of 36% solution of HCl was added. After 1 hour stirring mixture was evaporated to dryness. Residue was refluxed with 5 ml of dioxane and few drops of IPA for 30 min. Solution was cooled at 3° C. for night without stirring. Then, solid was filtered, washed with dioxane and dry in vacuum dryer. As a result, the final product A-5B, Compound 2 in form of hydrochloride salt was obtained as the beige solid (100 mg, 12% yield) with 98.09% of purity, according to UPLCMS analysis (Method A).

$^1$H NMR (500 MHz, DMSO-d₆)δ11.41 (s, 1H), 7.39-7.25 (m, 4H), 7.21 (d, J=8.2 Hz, 1H), 7.11-7.03 (m, 2H), 6.79 (d, J=7.8 Hz, 1H), 5.68 (s, 2H), 4.55-4.24 (m, 2H), 3.65-3.44 (m, 2H), 3.46-3.19 (m, 4H), 2.82 (s, 3H). $^{13}$C NMR (125 MHz, DMSO-d₆)δ142.82, 137.61, 137.36 (q, J=37.9 Hz), 136.38, 132.63, 129.49, 129.22, 128.20, 127.04, 126.52, 120.48, 118.32, 109.14, 104.83, 52.48, 48.13, 46.51, 42.49, 25.92.

Compound A-2C: 2-[4-(3-Fluoro-2-Nitrophenyl)Piperazin-1-Yl]Ethyl Acetate

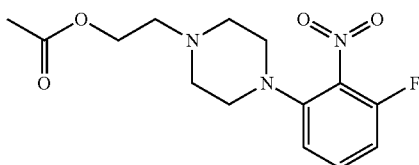

To a 250 mL flask equipped with magnetic stirring bar, 1-(3-fluoro-2-nitrophenyl)piperazine A-6 (5 g, 22.5 mmol) was added under argon atmosphere and the flask was filled with dry ACN (50 mL). Then, dried K₂CO₃ (6.0 g, 45 mmol) and 2-bromoethyl acetate (4.45 g, 26.6 mmol) were added, and the reaction mixture was heated to 60° C. and stirred for 20 h at this temperature. After this time UPLCMS analysis showed no substrate peak. The reaction was cooled to room temperature and solid was filtered. As a result, the product A-2C was obtained as the yellow solid (6.8 g, 99% yield) with 99% of purity, according to UPLCMS analysis (Method A).

Compound A-3C: 2-{4-[3-(Benzylamino)-2-Nitrophenyl]Piperazin-1-Yl}Ethyl Acetate

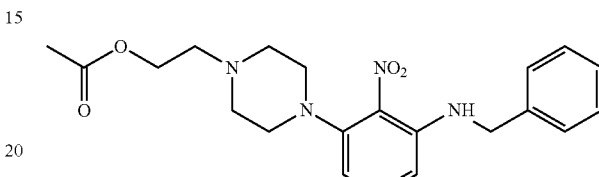

To a 100 mL flask equipped with magnetic stirring bar, compound A-2C (6.6 g, 22 mmol) was added under argon atmosphere and the flask was filled with dry DMSO (60 mL). Then, dried K₂CO₃ (6.07 g, 44 mmol) and benzylamine (2.59 g, 24.2 mmol) were added, and the reaction mixture was heated to 70° C. and stirred for 20 h at this temperature. After this time reaction was poured into ice (around 60 g) and diluted with AcOEt (300 mL). Phases were separated and the water phase was extracted with AcOEt (2×300 mL). Combined organic phases were washed with water, brine and the solvent was removed in vacuo. As a result, the product A-3C was obtained as the yellow solid (6.3 g, 72% yield) and was used in the next step without any further purification.

Compound A-5C, Compound 3: 2-{4-[1-Benzyl-2-(Trifluoromethyl)-1H-Benzimidazol-4-Yl]Piperazin-1-Yl}Ethanol, in Form of Hydrochloride Salt

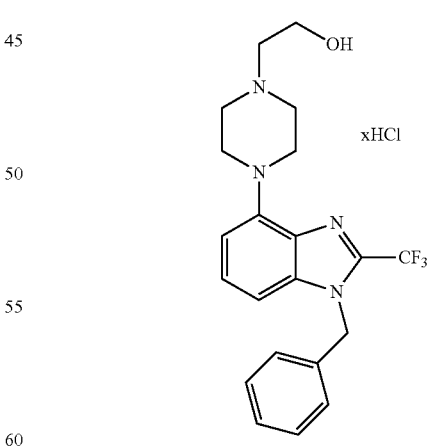

In a 50 mL flask equipped with magnetic stirring bar, TFA (10 mL) was added and the mixture was heated to 70° C. Then, metallic iron (1.12 g, 20 mmol) and compound A-3C (2.0 g, 5 mmol) were added. The reaction mixture was stirred for 2 hours at this temperature. After this time the reaction mixture was cooled to room temperature and diluted with DCM (100 mL). 2M solution of NaHCO₃ was added dropwise to achieve pH~8 and then phases were separated. Water phase was extracted with DCM (2×100 mL) and combined organic phases were washed with water, brine, dried under Na₂SO₄, and the solvent was removed in vacuo. The residue was dissolved in 50 ml of THF and then 5 ml of water and 1 g of LiOH were added. The reaction mixture was stirred for 20 hours at room temperature. After this time organic solvent was removed in vacuo and into the mixture 100 ml of AcOEt was added. Phases were separated and the water phase was extracted with AcOEt (2×100 mL). Combined organic phases were washed with water, brine and solvent was removed in vacuo. The residue was purified using column chromatography (10% to 20% of MeOH in DCM). After removing of solvents residue was dissolved in 20 ml of i-PrOH and 0.5 mL of 36% solution of HCl was added. Solvents were removed in vacuo and the residue was redissolved in 5 ml of i-PrOH and then 20 ml of Et₂O was added. The solid product was filtered and washed with Et₂O. As a result final compound A-5C, Compound 3 in form of hydrochloride salt was obtained as the beige solid (81 mg, 3.7% yield) with 97% of purity, according to UPLCMS analysis (Method A).

¹H NMR (500 MHz, DMSO-d₆)δ10.78 (s, 1H), 7.37-7.25 (m, 4H), 7.20 (d, J=8.2 Hz, 1H), 7.10-7.04 (m, 2H), 6.78 (d, J=7.8 Hz, 1H), 5.67 (s, 2H), 4.39 (d, J=11.9 Hz, 2H), 3.85 (dd, J=6.2, 4.3 Hz, 2H), 3.67 (d, J=11.2 Hz, 2H), 3.37 (m, 4H), 3.26 (q, J=5.2 Hz, 2H).

¹³C NMR (125 MHz, DMSO-d₆)δ142.82, 137.62, 137.34 (q, J=37.4), 136.39, 132.59, 129.23, 128.22, 127.05, 126.52, 119.40 (q, J=270.7 Hz), 109.04, 104.82, 58.30, 55.45, 51.56, 48.12, 46.32.

Compound A-3D: Tert-Butyl 4-(3-(Furan-2-Ylmethylamino)-2-Nitrophenyl)Piperazine-1-Carboxylate

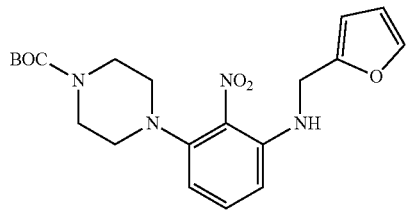

To a 50 mL flask equipped with magnetic stirring bar, compound A-2A (1.63 g, 5 mmol) was added under argon atmosphere and the flask was filled with dry DMSO (6 mL). Then, dried K₂CO₃ (2.07 g, 15 mmol) and furfurylamine (6.5 mmol, 631 mg) were added, and the reaction mixture was heated to 80° C. and stirred for 16 h at this temperature. After this time UPLCMS analysis showed 5% of the substrate A-2A peak area. The reaction was poured into ice (around 50 g) and diluted with AcOEt (30 mL). Phases were separated and the water phase was extracted with AcOEt (2×30 mL). Combined organic phases were washed with water, brine and solvent was removed in vacuo. A solid residue was dissolved in a small amount of MeOH with gentle heating and then stored at 5° C. overnight. Such obtained solid was filtered, rinsed with cold MeOH (5 mL) and dried under high vacuum. The filtrate was concentrated in vacuo, preadsorbed onto silicagel and purified using gravity column chromatography (10% of AcOEt in n-hexane). After removing of solvents the product was combined with previously obtained solid. As a result, the product A-3D was obtained as the red-brown solid (1.29 g, 64% yield) with 98% of purity, according to UPLCMS analysis.

Compound A-4D: Tert-Butyl 4-(2-Amino-3-(Furan-2-Ylmethylamino)Phenyl)Piperazine-1-Carboxylate

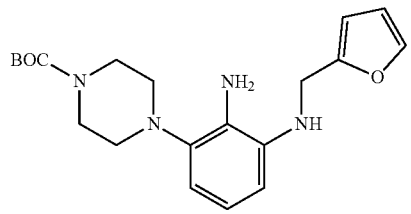 [SMILES: CC(C)(C)OC(=O)N1CCN(c2cccc(NCc3ccco3)c2[N+](=O)[O-])CC1]

To a 100 mL flask equipped with magnetic stirring bar, compound A-3D (850 mg, 2.1 mmol) and EtOH (20 mL) were added and the reaction mixture was heated to 80° C. Then, a freshly prepared solution of sodium dithionite (1.83 g, 10.5 mmol) in water (12 mL) was added within one minute. The reaction mixture was stirred for additional 15 minutes at 80° C. and then it was cooled to the room temperature. EtOH was removed and AcOEt (30 mL) was added. Phases were separated and the water phase was extracted once more with AcOEt (30 mL). Combined organic phases were washed with water, brine, dried under Na₂SO₄ and solvent was removed in vacuo. The crude product A-4D was obtained as a dark brown oil (705 mg) and was used in the next step without any further purification.

Compound A-8A: Tert-Butyl 4-(1-(Furan-2-Ylmethyl)-2-(Trifluoromethyl)-1H-Benzimidazol-4-Yl)Piperazine-1-Carboxylate

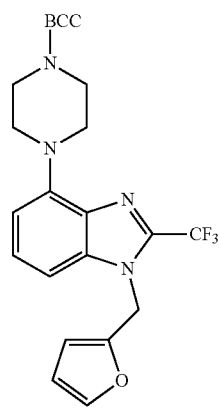

To a 10 mL flask equipped with magnetic stirring bar, compound A-4D (100 mg, 0.27 mmol) and dry ACN were added under argon atmosphere and a reaction mixture was cooled to 0° C. Then, DIPEA (243 mg, 1.88 mmol) was added followed by dropwise (0.5 h) addition of freshly prepared solution of TFAA (216 mg, 1.03 mmol) in ACN (1 mL). The reaction mixture was stirred at room temperature for 16 h. After this time UPLCMS analysis showed 15% of product peak area of A-8A and 35% peak area of non-cyclized product A-7A. The reaction mixture was diluted with DCM and water and phases were separated. Water phase was extracted with DCM (2×20 mL) and combined organic phases were washed with water, brine and solvent was removed in vacuo. The residue was preadsorbed onto silicagel and purified using column chromatography (10% to 15% of AcOEt in n-hexane). After removing of solvents two fractions were obtained. First fraction, expected product A-8A was obtained as a colourless oil (107 mg, 44% yield) with 99% of purity according to UPLCMS analysis (Method A). Second fraction (100 mg) was the mixture (1:1) of expected product A-8A and non-cyclized product A-7A. It is possible to convert quantitatively this mixture into pure compound A-8A using AcOH in refluxing EtOH.

Compound A-5D. Compound 4: 1-(Furan-2-Ylmethyl)-4-(Piperazin-1-Yl)-2-(Trifluoromethyl)-1H-Benzimidazole

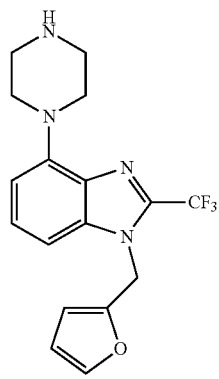 [SMILES: FC(F)(F)c1nc2c(N3CCNCC3)cccc2n1Cc1ccco1]

To a 25 mL flask equipped with magnetic stirring bar, compound A-8A (100 mg, 0.22 mmol) and EtOH (2 mL) were added followed by 36% solution of HCl (0.5 mL) and the reaction mixture was stirred for 40 h. After this time UPLCMS analysis showed full consumption of the substrate. The reaction mixture was diluted with EtOH (5 mL), cooled to around 5° C. and 25% solution of NH₄OH (0.5 mL) was added dropwise. Then, water and DCM were added and phases were separated. Water phase was extracted with DCM (2×20 mL) and combined organic phases were washed with water, brine, dried under Na₂SO₄ and solvent was removed in vacuo. As a result, the final product A-5D, Compound 4 was obtained as the light brown solid (59 mg, 76% yield) with 97.34% of purity, according to UPLCMS analysis (Method A).

$^1$H NMR (500 MHz, DMSO-$d_6$) δ7.59 (d, J=1.6 Hz, 1H), 7.34-7.26 (m, 2H), 6.66 (ddd, J=10.6, 5.6, 3.2 Hz, 1H), 6.55 (d, J=3.2 Hz, 1H), 6.42 (dd, J=3.3, 1.8 Hz, 1H), 5.60 (s, 2H), 3.42 (m, 4H), 2.90 (m, 4H).

$^{13}$C NMR (125 MHz, DMSO-$d_6$) δ149.34, 145.53, 144.41, 137.69, 136.82 (q, J=38.2 Hz), 133.01, 127.36, 119.94 (q, J=271.5 Hz), 111.59, 110.35, 108.70, 104.01, 51.13, 46.42, 41.97.

Compound A-3E: Tert-Butyl 4-(3-((5-Methylfuran-2-Yl)Methylamino)-2-Nitrophenyl)Piperazine-1-Carboxylate

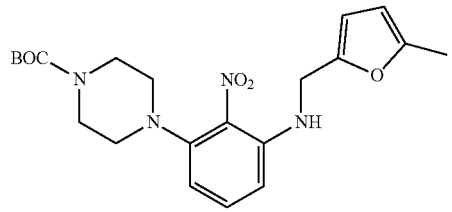 [SMILES: Cc1ccc(CNc2cccc(N3CCN(C(=O)OC(C)(C)C)CC3)c2[N+](=O)[O-])o1]

To a 50 mL flask equipped with magnetic stirring bar, compound A-2A (650 mg, 2 mmol) was added under argon atmosphere and flask was filled with dry DMSO (4 mL). Then, dried K₂CO₃ (691 mg, 5 mmol) and 5-methylfurfurylamine (2.6 mmol, 289 mg) were added, and the reaction mixture was heated to 80° C. and stirred for 16 h. After this the reaction mixture was poured into water (around 50 mL) and diluted with DCM (20 mL). Phases were separated and the water phase was extracted with DCM (2×20 mL). Combined organic phases were washed with water, brine, dried under MgSO₄ and the solvent was removed in vacuo. The residue was preadsorbed onto silicagel and purified using column chromatography (10% of AcOEt in n-hexane). As a result, the final product A-3E was obtained as the red-brown solid (450 mg, 54% yield) with 95% of purity, according to UPLCMS analysis (Method A).

Compound A-4E: Tert-Butyl 4-(2-Amino-3-((5-Methylfuran-2-Yl)Methylamino)Phenyl)Piperazine-1-Carboxylate

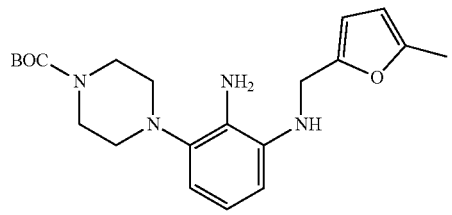 [SMILES: Cc1ccc(CNc2cccc(N3CCN(C(=O)OC(C)(C)C)CC3)c2N)o1]

To a 50 mL flask equipped with magnetic stirring bar, compound A-3E (492 mg, 1.18 mmol) and EtOH (17 mL) were added and the reaction mixture was heated to 80° C. Then, a freshly prepared solution of sodium dithionite (1.21 g, 5.9 mmol) in water (4.3 mL) was added in one portion. The reaction mixture was stirred for additional 10 minutes at 80° C. and then it was cooled to the room temperature. Water (20 mL) and AcOEt (30 mL) was added and phases were separated. Water phase was extracted with AcOEt (2×30 mL). Combined organic phases were washed with water, brine, dried under MgSO₄ and the solvent was removed in vacuo. The crude product A-4E was obtained as a dark brown oil (402 mg) and was used in the next step without any further purification (Method A).

Compound A-8B: Tert-Butyl 4-(1-((5-Methylfuran-2-Yl)Methyl)-2-(Trifluoromethyl)-1H-Benzimidazol-4-yl)Piperazine-1-Carboxylate

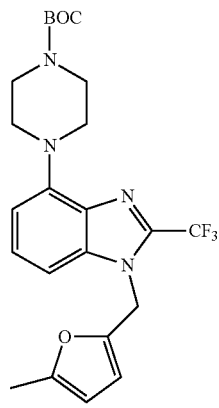 [SMILES: Cc1ccc(Cn2c(C(F)(F)F)nc3c(N4CCN(C(=O)OC(C)(C)C)CC4)cccc32)o1]

To a 25 mL flask equipped with magnetic stirring bar, compound A-4E (216 mg, 0.56 mmol) and dry ACN were added under argon atmosphere. Then, DIPEA (145 mg, 1.12 mmol) was added followed by dropwise (20 min) addition of TFAA (130 mg, 0.62 mmol). The reaction mixture was stirred at room temperature for 16 h. After this time UPLCMS analysis showed 15% of product A-8B peak area and 35% peak area of non-cyclized product A-7B. The reaction mixture was poured into saturated solution of NaHCO₃ (20 mL), diluted with 30 ml of DCM and phases were separated. Water phase was extracted with DCM (2×20 mL) and combined organic phases were washed with water, brine, dried under MgSO₄ and solvent was removed in vacuo. The residue was dissolved in EtOH (6 mL) and 0.5 mL of AcOH was added. Then, the mixture was heated to 80° C. and stirred at this temperature for 2 h. After this time all solvents were removed and the residue was dissolved in AcOEt (10 mL). Organic phase was washed with saturated solution of NaHCO₃, dried under MgSO₄ and the solvent was removed in vacuo. The residue was preadsorbed onto silicagel and purified using column chromatography (20% of AcOEt in n-hexane). As a result, the product A-8B was obtained as the colourless oil (115 mg, 45% yield) with 99% of purity, according to UPLCMS analysis (Method A).

Compound A-5E. Compound 5: 1-((5-Methylfuran-2-Yl)Methyl)-4-(Piperazin-1-Yl)-2-(Trifluoromethyl)-1H-Benzimidazole

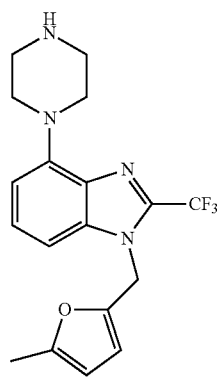 [SMILES: Cc1ccc(Cn2c(C(F)(F)F)nc3c(N4CCNCC4)cccc32)o1]

To a 25 mL flask equipped with magnetic stirring bar, compound A-8B (115 mg, 0.25 mmol) and EtOH (7 mL) were added followed by 36% solution of HCl (1.5 mL) and the reaction mixture was stirred for 24 h. After this time another portion of concentrated HCl (0.7 mL) was added and the reaction mixture was stirred additional 24 h. The reaction mixture was diluted with water (10 mL), cooled to around 5° C. and 25% solution of NH₄OH (2 mL) was added dropwise. Then DCM (30 mL) was added and phases were separated. Water phase was extracted once more with DCM (30 mL) and combined organic phases were washed with water, brine, dried under MgSO₄ and solvent was removed in vacuo. The residue was preadsorbed onto silicagel and purified using column chromatography (92:8:0.5 of DCM:MeOH:NH₄OH). As a result, the final product A-5E, Compound 5 was obtained as the light brown solid (60 mg, 66% yield) with 96% of purity, according to UPLCMS analysis (Method A).

¹H NMR (500 MHz, CDCl₃) δ 7.29 (t, J=8.0 Hz, 1H), 7.11 (d, J=8.0 Hz, 1H), 6.66 (d, J=8.0 Hz, 1H), 6.16 (m, 1H), 5.87 (m, 1H), 5.34 (s, 2H), 3.55 (m, 4H), 3.15 (m, 4H), 2.21 (s, 3H).

¹³C NMR (125 MHz, CDCl₃) δ 152.76, 146.23, 145.16, 137.33 (q, J=38.9 Hz), 136.98, 133.23, 126.21, 119.17 (q, J=271.1 Hz), 109.91, 108.16, 106.45, 103.11, 51.00, 46.08, 41.60, 13.47.

Compound A-3F: Tert-Butyl 4-(3-((3-Chlorobenzyl)Amino)-2-Nitrophenyl)Piperazine-1-Carboxylate

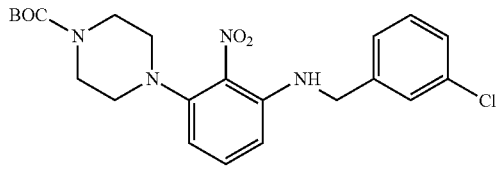 [SMILES: CC(C)(C)OC(=O)N1CCN(c2cccc(NCc3cccc(Cl)c3)c2[N+](=O)[O-])CC1]

To a 50 mL flask equipped with magnetic stirring bar, compound A-2A (1.20 g, 3.69 mmol) was added under argon atmosphere and flask was filled with dry DMSO (5 mL). Then, dried K₂CO₃ (0.97 g, 7.01 mmol) and 3-chlorobenzylamine (0.84 g, 5.91 mmol) were added, and the reaction mixture was heated to 70° C. and stirred for 48 h at this temperature. After that time, reaction mixture was cooled to a room temperature, poured into cold solution of brine (75 mL) and diluted with water (75 mL). The obtained precipitate was filtered off, washed with water, dried on air and crystalized from EtOH (99.9%, 10 mL) affording product A-3F as a yellow solid (0.77 g, 47% yield) with 100% of purity, according to UPLCMS analysis (Method B).

Compound A-4F: Tert-Butyl 4-(2-Amino-3-((3-Chlorobenzyl)Amino)Phenyl)Piperazine-1-Carboxylate

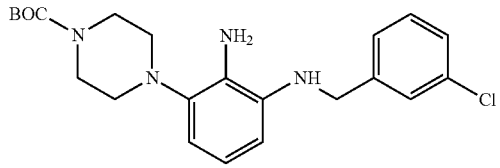 [SMILES: CC(C)(C)OC(=O)N1CCN(c2cccc(NCc3cccc(Cl)c3)c2N)CC1]

To a 100 mL flask equipped with magnetic stirring bar, compound A-3F (0.75 g, 1.68 mmol) and EtOH (28 mL) were added and the reaction mixture was heated to 80° C. Then, a freshly prepared solution of sodium dithionite (1.31 g, 7.55 mmol) in water (9 mL) was added within one minute. The reaction mixture was stirred for additional 15 minutes at 80° C. and then it was cooled to the room temperature. EtOH was removed and AcOEt (20 mL) was added. Phases were separated and the water phase was extracted once more with AcOEt (20 mL). Combined organic phases were washed with water, brine, dried under MgSO4 and solvent was removed in vacuo. The crude product A-4F was obtained as a beige crystallizing oil (0.63 g) and was used in the next step without further purification.

Compound A-5F, Compound 6: 1-(3-Chlorobenzyl)-4-(Piperazin-1-Yl)-2-(Trifluoromethyl)-1H-Benzimidazole. In Form of Hydrochloride Salt

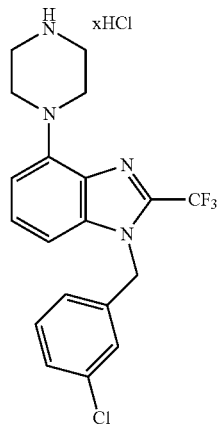 [SMILES: FC(F)(F)c1nc2c(N3CCNCC3)cccc2n1Cc1cccc(Cl)c1]

To a 10 mL flask equipped with magnetic stirring bar, compound A-4F (0.31 g, 0.74 mmol) and TFA (1.48 mL) were added and the reaction mixture was stirred at room temperature for 16 hours. After this time UPLCMS analysis showed full consumption of the substrate. The reaction mixture was cooled to room temperature and diluted with DCM (40 mL), and saturated solution of NaHCO3 was added dropwise to achieve pH~8. Then, water and DCM were added and phases were separated. Water phase was extracted with DCM (2×15 mL) and combined organic phases were washed with water, brine, dried under MgSO4 and solvent was removed in vacuo. The crude product was redissolved in 37 ml of i-PrOH and 0.3 mL of 36% solution of HCl was added. Solvents was removed in vacuo and the residue was dissolved in 5 ml of i-PrOH, and then 20 ml of Et2O was added. The solid product was filtered and washed with Et2O (5 mL). As a result, the final product A-5F, Compound 6 in form of hydrochloride salt was obtained as a beige solid (104 mg, 33% yield) with 100% of purity, according to UPLCMS analysis (Method B).

$^1$H NMR (300 MHz, DMSO-d$_6$)δ9.41 (br s, 2H), 7.38-7.26 (m, 3H), 7.23-7.14 (m, 2H), 6.91 (d, J=3.1 Hz, 1H), 6.77 (d, J=7.7 Hz, 1H), 5.68 (s, 2H), 3.77 (br s, 4H), 3.28 (br s, 4H)

$^{13}$C NMR (75 MHz, DMSO-d$_6$)δ143.2, 139.0, 137.6, 137.0 (q, J=2 Hz), 133.8, 132.5, 131.2, 128.2, 127.2, 126.5, 125.0, 119.3 (q, J=271 Hz), 109.1, 104.6, 47.4, 46.4, 43.0

Compound A-3G: Tert-Butyl 4-(3-((3-Fluorobenzyl)Amino)-2-Nitrophenyl) Piperazine-1-Carboxylate

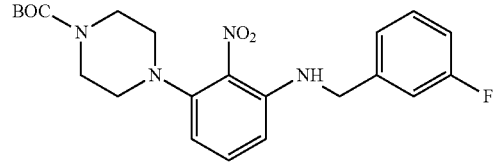 [SMILES: CC(C)(C)OC(=O)N1CCN(c2cccc(NCc3cccc(F)c3)c2[N+](=O)[O-])CC1]

To a 50 mL flask equipped with magnetic stirring bar, compound A-2A (1.20 g, 3.69 mmol) was added under argon atmosphere and flask was filled with dry DMSO (5 mL). Then, dried K2CO3 (0.97 g, 7.01 mmol) and 3-fluorobenzylamine (0.74 g, 5.91 mmol) were added, and the reaction mixture was heated to 70° C. and stirred for 48 h at this temperature. After that time, reaction mixture was cooled to a room temperature, poured into cold solution of brine (75 mL) and diluted with water (75 mL). The obtained precipitate was filtered off, washed with water, dried on air and crystalized from EtOH (99.9%, 10 mL) affording product A-3G as a yellow solid (0.73 g, 46% yield) with 100% of purity, according to UPLCMS analysis (Method B).

Compound A-4G: Tert-Butyl 4-(2-Amino-3-((3-Fluorobenzyl)Amino)Phenyl)Piperazine-1-Carboxylate

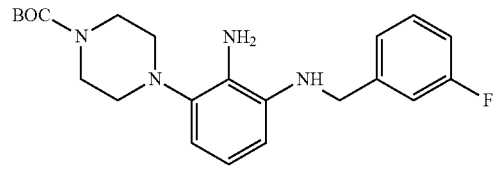

To a 100 mL flask equipped with magnetic stirring bar, compound A-3G (0.70 g, 1.63 mmol) and EtOH (27 mL) were added and the reaction mixture was heated to 80° C. Then, a freshly prepared solution of sodium dithionite (1.27 g, 7.32 mmol) in water (8 mL) was added within one minute. The reaction mixture was stirred for additional 15 minutes at 80° C. and then it was cooled to the room temperature. EtOH was removed and AcOEt (20 mL) was added. Phases were separated and the water phase was extracted once more with AcOEt (20 mL). Combined organic phases were washed with water, brine, dried under MgSO4 and solvent was removed in vacuo. The crude product A-4G was obtained as a pale beige oil (0.60 g) and was used in the next step without further purification.

Compound A-5G. Compound 7: 1-(3-Fluorobenzyl)-4-(Piperazin-1-Yl)-2-(Trifluoromethyl)-1H-Benzimidazole, in Form of Hydrochloride Salt

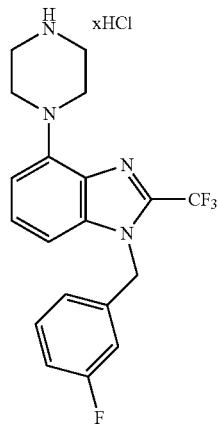 [SMILES: Fc1cccc(Cn2c(C(F)(F)F)nc3c(N4CCNCC4)cccc32)c1]

To a 10 mL flask equipped with magnetic stirring bar, compound A-4G (0.30 g, 0.75 mmol) and TFA (1.5 mL) were added and the reaction mixture was stirred at room temperature for 16 hours. After this time UPLCMS analysis showed full consumption of the substrate. The reaction mixture was cooled to room temperature and diluted with DCM (40 mL), and saturated solution of NaHCO$_3$ was added dropwise to achieve pH~8. Then, water and DCM were added and phases were separated. Water phase was extracted with DCM (2×15 mL) and combined organic phases were washed with water, brine, dried under MgSO$_4$ and solvent was removed in vacuo. The crude product was redissolved in 37 ml of i-PrOH and 0.3 mL of 36% solution of HCl was added. Solvents was removed in vacuo and the residue was dissolved in 5 ml of i-PrOH, and then 20 ml of Et$_2$O was added. The solid product was filtered and washed with Et$_2$O (5 mL). As a result, the final product A-5G, Compound 7 in form of hydrochloride salt was obtained as a beige solid (100 mg, 32% yield) with 98.84% of purity, according to UPLCMS analysis (Method B).

$^1$H NMR (300 MHz, DMSO-d$_6$) δ9.42 (br s, 2H), 7.39-7.27 (m, 2H), 7.18 (d, J=8.0 Hz, 1H), 7.10 (dt, J=2.6, 8.3 Hz, 1H), 6.93 (d, J=10.0 Hz, 1H), 6.82-6.74 (m, 2H), 5.68 (s, 2H), 3.81-3.74 (m, 4H), 3.28 (br s, 4H)

$^{13}$C NMR (75 MHz, DMSO-d$_6$) δ162.6 (d, J=244 Hz), 143.2, 139.3 (d, J=7.2 Hz), 137.6 (q, J=2 Hz), 137.0, 132.6, 131.4 (d, J=8.3 Hz), 127.2, 122.4 (d, J=2.8 Hz), 119.3 (d, J=271 Hz), 115.1 (d, J=21 Hz), 113.6 (d, J=22.5 Hz), 109.1, 104.6, 47.5, 46.4, 43.0

Compound A-3H: Tert-Butyl 4-(3-((3,4-Dichlorobenzyl)Amino)-2-Nitrophenyl)Piperazine-1-Carboxylate

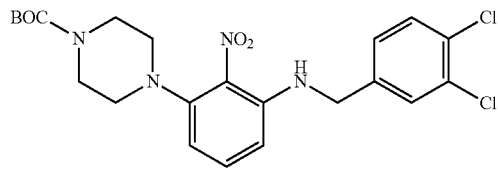

To a 50 mL flask equipped with magnetic stirring bar, compound A-2A (1.10 g, 3.38 mmol) was added under argon atmosphere and flask was filled with dry DMSO (5 mL). Then, dried K$_2$CO$_3$ (0.7 g, 5.07 mmol) and 3,4-dichlorobenzylamine (0.65 g, 3.72 mmol) were added, and the reaction mixture was heated to 70° C. and stirred for 24 h at this temperature. After that time, reaction mixture was cooled to a room temperature, poured into cold solution of brine (75 mL) and diluted with water (75 mL). The obtained precipitate was filtered off, washed with water, dried on air and crystalized from EtOH (99.9%, 10 mL) affording product A-3H as a red solid (0.7 g, 43% yield) with 94.4% of purity, according to UPLCMS analysis (Method B).

Compound A-4H: Tert-Butyl 4-(2-Amino-3-((3,4-Dichlorobenzyl)Amino)Phenyl)Piperazine-1-Carboxylate

To a 100 mL flask equipped with magnetic stirring bar, compound A-3H (0.7 g, 1.54 mmol) and EtOH (22 mL) were added and the reaction mixture was heated to 80° C. Then, a freshly prepared solution of sodium dithionite (1.08 g, 6.2 mmol) in water (7 mL) was added within one minute. The reaction mixture was stirred for additional 15 minutes at 80° C. and then it was cooled to the room temperature. EtOH was removed and AcOEt (15 mL) was added. Phases were separated and the water phase was extracted once more with AcOEt (15 mL). Combined organic phases were washed with water, brine, dried under MgSO$_4$ and solvent was removed in vacuo. The crude product A-4H was obtained as a yellowish oil (0.285 g) and was used in the next step without further purification.

Compound A-5H, Compound 8: 1-(3,4-Dichlorobenzyl)-4-(Piperazin-1-Yl)-2-(Trifluoromethyl)-1H-Benzo[d]Imidazole

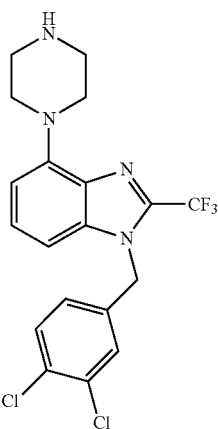 [SMILES: FC(F)(F)c1nc2c(N3CCNCC3)cccc2n1Cc1ccc(Cl)c(Cl)c1]

To a 10 mL flask equipped with magnetic stirring bar, compound A-4H (0.14 g, 0.33 mmol) and TFA (0.7 mL) were added and the reaction mixture was stirred at room temperature for 16 hours. After this time UPLCMS analysis showed full consumption of the substrate. The reaction mixture was cooled to room temperature and diluted with DCM (20 mL), and saturated solution of NaHCO$_3$ was added dropwise to achieve pH~8. Then, water and DCM were added and phases were separated. Water phase was extracted with DCM (2×10 mL) and combined organic phases were washed with water, brine, dried under MgSO$_4$ and solvent was removed in vacuo. The obtained crude product was purified using column chromatography (n-hexane/DCM/methanol/NH$_{3(aq)}$ 4.0/5.0/1.0/0.02, v/v/v/v) affording final product A-5H, Compound 8 as a pale yellow crystallizing oil (120 mg, 85% yield) with 95.75% of purity, according to UPLCMS analysis (Method B).

$^1$H NMR (300 MHz, DMSO-d$_6$)δ7.60-7.49 (m, 2H), 7.44-7.23 (m, 4H), 7.17-7.06 (m, 2H), 6.97-6.84 (m, 2H), 6.72-6.63 (m, 2H), 5.66 (s, 2H), 3.57-3.50 (m, 4H), 3.08-2.99 (m, 4H)

$^{13}$C NMR (75 MHz, CD$_3$OD) δ 166.1, 160.9, 145.1, 140.3, 136.5 (q, J=1.7 Hz), 136.7, 132.6, 126.7, 124.3, 120.2, 116.9 (q, J=271 Hz), 108.7, 108.1, 102.8, 50.1, 44.9, 43.8

Compound A-3I: Tert-Butyl 4-(3-((3-Chloro-4-Fluorobenzyl)Amino)-2-Nitrophenyl)Piperazine-1-Carboxylate

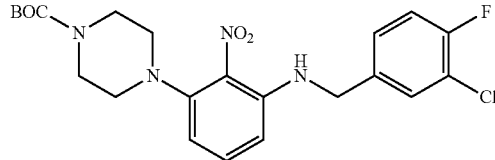 [SMILES: CC(C)(C)OC(=O)N1CCN(c2cccc(NCc3ccc(F)c(Cl)c3)c2[N+](=O)[O-])CC1]

To a 50 mL flask equipped with magnetic stirring bar, compound A-2A (1.1 g, 3.38 mmol) was added under argon atmosphere and flask was filled with dry DMSO (5 mL). Then, dried K$_2$CO$_3$ (1.16 g, 8.45 mmol) and 3-chloro-4-fluorobenzylamine (0.85 g, 5.4 mmol) were added, and the reaction mixture was heated to 70° C. and stirred for 24 h at this temperature. After that time, reaction mixture was cooled to a room temperature, poured into cold solution of brine (75 mL) and diluted with water (75 mL). The obtained precipitate was filtered off, washed with water, dried on air and crystalized from EtOH (99.9%, 10 mL) affording product A-3I as a yellowish solid (0.5 g, 32% yield) with 93% of purity, according to UPLCMS analysis (Method B).

Compound A-4I: Tert-Butyl 4-(2-Amino-3-((3-Chloro-4-Fluorobenzyl)Amino)Phenyl) Piperazine-1-Carboxylate

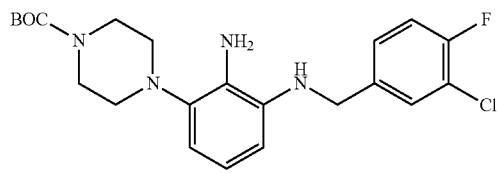 [SMILES: CC(C)(C)OC(=O)N1CCN(c2cccc(NCc3ccc(F)c(Cl)c3)c2N)CC1]

To a 100 mL flask equipped with magnetic stirring bar, compound A-3I (0.5 g, 1.07 mmol) and EtOH (15 mL) were added and the reaction mixture was heated to 80° C. Then, a freshly prepared solution of sodium dithionite (0.75 g, 4.37 mmol) in water (5 mL) was added within one minute. The reaction mixture was stirred for additional 15 minutes at 80° C. and then it was cooled to the room temperature. EtOH was removed and AcOEt (20 mL) was added. Phases were separated and the water phase was extracted once more with AcOEt (20 mL). Combined organic phases were washed with water, brine, dried under MgSO$_4$ and solvent was removed in vacuo. The crude product A-4I was obtained as a yellowish oil (0.452 g) and was used in the next step without further purification.

Compound A-5I, Compound 9: 1-(3-Chloro-4-Fluorobenzyl)-4-(Piperazin-1-Yl)-2-(Trifluoromethyl)-1H-Benzo[d]Imidazole

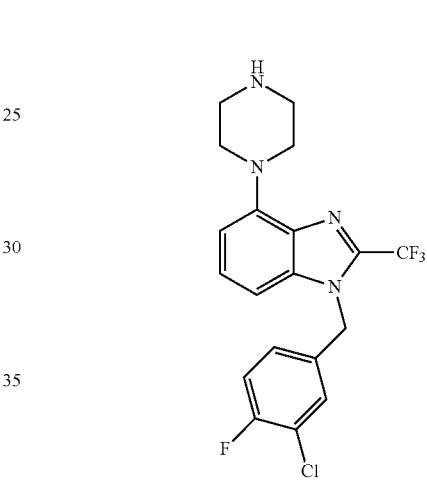

To a 10 mL flask equipped with magnetic stirring bar, compound A-4I (0.240 g, 0.55 mmol) and TFA (1.2 mL) were added and the reaction mixture was stirred at room temperature for 16 hours. After this time UPLCMS analysis showed full consumption of the substrate. The reaction mixture was cooled to room temperature and diluted with DCM (20 mL), and saturated solution of NaHCO$_3$ was added dropwise to achieve pH~8. Then, water and DCM were added and phases were separated. Water phase was extracted with DCM (2×10 mL) and combined organic phases were washed with water, brine, dried under MgSO$_4$ and solvent was removed in vacuo. The obtained crude product was purified using column chromatography (n-hexane/DCM/methanol/NH$_{3(aq)}$ 4.0/5.0/1.0/0.02, v/v/v/v) affording final product A-5I, Compound 9 as a yellow crystallizing oil (200 mg, 90% yield) with 97.50% of purity, according to UPLCMS analysis (Method B).

$^1$H NMR (300 MHz, DMSO-d$_6$)δ7.22-7.43 (m, 3H), 7.09 (d, J=7.69 Hz, 1H), 6.97 (ddd, J=2.18, 4.68, 8.53 Hz, 1H), 6.67 (d, J=7.69 Hz, 1H), 5.64 (s, 2H), 3.43-3.50 (m, 4H), 2.87-2.94 (m, 4H), NH proton not detected $^{13}$C NMR (75 MHz, DMSO-d$_6$)δ158.7, 155.3 (d, J=271 Hz), 145.1, 136.5 (q, J=1.7 Hz), 134.5 (d, J=3.6 Hz) 132.6, 128.9, 127.2 (d, J=7.6 Hz), 121.2, 120.6 (q, J=271 Hz), 117.9, 117.6, 108.4, 103.1, 50.5, 46.9, 45.9

Compound A-3J: Tert-Butyl 4-(3-((3,4-Difluorobenzyl)Amino)-2-Nitrophenyl)Piperazine-1-Carboxylate

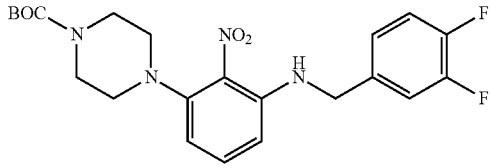 [SMILES: CC(C)(C)OC(=O)N1CCN(c2cccc(NCc3ccc(F)c(F)c3)c2[N+](=O)[O-])CC1]

To a 50 mL flask equipped with magnetic stirring bar, compound A-2A (1.10 g, 3.38 mmol) was added under argon atmosphere and flask was filled with dry DMSO (5 mL). Then, dried $K_2CO_3$ (0.7 g, 5.07 mmol) and 3,4-difluorobenzylamine (0.64 g, 3.72 mmol) were added, and the reaction mixture was heated to 70° C. and stirred for 24 h at this temperature. After that time, reaction mixture was cooled to a room temperature, poured into cold solution of brine (75 mL) and diluted with water (75 mL). The obtained precipitate was filtered off, washed with water, dried on air and crystalized from EtOH (99.9%, 10 mL) affording product A-3J as a yellowish solid (0.8 g, 53% yield) with 94.4% of purity, according to UPLCMS analysis (Method B).

Compound A-4J: Tert-Butyl 4-(2-Amino-3-((3,4-Difluorobenzyl)Amino)Phenylpiperazine-1-Carboxylate

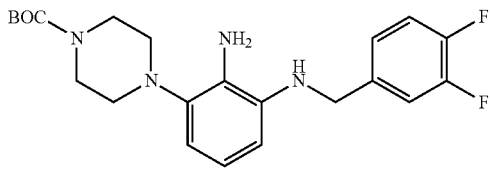 [SMILES: CC(C)(C)OC(=O)N1CCN(c2cccc(NCc3ccc(F)c(F)c3)c2N)CC1]

To a 100 mL flask equipped with magnetic stirring bar, compound A-3J (0.8 g, 1.78 mmol) and EtOH (25 mL) were added and the reaction mixture was heated to 80° C. Then, a freshly prepared solution of sodium dithionite (1.24 g, 7.14 mmol) in water (8 mL) was added within one minute. The reaction mixture was stirred for additional 15 minutes at 80° C. and then it was cooled to the room temperature. EtOH was removed and AcOEt (15 mL) was added. Phases were separated and the water phase was extracted once more with AcOEt (15 mL). Combined organic phases were washed with water, brine, dried under $MgSO_4$ and solvent was removed in vacuo. The crude product A-4J was obtained as a yellowish oil (0.400 g) and was used in the next step without further purification.

Compound A-5J, Compound 10: 1-(3,4-Difluorobenzyl)-4-(Piperazin-1-Yl)-2-(Trifluoromethyl)-1H-Benzo[d]Imidazole

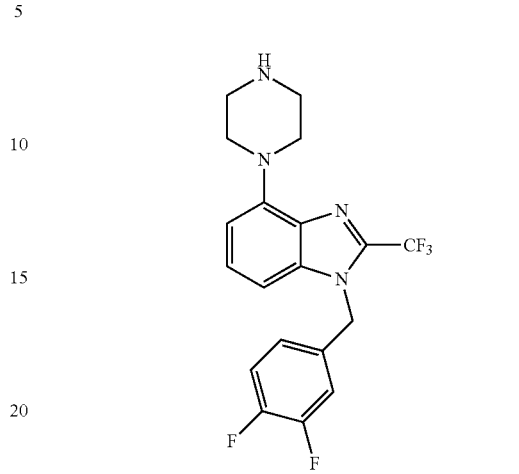

To a 10 mL flask equipped with magnetic stirring bar, compound A-4J (0.396 g, 1.0 mmol) and TFA (2.0 mL) were added and the reaction mixture was stirred at room temperature for 16 hours. After this time UPLCMS analysis showed full consumption of the substrate. The reaction mixture was cooled to room temperature and diluted with DCM (30 mL), and saturated solution of $NaHCO_3$ was added dropwise to achieve pH~8. Then, water and DCM were added and phases were separated. Water phase was extracted with DCM (2×20 mL) and combined organic phases were washed with water, brine, dried under $MgSO_4$ and solvent was removed in vacuo. The obtained crude product was purified using column chromatography (n-hexane/DCM/methanol/$NH_{3(aq)}$ 4.0/5.0/1.0/0.02, v/v/v/v) affording final product A-5J, Compound 10 as a yellow crystallizing oil (350 mg, 88% yield) with 95.01% of purity, according to UPLCMS analysis (Method B).

$^1$H NMR (300 MHz, DMSO-$d_6$)δ7.44-7.17 (m, 3H), 7.17-7.09 (m, 1H), 6.88-6.77 (m, 1H), 6.71 (d, J=7.7 Hz, 1H), 5.64 (s, 2H), 3.65-3.51 (m, 4H), 3.16-3.03 (m, 4H), NH protons not detected $^{13}$C NMR (75 MHz, DMSO-$d_6$)δ151.43 (dd, J=248 Hz and 12.7 Hz), 148.16 (dd, J=248 Hz and 12.8 Hz), 144.30, 137.4, 136.8 (q, J=38.2 Hz), 134.19 (dd, J=5.7, 3.6 Hz), 132.5, 127.2, 123.33 (q, J=3.4 Hz), 119.7 (q, J=271 Hz), 118.38 (d, J=17.5 Hz), 116.10 (d, J=18.0 Hz), 108.7, 103.8, 79.6, 48.8, 47.0, 44.7

Compound A-3K: Tert-Butyl 4-(3-((3,5-Dichlorobenzyl)Amino)-2-Nitrophenyl)Piperazine-1-Carboxylate

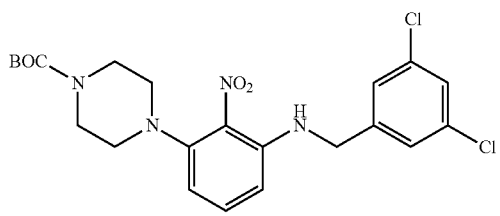 [SMILES: CC(C)(C)OC(=O)N1CCN(c2cccc(NCc3cc(Cl)cc(Cl)c3)c2[N+](=O)[O-])CC1]

To a 50 mL flask equipped with magnetic stirring bar, compound A-2A (0.9 g, 2.76 mmol) was added under argon atmosphere and flask was filled with dry DMSO (5 mL). Then, dried K₂CO₃ (0.95 g, 6.9 mmol) and 3,5-dichlorofluorobenzylamine (0.78 g, 4.43 mmol) were added, and the reaction mixture was heated to 70° C. and stirred for 24 h at this temperature. After that time, reaction mixture was cooled to a room temperature, poured into cold solution of brine (75 mL) and diluted with water (75 mL). The obtained precipitate was filtered off, washed with water, dried on air and crystalized from EtOH (99.9%, 10 mL) affording product A-3K as a yellowish solid (0.97 g, 78% yield) with 95% of purity, according to UPLCMS analysis (Method B).

Compound A-4K: Tert-Butyl 4-(2-Amino-3-((3,5-Dichlorobenzyl)Amino)Phenylpiperazine-1-Carboxylate

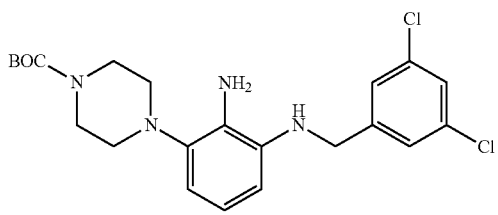 [SMILES: CC(C)(C)OC(=O)N1CCN(c2cccc(NCc3cc(Cl)cc(Cl)c3)c2N)CC1]

To a 100 mL flask equipped with magnetic stirring bar, compound A-3K (0.97 g, 2.16 mmol) and EtOH (30 mL) were added and the reaction mixture was heated to 80° C. Then, a freshly prepared solution of sodium dithionite (1.5 g, 8.66 mmol) in water (8 mL) was added within one minute. The reaction mixture was stirred for additional 15 minutes at 80° C. and then it was cooled to the room temperature. EtOH was removed and AcOEt (20 mL) was added. Phases were separated and the water phase was extracted once more with AcOEt (20 mL). Combined organic phases were washed with water, brine, dried under MgSO₄ and solvent was removed in vacuo. The crude product A-4K was obtained as a yellowish oil (0.890 g) and was used in the next step without further purification.

Compound A-5K, Compound 11: 1-(3,5-Dichlorobenzyl)-4-(Piperazin-1-Yl)-2-(Trifluoromethyl)-1H-Benzo[d]Imidazole

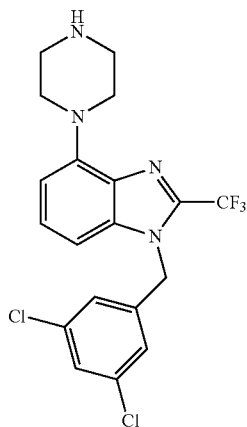 [SMILES: FC(F)(F)c1nc2c(N3CCNCC3)cccc2n1Cc1cc(Cl)cc(Cl)c1]

To a 10 mL flask equipped with magnetic stirring bar, compound A-4K (0.225 g, 0.538 mmol) and TFA (1.0 mL) were added and the reaction mixture was stirred at room temperature for 16 hours. After this time UPLCMS analysis showed full consumption of the substrate. The reaction mixture was cooled to room temperature and diluted with DCM (20 mL), and saturated solution of NaHCO₃ was added dropwise to achieve pH~8. Then, water and DCM were added and phases were separated. Water phase was extracted with DCM (2×10 mL) and combined organic phases were washed with water, brine, dried under MgSO₄ and solvent was removed in vacuo. The obtained crude product was purified using column chromatography (n-hexane/DCM/methanol/NH$_{3(aq)}$ 4.0/5.0/1.0/0.02, v/v/v/v) affording final product A-5K, Compound 11 as a yellow crystallizing oil (180 mg, 78% yield) with 95% of purity, according to UPLCMS analysis (Method B).

¹H NMR (300 MHz, CD₃OD) δ 7.33-7.25 (m, 1H), 6.97 (dd, J=0.6, 8.3 Hz, 1H), 6.89-6.80 (m, 1H), 6.77-6.72 (m, 1H), 6.62 (dd, J=2.2, 8.1 Hz, 2H), 5.60 (s, 2H), 3.56-3.49 (m, 5H), 3.08 (dd, J=4.1, 5.9 Hz, 5H), NH protons not detected ¹³C NMR (75 MHz, CD₃OD) δ 145.4, 137.3, 136.0 (q, J=1.7 Hz), 133.6, 132.4, 131.1, 129.1, 129.0, 127.1, 126.6, 126.3, 119.0 (q, J=271 Hz), 108.2, 102.1, 51.7, 46.3, 45.1

B. Compounds Based on Indole Core:

Compound B-2: N-(3-Bromo-2-Methylphenyl)-2,2,2-Trifluoroacetamide

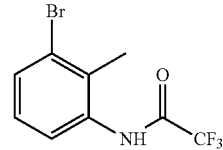

To a 250 mL flask equipped with magnetic stirring bar and filled with 150 ml DCM, 12.1 g (65 mmol) of 3-bromo 2-methylaniline was added. The reaction mixture was cooled to 0° C. and 16 ml (200 mmol) of pyridine was added, followed by dropping of 23 ml (165 mmol) of trifluoroacetic anhydride at this temperature. After addition the reaction was stirred 0.5 h at temperature <5° C., and 2.5 h at RT. After this time the reaction was quenched with 50 ml of NH₄Cl$_{sat}$ and diluted with 50 mL of water. Phases were separated and the water phase was extracted with DCM (2×100 mL). Combined organic phases were washed with water, brine and solvent was removed in vacuo. As a result, the product was obtained as the white solid (14.7 g, 80% yield) and was used in the next step without any further purification.

Compound B-3: N-[3-Bromo-2-(Bromomethyl)Phenyl]-2,2,2-Trifluoroacetamide

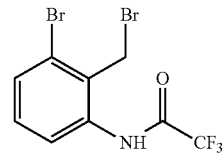 [SMILES: O=C(Nc1cccc(Br)c1CBr)C(F)(F)F]

250 mL flask equipped with magnetic stirring bar, condenser and spotlighted by 100 W lamp was filled with 120 ml CCl$_4$; 8.1 g (29 mmol) of B-2 and 0.38 g of benzoyl peroxide. The reaction mixture was heated to reflux and 2.1 ml of bromine in 10 mL CCl$_4$ was added in few portions by syringe. After addition reaction mixture was refluxed overnight. Next day TLC showed lack of substrate. Reaction was cooled, diluted with 120 ml DCM and poured to 100 ml 2M solution of sodium thiosulfate. Phases were separated and the water phase was extracted with DCM (2×60 mL). Combined organic phases were washed with water, brine and solvent was removed in vacuo. The residue was diluted with mixture of DCM:hexane 1:3, and product precipitated as white solid, 9.1 g, 88% yield.

Compound B-4:
4-Bromo-2-(Trifluoromethyl)-1H-Indole

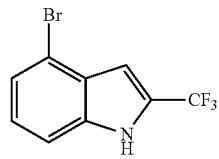 [SMILES: FC(F)(F)c1cc2c(Br)cccc2[nH]1]

500 mL flask equipped with magnetic stirring bar was filled with 200 ml of dry toluene and 20.1 g (56 mmol) of substrate B-3. Subsequently 15.9 g (61 mmol) of PPH$_3$ was added. Then the reaction mixture was heated to 60° C. and stirred for 2 hours. After this time reaction was cooled <5° C., and white solid was filtered, washed with Et$_2$O, and quick dried under air flow. Then, solid was refluxed with 250 mL DMF overnight—UPLC analysis showed end of reaction. Solvent was evaporated, residue diluted with 50 mL NaHCO$_3$aq and extracted 3 times with 50 ml ethyl acetate. Combined organic phases were washed with water, brine, dried with MgSO$_4$ and solvent was removed in vacuo. Raw product was chromatographed with mixture ethyl acetate:hexane 3:7 to give 13.5 g of oily product, yield 92%.

Compound B-5:
1-Benzyl-4-Bromo-2-(Trifluoromethyl)-1H-Indole

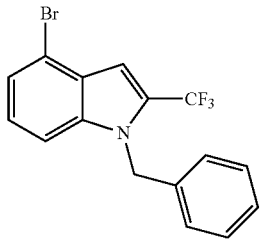 [SMILES: FC(F)(F)c1cc2c(Br)cccc2n1Cc1ccccc1]

250 mL flask equipped with magnetic stirring bar was filled with 80 ml dry DMF and 13.1 g (0.05 mol) of substrate B-4. Then the reaction mixture was cooled to 0° C. and 2.4 g (0.06 mol) of sodium hydride (60% in oil) was carefully added. 10 minutes after addition 5.95 ml (0.05 mol) of benzyl bromide was dropped at this temperature (0° C.). After addition of all reagents reaction was stirred 0.5 h at temperature <5° C., and 2.5 h at RT. After this time the reaction was quenched with 5 ml water and evaporated. Residue was diluted with water (100 mL) and extracted with DCM (3×70 mL). Combined organic phases were washed with water, brine, dried with MgSO$_4$ and evaporated. The product was obtained as white solid (17.5 g, ~100% yield) and was used in the next step without any further purification.

Compound B-6A: 1-Benzyl-4-(4-Methylpiperazin-1-Yl)-2-(Trifluoromethyl)-1H-Indole

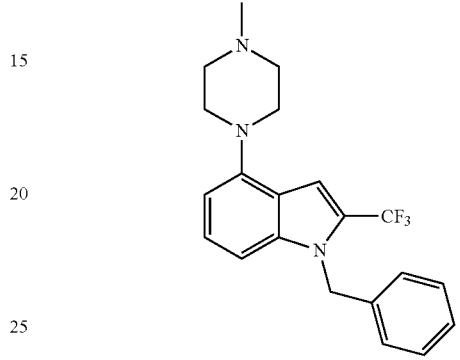

250 mL dry flask equipped with magnetic stirring bar, CaCl$_2$ tube and condenser was filled with 150 ml dry dioxane, 17.9 g (50 mmol, 1 eq) of substrate B-5, 5.64 ml (1 eq) of methylpiperazine, 1.4 g (0.03 eq) of Pd$_2$(dba)$_3$ and 33.6 g (2 eq) Cs$_2$CO$_3$. Flask was purged with argon thoroughly. Subsequently 2.24 g (0.07 eq) of BINAP was added and the reaction mixture was heated to 100° C. and stirred overnight. Next day the reaction mixture was cooled, poured on 200 ml water, filtered through cellite and extracted with DCM (3×100 mL). Combined organic phases were washed with water, brine, dried over MgSO$_4$ and solvent was removed in vacuo. The residue was chromatographed with mixture DCM:MeOH:NH$_3$ (500:19:1) to give 14 g of oily product B-6A, 75% yield.

Compound B-6B: Tert-Butyl 4-[1-Benzyl-2-(Trifluoromethyl)-1H-Indol-4-Yl]Piperazine-1-Carboxylate

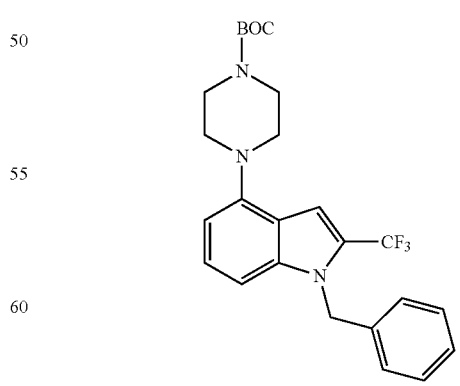

Compound B-6B was prepared, staring from B-5 (7.1 g, 20 mmol), according to the same procedure as for compound B-6A, using N-BOC-piperazine instead of methylpiperazine. After purification, 8.7 g of compound B-6B was obtained as a light brown solid (66% yield).

Compound B-7A: 4-(4-Methylpiperazin-1-Yl-2-(Trifluoromethyl)-1H-Indole

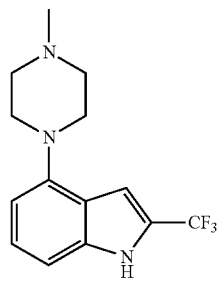 [SMILES: CN1CCN(c2cccc3[nH]c(C(F)(F)F)cc23)CC1]

500 mL flask equipped with magnetic stirring bar was filled with 70 ml of dry DMSO and 14 g (37.5 mmol) of substrate B-6A. Then the reaction mixture was cooled to 10° C. and 160 mL (160 mmol, 4.6 eq) of 1M t-BuOK in THF was added dropwise. Reaction mixture was cooled to around 2° C. and oxygen was bubbled through reaction mixture by glass pipe until full consumption of the substrate was observed (around 5 h, reaction temperature was maintained around 5° C.). After this time, reaction mixture was poured on water with ice (200 ml) and extracted with ethyl acetate (3×100 mL). Combined organic phases were washed with water, brine, dried over MgSO$_4$ and the solvent was evaporated. The residue was chromatographed with mixture DCM:MeOH (95:5), to give 6.5 g of product B-7A, 61% yield.

Compound B-7B: Tert-Butyl 4-[2-(Trifluoromethyl)-1H-Indol-4-Yl]Piperazine-1-Carboxylate

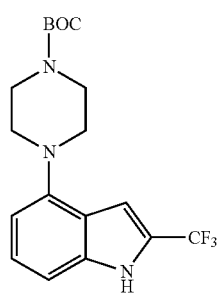 [SMILES: CC(C)(C)OC(=O)N1CCN(c2cccc3[nH]c(C(F)(F)F)cc23)CC1]

250 mL flask equipped with magnetic stirring bar was filled with 120 ml of dry THF, 45 ml of dry DMSO and 5.3 g (11.5 mmol) of substrate B-6B Then the reaction mixture was cooled to 0° C. and 12 g (107 mmol, 10 eq) of t-BuOK was added. Subsequently oxygen was bubbled through reaction mixture by glass pipe until full consumption of the substrate was observed (usually 2-4 h, reaction temperature was maintained around 5° C.). After this time, reaction mixture was poured on water with ice (200 ml) and extracted with ethyl acetate (3×70 mL). Combined organic phases were washed with water, brine, dried over MgSO$_4$ and the solvent was evaporated. The residue was chromatographed with mixture AcOEt:hexane (1:9), to give 3.8 g of product B-7B, 90% yield.

General Procedure a for the Preparation of Compounds B-8:

To a dried and filled with inert gas flask, indole B-7 (1 eq) and dry DMF (0.1M) were added, and the reaction mixture was cooled to 0° C. Sodium hydride (60% in mineral oil) (1.5 eq) was added and the reaction mixture was stirred 10 min at 0-5° C., and 1 h at room temperature. After this time the reaction was cooled to 0° C. and benzyl derivative (1.2 eq) was added dropwise. The reaction mixture was stirred at room temperature until the full consumption of the starting material. DCM and water were added and phases were separated. Water phase was extracted with DCM (3×10 mL) and combined organic phases were washed with water, dried over Na$_2$SO$_4$ and the solvent was removed in vacuo. The residue was purified by column chromatography.

Compound B-8B, Compound 13: 1-(3,4-Dichlorobenzyl)-4-(4-Methylpiperazin-1-Yl)-2-(Trifluoromethyl)-1H-Indole

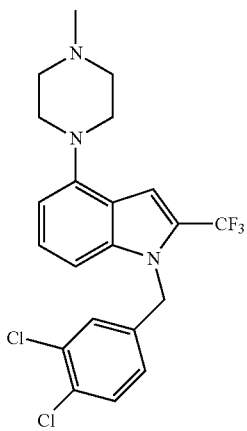 [SMILES: CN1CCN(c2cccc3c2cc(C(F)(F)F)n3Cc2ccc(Cl)c(Cl)c2)CC1]

Product B-8B, Compound 13 was obtained using general procedure A, starting from B-7A (50 mg, 0.17 mmol), as a light brown oil (29 mg, 37% yield, 97.72% of purity according to UPLCMS analysis).

Compound B-8C, Compound 14: 1-(4-Chloro-3-Fluorobenzyl)-4-(4-Methylpiperazin-1-Yl)-2-(Trifluoromethyl)-1H-Indole

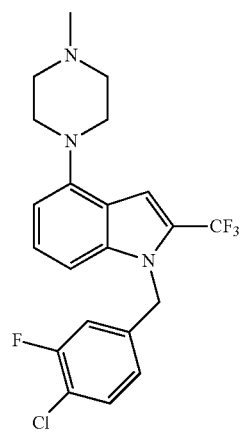 [SMILES: CN1CCN(c2cccc3c2cc(C(F)(F)F)n3Cc2ccc(Cl)c(F)c2)CC1]

Product B-8C, Compound 14 was obtained using general procedure A, starting from B-7A (50 mg, 0.17 mmol), as a light brown oil (37 mg, 49% yield, 96.5% of purity according to UPLCMS analysis).

Compound B-8D: Tert-Butyl 4-[1-(Thiazol-2-Ylm-ethyl-2-(Trifluoromethyl)Indol-4-Yl]Piperazine-1-Carboxylate

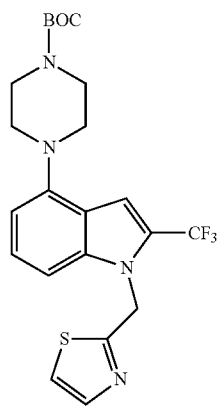 [SMILES: CC(C)(C)OC(=O)N1CCN(c2cccc3c2cc(C(F)(F)F)n3Cc2nccs2)CC1]

Product B-8D was obtained using general procedure A, starting from B-7B (63 mg, 0.17 mmol), as a light brown oil (36 mg, 45% yield).

Compound B-8E: Tert-Butyl 4-[1-[(4-Chloro-3-Fluoro-Phenyl)Methyl]-2-(Trifluoromethyl)Indol-4-Yl]Piperazine-1-Carboxylate

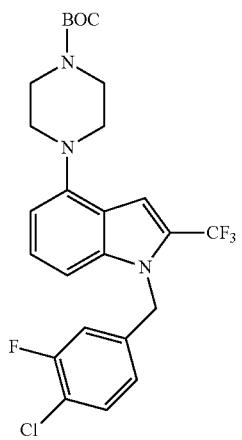 [SMILES: CC(C)(C)OC(=O)N1CCN(c2cccc3c2cc(C(F)(F)F)n3Cc2ccc(Cl)c(F)c2)CC1]

Product B-8E was obtained using general procedure A, starting from B-7B (63 mg, 0.17 mmol), as a light brown oil (46 mg, 53% yield).

Compound B-8F: Tert-Butyl 4-[1-(Furan-2-Ylm-ethyl)-2-(Trifluoromethyl)-1H-Indol-4-Yl]Pipera-zine-1-Carboxylate

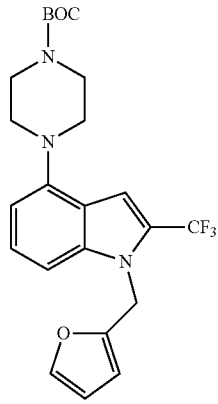 [SMILES: CC(C)(C)OC(=O)N1CCN(c2cccc3c2cc(C(F)(F)F)n3Cc2ccco2)CC1]

Sodium hydride (22 mg, 60% in mineral oil, 0.54 mmol) was added to the solution of B-7B (200 mg, 0.54 mmol) in dry DMF under argon at room temperature. Reaction mixture was stirred for 30 min and then 2-(Bromomethyl)furan (105 mg, 0.65 mmol) was added. After 1 h next portions of sodium hydride (22 mg, 60% in mineral oil, 0.54 mmol) and 2-(Bromomethyl)furan (31 mg, 0.19 mmol) were added and reaction was continued for 2 h. The reaction mixture was poured into water (20 mL) and extracted with DCM (2×20 mL). Combined extracts were washed with brine, dried over MgSO$_4$ and evaporated under reduced pressure. Crude product was purified by column chromatography (AcOEt/hexane, 7/93 v/v). As a result, the final product B-8F was obtained as grey solid (170 mg, 70% yield).

Compound B-8G: 1-(3-Methoxybenzyl)-4-(Piper-azin-1-Yl)-2-(Trifluoromethyl)-1H-Indole

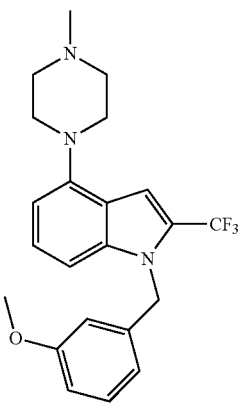 [SMILES: COc1cccc(Cn2c(C(F)(F)F)cc3c(N4CCN(C)CC4)cccc32)c1]

Product B-8G was obtained using general procedure A, starting from B-7A (100 mg, 0.35 mmol), as a light brown oil (89 mg, 63% yield, 96% of purity according to UPLCMS analysis).

Compound B-8H, Compound 19: 1-(3-Fluorobenzyl)-4-(Piperazin-1-Yl)-2-(Trifluoromethyl)-1H-Indole

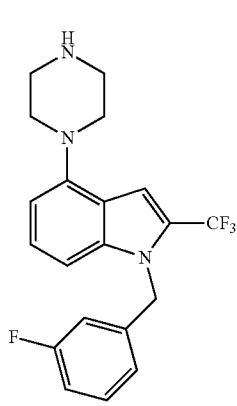 [SMILES: Fc1cccc(Cn2c(C(F)(F)F)cc3c(N4CCNCC4)cccc32)c1]

Product B-8H, Compound 19 was obtained using general procedure A, starting from B-7B (100 mg, 0.27 mmol), followed by deprotection of BOC-group with 200 µl TFA in 1 ml DCM at RT to give 58 mg of solid, 57% yield, 99% of purity according to UPLCMS analysis.

Compound B-8I: Tert-Butyl 4-[1-(3-Chlorobenzyl)-2-(Trifluoromethyl)-1H-Indol-4-Yl]Piperazine-1-Carboxylate

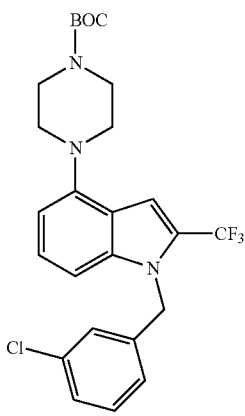 [SMILES: CC(C)(C)OC(=O)N1CCN(c2cccc3c2cc(C(F)(F)F)n3Cc2cccc(Cl)c2)CC1]

Product B-8I was obtained using general procedure A, starting from B-7B (150 mg, 0.41 mmol), as an yellow oil (190 mg, 94% yield, 98.5 of purity according to UPLCMS analysis).

Compound B-8J, Compound 21: 1-(Furan-2-Ylmethyl)-4-(4-Methylpiperazin-1-Yl)-2-(Trifluoromethyl)-1H-Indole

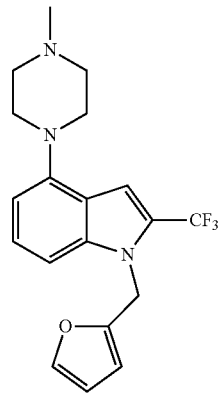 [SMILES: CN1CCN(c2cccc3c2cc(C(F)(F)F)n3Cc2ccco2)CC1]

Sodium hydride (16 mg, 60% in mineral oil, 0.40 mmol) was added to the solution of B-7A (100 mg, 0.37 mmol) in dry DMF under argon at room temperature. Reaction mixture was stirred for 30 min and then 2-(Bromomethyl)furan (64 mg, 0.40 mmol) was added. After 18 h next portions of sodium hydride (16 mg, 60% in mineral oil, 0.40 mmol) and 2-(Bromomethyl)furan (64 mg, 0.40 mmol) were added and the reaction was continued for 2 h. The reaction mixture was poured into water (20 mL) and extracted with ethyl acetate (2×20 mL). Combined extracts were washed with brine, dried over MgSO$_4$ and evaporated under reduced pressure. Crude product was purified by column chromatography (DCM/MeOH/NH3aq., 98/2/0.5 v/v/v) and next by preparative HPLC. As a result, the final product B-8J, Compound 21 was obtained as light yellow oil (22 mg, 16%, 99.7% of purity according to UPLCMS analysis).

$^1$H NMR (500 MHz, DMSO-d$_6$) δ 7.55 (m, 1H), 7.32 (d, J=8.4 Hz, 1H), 7.24 (dd, J=8.2, 7.8 Hz, 1H), 7.04 (s, 1H), 6.61 (d, J=7.6 Hz, 1H), 6.38 (m, 2H), 5.46 (s, 2H), 3.12 (m, 4H), 2.54 (m, 4H), 2.25 (s, 3H).

Compound B-8K, Compound 22: 1-(3,4-Difluorobenzyl)-4-(4-Methylpiperazin-1-Yl)-2-(Trifluoromethyl)-1H-Indole

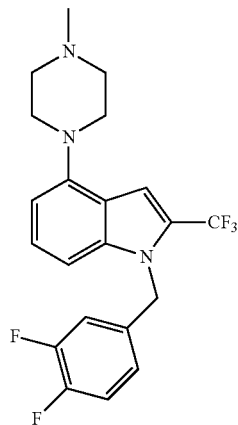 [SMILES: CN1CCN(c2cccc3c2cc(C(F)(F)F)n3Cc2ccc(F)c(F)c2)CC1]

Product B-8K, Compound 22 was obtained using general procedure A, starting from B-7A (100 mg, 0.37 mmol). Crude product was purified by column chromatography (DCM/MeOH/NH$_{3aq.}$, 98/2/0.5 v/v/v) and next by preparative TLC. As a result, the final product was obtained as light yellow oil (40 mg, 13% yield, 94.7% of purity according to UPLCMS analysis).

$^1$H NMR (500 MHz, DMSO-d$_6$)δ7.34 (m, 1H), 7.21 (dd, J=8.5, 7.6 Hz, 1H), 7.14 (s, 1H), 7.08 (d, J=8.4 Hz, 1H), 7.06 (m, 1H), 6.66 (m, 1H), 6.62 (d, J=7.6 Hz, 1H), 5.54 (s, 2H), 3.17 (m, 4H), 2.56 (m, 4H), 2.26 (s, 3H).

Compound B-8L: Tert-Butyl 4-[1-(3-Methoxybenzyl)-2-(Trifluoromethyl-1H-Indol-4-Yl]Piperazine-1-Carboxylate

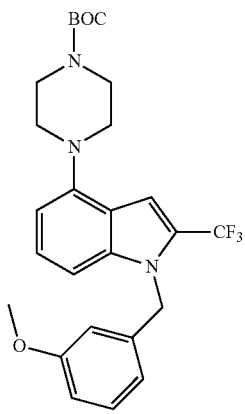 [SMILES: COc1cccc(Cn2c(C(F)(F)F)cc3c(N4CCN(C(=O)OC(C)(C)C)CC4)cccc32)c1]

Product B-8L was obtained using general procedure A, starting from B-7B (150 mg, 0.41 mmol), as an yellow oil (180 mg, 90% yield, 99.5% of purity according to UPLCMS analysis).

Compound B-8M: 1-(3-Fluorobenzyl)-4-(4-Methylpiperazin-1-Yl)-2-(Trifluoromethyl)-1H-Indole

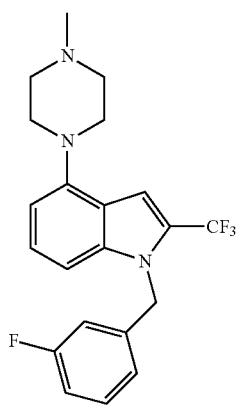 [SMILES: CN1CCN(c2cccc3c2cc(C(F)(F)F)n3Cc2cccc(F)c2)CC1]

Product B-8M was obtained using general procedure A, starting from B-7A (100 mg, 0.35 mmol), as a light brown oil (97 mg, 71% yield, 96% of purity according to UPLCMS analysis).

Compound B-8N: Tert-Butyl 4-[1-(3,4-Difluorobenzyl)-2-(Trifluoromethyl)-1H-Indol-4-Yl]Piperazine-1-Carboxylate

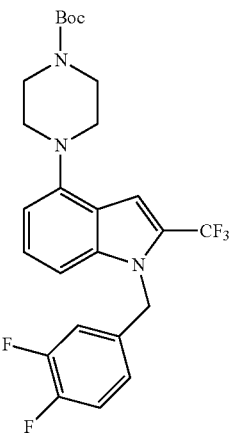 [SMILES: CC(C)(C)OC(=O)N1CCN(c2cccc3c2cc(C(F)(F)F)n3Cc2ccc(F)c(F)c2)CC1]

Product B-8N was obtained using general procedure A, starting from B-7B (200 mg, 0.54 mmol), as colorless oil (210 mg, 78% yield).

Compound B-8P: 1-(3-Chlorobenzyl)-4-(4-Methylpiperazin-1-Yl)-2-(Trifluoromethyl)-1H-Indole

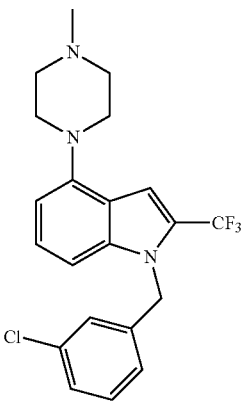 [SMILES: CN1CCN(c2cccc3c2cc(C(F)(F)F)n3Cc2cccc(Cl)c2)CC1]

Product B-8P was obtained using general procedure A, starting from B-7A (100 mg, 0.35 mmol), as a light yellow oil (74 mg, 52% yield, 98% of purity according to UPLCMS analysis).

Compound B-8S: Tert-Butyl 4-[1-(Thiophen-2-Ylmethyl)-2-(Trifluoromethyl)-1H-Indol-4-Yl]Piperazine-1-Carboxylate

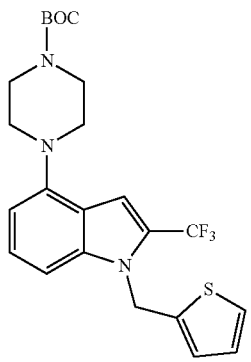 [SMILES: CC(C)(C)OC(=O)N1CCN(c2cccc3c2cc(C(F)(F)F)n3Cc2cccs2)CC1]

Compound B-8S was obtained using general procedure A (mesylate was used instead of bromide, 1.5 eq, 16 h at 60° C.), starting from B-7B (507 mg, 1.37 mmol), as a light brown solid (420 mg, 65% yield, 95% of purity according to UPLCMS analysis).

Compound B-8T: Tert-Butyl 4-[1-(Thiophen-3-Yl-methyl)-2-(Trifluoromethyl)-1H-Indol-4-Yl]Piperazine-1-Carboxylate

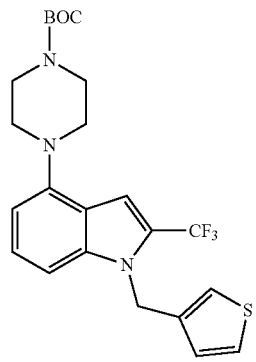 [SMILES: CC(C)(C)OC(=O)N1CCN(c2cccc3c2cc(C(F)(F)F)n3Cc2ccsc2)CC1]

Compound B-8T was obtained using general procedure A (mesylate was used instead of bromide, 3 eq, 16 h at 60° C.), starting from B-7B (500 mg, 1.35 mmol), as a light brown solid (250 mg, 40% yield, 95% of purity according to UPLCMS analysis.

Compound B-1V, Compound 34: 4-(4-Methylpiperazin-1-Yl)-1-[(5-Methyl-1,3-Thiazol-2-Yl)Methyl]-2-(Trifluoromethyl-1H-Indole

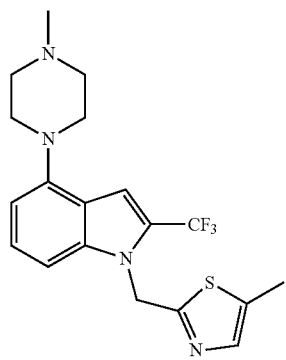 [SMILES: Cc1cnc(Cn2c(C(F)(F)F)cc3c(N4CCN(C)CC4)cccc32)s1]

Compound B-8V, Compound 34 was obtained using general procedure A, starting from B-7B (142 mg, 0.5 mmol), as an amorphous solid (120 mg, 61% yield, 99.7% of purity according to UPLCMS analysis.

General Procedure B for the Preparation of Compounds B-8 and B-9:

To a dried and filled with inert gas flask, indole B-7 (1 eq) and dry THF (0.1M) were added, and the reaction mixture was cooled to 0° C. (5-Methyl-2-furyl)methanol (2 eq), triphenylphosphine (1.5 eq) and DIAD (1.5 eq) were added and the reaction mixture was stirred 10 min at 0-5° C., and 1 h at room temperature. DCM and water were added and phases were separated. Water phase was extracted with DCM (3×10 mL) and combined organic phases were washed with water, dried over $Na_2SO_4$ and the solvent was removed in vacuo. The residue was purified by column chromatography and preparative HPLC.

Compound B-9Q, Compound 28: 1-[(5-Methyl-furan-2-Yl)Methyl]-4-(Piperazin-1-Yl)-2-(Trifluoromethyl)-1H-Indole

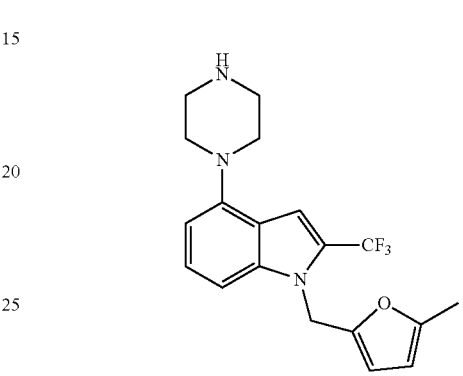

Compound B-9Q, Compound 28 was obtained using general procedure B, starting from B-7B (184 mg, 0.5 mmol) followed by deprotection of BOC-group with 200 µl of TFA in 1 ml DCM at RT, as an amorphous solid (16 mg, 9% yield, 99% of purity according to UPLCMS analysis).

Compound B-9R, Compound 29: 1-[(5-Methylthiophen-2-Yl)Methyl]-4-(Piperazin-1-Yl)-2-(Trifluoromethyl)-1H-Indole

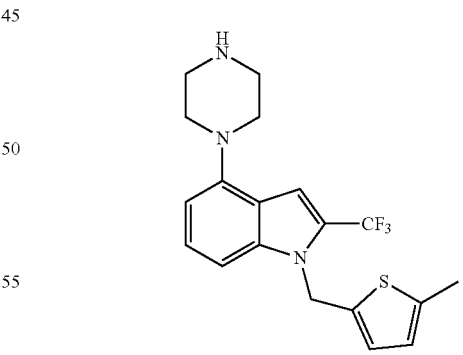

Compound B-9R, Compound 29 was obtained using general procedure B, starting from B-7B (184 mg, 0.5 mmol) followed by deprotection of BOC-group with 400 µl of TFA in 4 ml DCM at RT, as an light brown solid (22 mg, 12% yield, 96.6% of purity according to UPLCMS analysis).

Compound B-9F, Compound 17: 1-(Furan-2-Ylmethyl)-4-(Piperazin-1-Yl)-2-(Trifluoromethyl)-1H-Indole

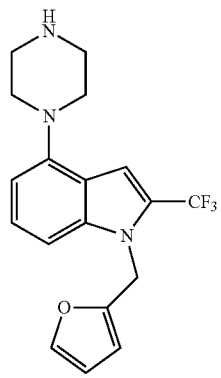 [SMILES: FC(F)(F)c1cc2c(N3CCNCC3)cccc2n1Cc1ccco1]

The trifluoroacetic acid (2 mL) was added to the stirred solution of compound B-8F (170 mg, 0.38 mmol) in 5 ml of DCM at 0° C. The resulting mixture was stirred for 2 h then it was concentrated under reduced pressure. The residue was dissolved in 30 ml of DCM, washed with saturated NaHCO$_3$ (2×20 mL), brine (20 mL) and dried over MgSO$_4$. The solvent was removed in vacuo and the crude product was purified by column chromatography (DCM/MeOH/NH$_3$.q., 95/5/0.5 v/v/v). As a result, the final product B-9F, Compound 17 was obtained as light yellow oil (41 mg, 31% yield, 98.9% of purity according to UPLCMS analysis).

$^1$H NMR (500 MHz, DMSO-d$_6$) δ 7.58 (m, 1H), 7.35 (d, J=8.4 Hz, 1H), 7.27 (dd, J=8.2, 7.8 Hz, 1H), 7.07 (s, 1H), 6.63 (d, J=7.6 Hz, 1H), 6.41 (m, 2H), 5.50 (s, 2H), 3.07 (m, 4H), 2.95 (m, 4H).

Compound B-9N, Compound 25: 1-(3,4-Difluorobenzyl)-4-(Piperazin-1-Yl)-2-(Trifluoromethyl)-1H-Indole

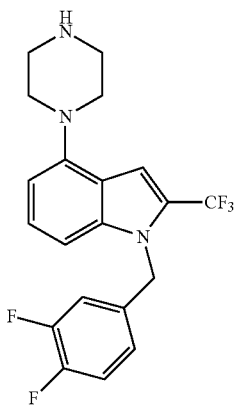 [SMILES: Fc1ccc(Cn2c(C(F)(F)F)cc3c(N4CCNCC4)cccc32)cc1F]

4M solution of HCl in dioxane (1.0 mL) was added dropwise to a stirred solution of B-8N (105 mg, 0.26 mmol) in 3 ml of THF. The reaction mixture was stirred at room temperature for 2 h, then 2 mL of Et$_2$O was added and the reaction was stirred additionally for 0.5 h. The white solid was filtered, washed with Et$_2$O (2×5 mL) and dried under vacuum. Solid was suspended in 20 ml of AcOEt, 1M NaOH (10 mL) was added and the mixture was vigorously stirred for 10 min. Organic phase was separated, washed with brine and dried over MgSO$_4$. The solvent was removed in vacuo and the crude product was purified by column chromatography (DCM/MeOH/NH$_{3aq.}$, 93/7/0.5 v/v/v). As a result, the final product B-9N, Compound 25 was obtained as light yellow oil (40 mg, 39% yield, 96.7% of purity according to UPLCMS analysis).

$^1$H NMR (500 MHz, CDCl$_3$) δ 7.21 (m, 1H), 7.09-7.04 (m, 1H), 7.02 (s, 1H), 6.85 (d, J=8.3 Hz, 1H), 6.81-6.73 (m, 2H), 6.67 (d, J=7.7 Hz, 1H), 5.39 (s, 2H), 3.31 (m, 4H), 3.23 (m, 4H).

General Procedure C for the Preparation of Compounds B-9:

To a 25 mL flask compound B-8 was added followed by THF (5 mL) and 4M HCl in dioxane (0.5 mL). The reaction mixture was stirred at room temperature until the full consumption of the starting material, then 10 mL of Et$_2$O was added and the reaction was stirred additionally for 0.5 h. The white solid was filtered, washed with Et$_2$O (2×10 mL) and dried under vacuum.

Compound B-9D, Compound 15: 4-(Piperazin-1-Yl)-1-(1,3-Thiazol-2-Ylmethyl)-2-(Trifluoromethyl)-1H-Indole, in Form of Hydrochloride Salt

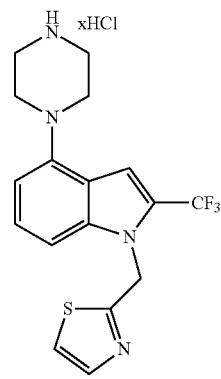

Product B-9D, Compound 15 in form of hydrochloride salt was obtained using general procedure C, starting from B-8D (36 mg, 0.08 mmol), as a white solid (19 mg, 61% yield, 99% of purity according to UPLCMS analysis)

Compound B-9E, Compound 16: 1-(4-Chloro-3-Fluorobenzyl-4-(Piperazin-1-Yl)-2-(Trifluoromethyl)-1H-Indole, in Form of Hydrochloride Salt

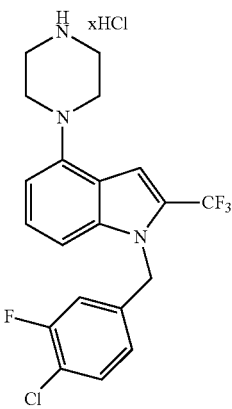

Product B-9E, Compound 16 in form of hydrochloride salt was obtained using general procedure C, starting from B-8E (46 mg, 0.09 mmol), as a white solid (9 mg, 22% yield, 98% of purity according to UPLCMS analysis)

Compound B-9G. Compound 18: 1-(3-Methoxybenzyl)-4-(4-Methylpiperazin-1-Yl)-2-(Trifluoromethyl)-1H-Indole in Form of Hydrochloride Salt

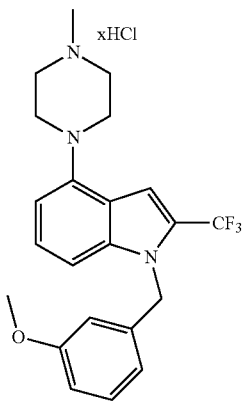 [SMILES: COc1cccc(Cn2c(C(F)(F)F)cc3c(N4CCN(C)CC4)cccc32)c1]

Product B-9G, Compound 18 in form of hydrochloride salt was obtained using general procedure C, starting from B-8G (89 mg, 0.22 mmol), as a white solid (92 mg, 92% yield, 99.5% of purity according to UPLCMS analysis).

$^1$H NMR (500 MHz, DMSO-$d_6$)δ11.22 (br s, 1H), 7.30 (s, 1H), 7.26-7.11 (m, 3H), 6.81 (dd, J=8.1, 2.5 Hz, 1H), 6.69 (d, J=7.5 Hz, 1H), 6.54 (m, 1H), 6.45 (d, J=7.6 Hz, 1H), 5.52 (s, 2H), 3.71 (d, J=12.7 Hz, 2H), 3.51 (d, J=11.8 Hz, 2H), 3.38-3.27 (m, 2H), 3.27-3.17 (m, 2H), 2.84 (d, J=4.7 Hz, 3H).

Compound B-9I, Compound 20: 1-(3-Chlorobenzyl)-4-(Piperazin-1-Yl)-2-(Trifluoromethyl)-1H-Indole, in Form of Hydrochloride Salt

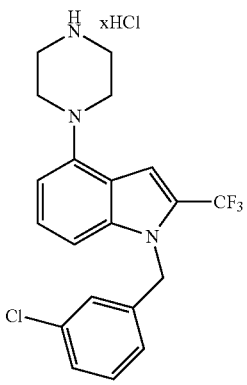 [SMILES: FC(F)(F)c1cc2c(N3CCNCC3)cccc2n1Cc1cccc(Cl)c1]

Product B-9I, Compound 20 in form of hydrochloride salt was obtained using general procedure C (2.5 mL of 4M HCl for 24 h), starting from B-8I (190 mg, 0.39 mmol), as a white solid (137 mg, 82% yield, 97.8% of purity according to UPLCMS analysis).

$^1$H NMR (500 MHz, DMSO-$d_6$)δ9.55 (br s, 2H), 7.38 (s, 1H), 7.34-7.29 (m, 2H), 7.25 (m, 1H), 7.18 (d, J=8.4 Hz, 1H), 7.04 (d, J=2.0 Hz, 1H), 6.82 (ddd, J=5.8, 3.0, 1.9 Hz, 1H), 6.71 (d, J=7.6 Hz, 1H), 5.59 (s, 2H), 3.46-3.25 (m, 8H).

Compound B-9L, Compound 23: 1-(3-Methoxybenzyl)-4-(Piperazin-1-Yl)-2-(Trifluoromethyl)-1H-Indole, in Form of Hydrochloride Salt

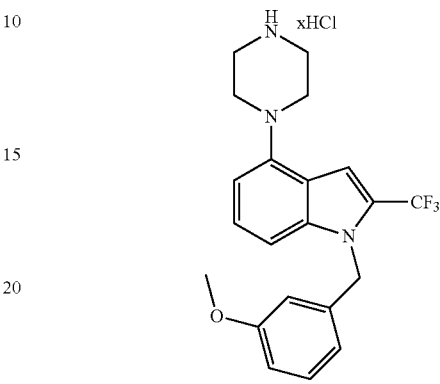

Product B-9L, Compound 23 in form of hydrochloride salt was obtained using general procedure C (2.5 mL of 4M HCl for 24 h), starting from B-8L (180 mg, 0.37 mmol), as a white solid (126 mg, 81% yield, 98.7% of purity according to UPLCMS analysis).

$^1$H NMR (500 MHz, DMSO-$d_6$)δ9.53 (br s, 2H), 7.34 (s, 1H), 7.25-7.12 (m, 3H), 6.81 (dd, J=8.0, 2.5 Hz, 1H), 6.69 (d, J=7.6 Hz, 1H), 6.54 (br s, 1H), 6.45 (d, J=7.6 Hz, 1H), 5.52 (s, 2H), 3.67 (s, 3H), 3.40 (m, 4H), 3.32 (m, 4H).

Compound B-9M, Compound 24: 1-[(3-Fluorophenyl)Methyl]-4-(4-Methylpiperazin-1-Yl)-2-(Trifluoromethyl)-1H-Indole, in Form of Hydrochloride Salt

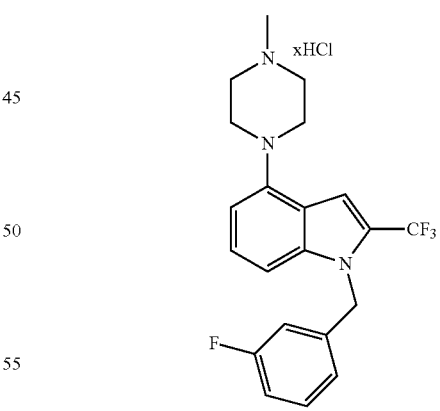

Product B-9M, Compound 24 in form of hydrochloride salt was obtained using general procedure C, starting from B-8M (97 mg, 0.25 mmol), as a white solid (102 mg, 92% yield, 99.2% of purity according to UPLCMS analysis).

$^1$H NMR (500 MHz, DMSO-$d_6$)δ11.30 (br s, 1H), 7.37-7.28 (m, 2H), 7.28-7.21 (m, 1H), 7.18 (d, J=8.5 Hz, 1H), 7.08 (td, J=8.7, 2.6 Hz, 1H), 6.77 (dt, J=10.1, 2.0 Hz, 1H), 6.71 (dd, J=7.9, 5.8 Hz, 2H), 5.59 (s, 2H), 3.72 (d, J=12.5 Hz, 2H), 3.52 (d, J=11.7 Hz, 2H), 3.39-3.19 (m, 4H), 2.84 (d, J=4.7 Hz, 3H).

Compound B-9P, Compound 27: 1-(3-Chlorobenzyl)-4-(4-Methylpiperazin-1-Yl)-2-(Trifluoromethyl)-1H-Indole, in Form of Hydrochloride Salt

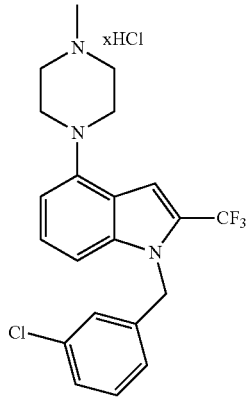 [SMILES: CN1CCN(c2cccc3c2cc(C(F)(F)F)n3Cc2cccc(Cl)c2)CC1]

Product B-9P, Compound 27 in form of hydrochloride salt was obtained using general procedure C, starting from B-8P (74 mg, 0.18 mmol), as a white solid (80 mg, 99% yield, 97.95% of purity according to UPLCMS analysis).

$^1$H-NMR (500 MHz, DMSO-d$_6$)δ11.39 (br s, 1H), 7.35-7.29 (m, 3H), 7.28-7.23 (m, 1H), 7.18 (d, J=8.4 Hz, 1H), 7.04 (q, J=1.3 Hz, 1H), 6.82 (ddd, J=5.6, 3.5, 1.7 Hz, 1H), 6.71 (d, J=7.6 Hz, 1H), 5.59 (s, 2H), 3.76-3.68 (m, 2H), 3.52 (d, J=11.7 Hz, 2H), 3.39-3.19 (m, 4H), 2.84 (d, J=4.7 Hz, 3H).

General Procedure D for the Preparation of Compounds B-9:

To a 25 mL flask compound B-8 was added followed by dioxane (10 mL) and concentrated HCl (1 mL). The reaction mixture was stirred at 60° C. for 10 minutes. The solvent was evaporated and the residue was recrystallized from i-PrOH. The solid was filtered, washed with i-PrOH (2×5 mL) and dried under vacuum.

Compound B-9S, Compound 30: 4-(Piperazin-1-Yl)-1-(Thiophen-2-Ylmethyl)-2-(Trifluoromethyl)-1H-Indole, in Form of Hydrochloride Salt

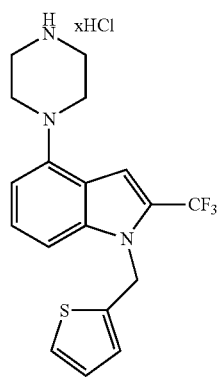 [SMILES: FC(F)(F)c1cc2c(N3CCNCC3)cccc2n1Cc1cccs1]

Product B-9S, Compound 30 in form of hydrochloride salt was obtained using general procedure D, starting from B-8S (420 mg, 0.90 mmol), as a light brown solid (180 mg, 40% yield, 95% of purity according to UPLCMS analysis).

Compound B-9T, Compound 31: 4-(Piperazin-1-Yl)-1-(Thiophen-3-Ylmethyl)-2-(Trifluoromethyl)-1H-Indole, in Form of Hydrochloride Salt

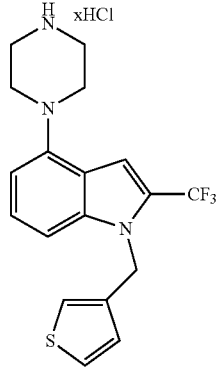 [SMILES: FC(F)(F)c1cc2c(N3CCNCC3)cccc2n1Cc1ccsc1]

Product B-9T, Compound 31 in form of hydrochloride salt was obtained using general procedure D, starting from B-8T (250 mg, 0.54 mmol), as a light brown solid (130 mg, 48% yield, 96.7% of purity according to UPLCMS analysis).

Compound B-9U, Compound 32: 4-(4-Methylpiperazin-1-Yl)-1-(Thiophen-3-Ylmethyl)-2-(Trifluoromethyl)-1H-Indole, in Form of Hydrochloride Salt

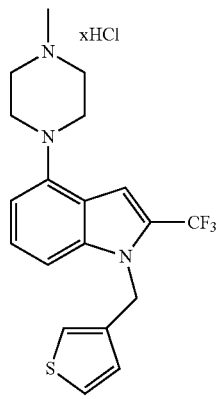 [SMILES: CN1CCN(c2cccc3c2cc(C(F)(F)F)n3Cc2ccsc2)CC1]

To a round bottom flask compound B-9T (250 mg, 0.62 mmol) was added followed by MeOH (5.5 mL), AcOH (40 μl) and formaldehyde (600 μL, 37% water solution). The reaction mixture was stirred at 40° C. for 0.5 h and after this time all solvents were evaporated. The residue was dissolved in dioxane (10 mL) and concentrated HCl (1 mL). The reaction mixture was stirred at 60° C. for 10 minutes. The solvent was evaporated and the residue was recrystallized from i-PrOH. The solid was filtered, washed with i-PrOH (2×5 mL) and dried under vacuum. As a result, compound B-9U, Compound 32 in form of hydrochloride salt was obtained as a light brown solid (48 mg, 19% yield, 95% of purity according to UPLCMS analysis).

Compound B-9W, Compound 33: 4-(4-Methylpiperazin-1-Yl)-1-(Thiophen-2-Ylmethyl)-2-(Trifluoromethyl)-1H-Indole, in Form of Hydrochloride Salt

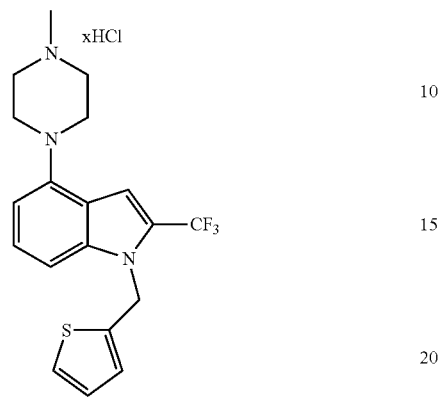

Product B-9W, Compound 33 in form of hydrochloride salt was obtained using the same amount of reagents as for compound B-9U. As a result, product B-9W, Compound 33 was obtained, starting from B-95 (65 mg, 0.16 mmol), as a light brown solid (39 mg, 59% yield, 99% of purity according to UPLCMS analysis).

The following examples have been synthesized according to described procedures herein or known literature methods using the appropriate starting materials and methods known to the skilled person in the art:

| ADN | Cpd No | Structure | Name | Analytical Data |
|---|---|---|---|---|
| 4174 | 1 | 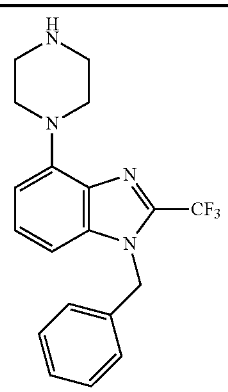 | 1-benzyl-4-(piperazin-1-yl)-2-(trifluoromethyl)-1H-benzimidazole* | Method A (analysis in basic gradient): 99.24%, 361.2 [M + H]$^+$, retention time: 2.08 min.; |
| 4182 | 2 | 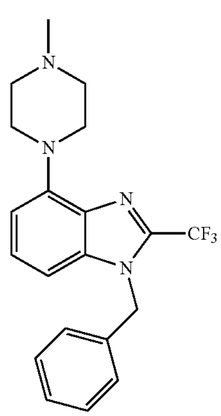 [SMILES: CN1CCN(c2cccc3c2nc(C(F)(F)F)n3Cc2ccccc2)CC1] | 1-benzyl-4-(4-methylpiperazin-1-yl)-2-(trifluoromethyl)-1H-benzimidazole* | Method A (analysis in basic gradient): 98.09%, 375.2 [M + H]$^+$, retention time: 3.69 min.; |

-continued

| ADN | Cpd No | Structure | Name | Analytical Data |
|---|---|---|---|---|
| 4183 | 3 | 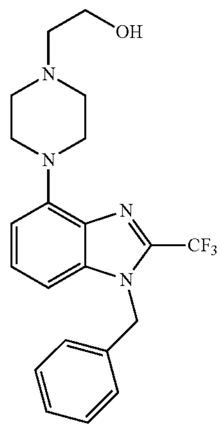 [SMILES: OCCN1CCN(c2cccc3c2nc(C(F)(F)F)n3Cc2ccccc2)CC1] | 2-{4-[1-benzyl-2-(trifluoromethyl)-1H-benzimidazol-4-yl]piperazin-1-yl}ethanol* | Method A (analysis in basic gradient): 96.95%, 405.3 [M + H]+, retention time: 1.78 min.; |
| 4281 | 4 | 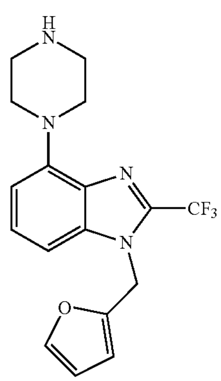 [SMILES: FC(F)(F)c1nc2c(N3CCNCC3)cccc2n1Cc1ccco1] | 1-(furan-2-ylmethyl)-4-(piperazin-1-yl)-2-(trifluoromethyl)-1H-benzimidazole | Method A (analysis in basic gradient): 97.34%, 350.8 [M + H]+, retention time: 3.55 min.; |
| 4282 | 5 | 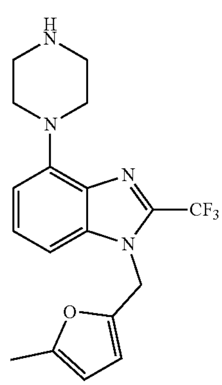 | 1-[(5-methylfuran-2-yl)methyl]-4-(piperazin-1-yl)-2-(trifluoromethyl)-1H-benzimidazole | Method A (analysis in basic gradient): 96.72%, 364.7 [M + H]+, retention time: 3.86 min.; |

-continued

| ADN | Cpd No | Structure | Name | Analytical Data |
|---|---|---|---|---|
| 4185 | 6 | 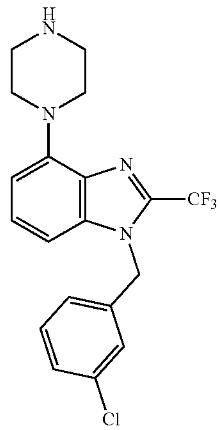 [SMILES: FC(F)(F)c1nc2c(N3CCNCC3)cccc2n1Cc1cccc(Cl)c1] | 1-(3-chlorobenzyl)-4-(piperazin-1-yl)-2-(trifluoromethyl)-1H-benzimidazole* | Method B (UPLC-MS): 100%, 395.1 [M + H]$^+$, retention time: 5.29 min.; |
| 4189 | 7 | 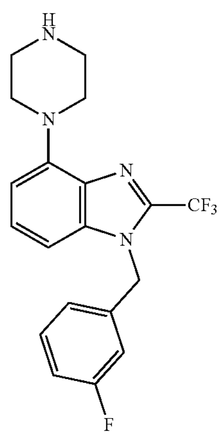 [SMILES: Fc1cccc(Cn2c(C(F)(F)F)nc3c(N4CCNCC4)cccc32)c1] | 1-(3-fluorobenzyl)-4-(piperazin-1-yl)-2-(trifluoromethyl)-1H-benzimidazole* | Method B (UPLC-MS): 98.84%, 379.1 [M + H]$^+$, retention time: 4.92 min.; |
| 4209 | 8 | 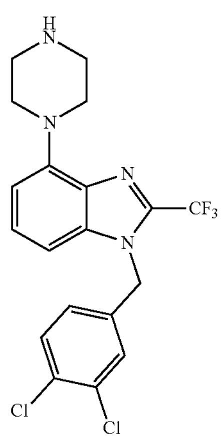 [SMILES: FC(F)(F)c1nc2c(N3CCNCC3)cccc2n1Cc1ccc(Cl)c(Cl)c1] | 1-(3,4-dichlorobenzyl)-4-(piperazin-1-yl)-2-(trifluoromethyl)-1H-benzo[d]imidazole | Method B (UPLC-MS): 93.00%, 428.99 [M + H]$^+$, retention time: 5.82 min.; |

-continued

| ADN | Cpd No | Structure | Name | Analytical Data |
|---|---|---|---|---|
| 4202 | 9 | 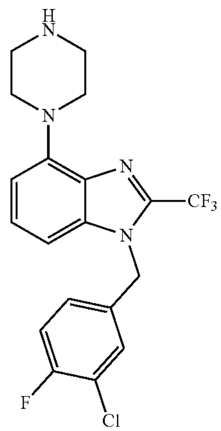 [SMILES: Fc1ccc(Cn2c(C(F)(F)F)nc3c(N4CCNCC4)cccc32)cc1Cl] | 1-(3-chioro-4-fluorobenzyl)-4-(piperazin-1-yl)-2-(trifluoromethyl)-1H-benzo[d]imidazole | Method B (UPLC-MS): 97.50%, 413.04 [M + H]$^+$, retention time: 5.39 min.; |
| 4203 | 10 | 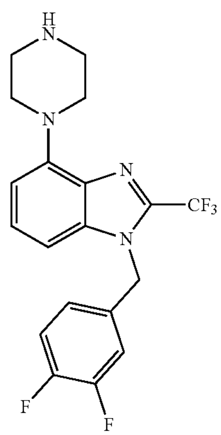 [SMILES: Fc1ccc(Cn2c(C(F)(F)F)nc3c(N4CCNCC4)cccc32)cc1F] | 1-(3,4-difluorobenzyl)-4-(piperazin-1-yl)-2-(trifluoromethyl)-1H-benzo[d]imidazole | Method B (UPLC-MS): 95.01%, 397.09 [M + H]$^+$, retention time: 5.01 min.; |
| 4206 | 11 | 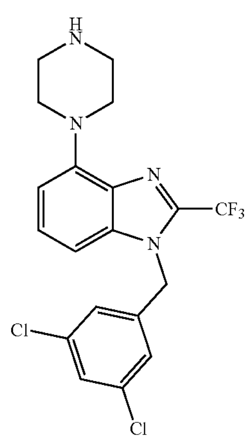 [SMILES: FC(F)(F)c1nc2c(N3CCNCC3)cccc2n1Cc1cc(Cl)cc(Cl)c1] | 1-(3,5-dichlorobenzyl)-4-(piperazin-1-yl)-2-(trifluoromethyl)-1H-benzo[d]imidazole | Method B (UPLC-MS): 95.00%, 428.99 [M + H]$^+$, retention time: 5.80 min.; |

| ADN | Cpd No | Structure | Name | Analytical Data |
|---|---|---|---|---|
| 4177 | 12 | 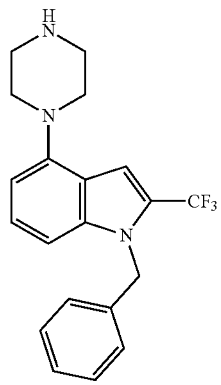 [SMILES: FC(F)(F)c1cc2c(N3CCNCC3)cccc2n1Cc1ccccc1] | 1-benzyl-4-(piperazin-1-yl)-2-(trifluoromethyl)-1H-indole* | Method A (analysis in basic gradient): 97%, 359.4 [M + H]⁺, retention time: 2.21 min.; |
| 4227 | 13 | 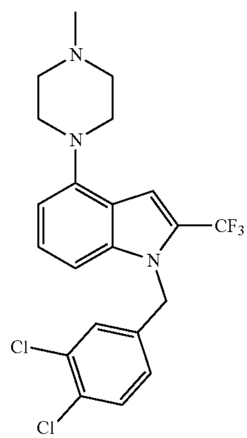 [SMILES: CN1CCN(c2cccc3c2cc(C(F)(F)F)n3Cc2ccc(Cl)c(Cl)c2)CC1] | 1-(3,4-dichlorobenzyl)-4-(4-methylpiperazin-1-yl)-2-(trifluoromethyl)-1H-indole | Method A (analysis in basic gradient): 97.72%, 443.6 [M + H]⁺, retention time: 4.249 min.; |
| 4228 | 14 | 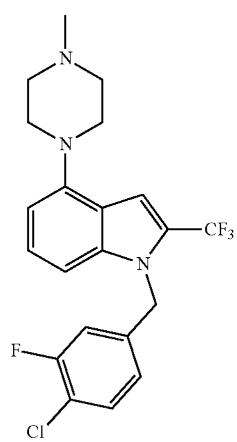 [SMILES: CN1CCN(c2cccc3c2cc(C(F)(F)F)n3Cc2ccc(Cl)c(F)c2)CC1] | 1-(4-chloro-3-fluorobenzyl)-4-(4-methylpiperazin-1-yl)-2-(trifluoromethyl)-1H-indole | Method A (analysis in basic gradient): 96.14%, 425.8 [M + H]⁺, retention time: 4.165 min.; |

-continued

| ADN | Cpd No | Structure | Name | Analytical Data |
|---|---|---|---|---|
| 4229 | 15 | 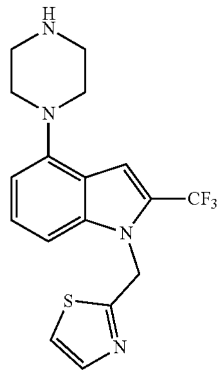 [SMILES: FC(F)(F)c1cc2c(N3CCNCC3)cccc2n1Cc1nccs1] | 4-(piperazin-1-yl)-1-(1,3-thiazol-2-ylmethyl)-2-(trifluoromethyl)-1H-indole* | Method A (analysis in basic gradient): 99.23%, 366.8 [M + H]+, retention time: 3.063 min.; |
| 4230 | 16 | 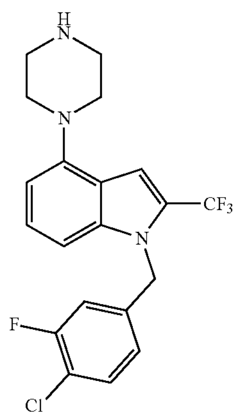 [SMILES: Fc1cc(Cn2c(C(F)(F)F)cc3c(N4CCNCC4)cccc32)ccc1Cl] | 1-(4-chloro-3-fluorobenzyl)-4-(piperazin-1-yl)-2-(trifluoromethyl)-1H-indole* | Method A (analysis in basic gradient): 99.57%, 411.8 [M + H]+, retention time: 3.954 min.; |
| 4231 | 17 | 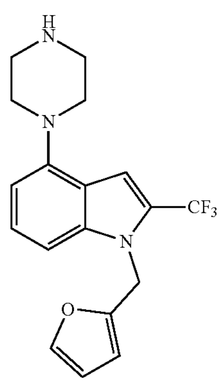 [SMILES: FC(F)(F)c1cc2c(N3CCNCC3)cccc2n1Cc1ccco1] | 1-(furan-2-ylmethyl)-4-(piperazin-1-yl)-2-(trifluoromethyl)-1H-indole | Method A (analysis in basic gradient): 98.90%, 349.8 [M + H]+, retention time: 3.54 min.; |
| 4232 | 18 | 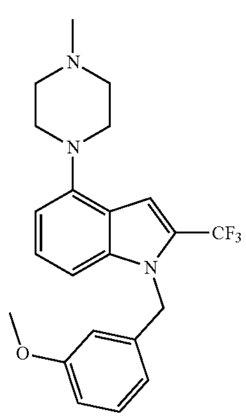 [SMILES: COc1cccc(Cn2c(C(F)(F)F)cc3c(N4CCN(C)CC4)cccc32)c1] | 1-(3-methoxybenzyl)-4-(4-methylpiperazin-1-yl)-2-(trifluoromethyl)-1H-indole* | Method A (analysis in basic gradient): 99.5%, 403.52 [M + H]+, retention time: 3.96 min.; |

| ADN | Cpd No | Structure | Name | Analytical Data |
|---|---|---|---|---|
| 4233 | 19 | 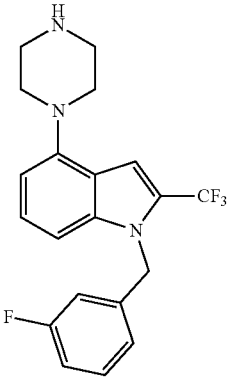 [SMILES: Fc1cccc(Cn2c(C(F)(F)F)cc3c(N4CCNCC4)cccc32)c1] | 1-(3-fluorobenzyl)-4-(piperazin-1-yl)-2-(trifluoromethyl)-1H-indole | Method A (analysis in basic gradient): 98.97%, 378.18 [M + H]⁺, retention time: 3.744 min.; |
| 4234 | 20 | 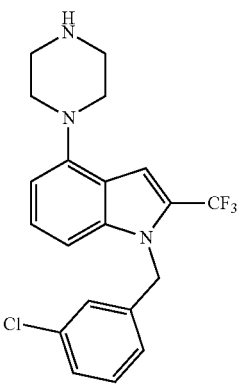 [SMILES: FC(F)(F)c1cc2c(N3CCNCC3)cccc2n1Cc1cccc(Cl)c1] | 1-(3-chlorobenzyl)-4-(piperazin-1-yl)-2-(trifluoromethyl)-1H-indole* | Method A (analysis in basic gradient): 97.8%, 393.83 [M + H]⁺, retention time: 3.91 min.; |
| 4235 | 21 | 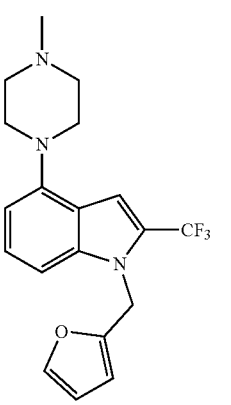 [SMILES: CN1CCN(c2cccc3c2cc(C(F)(F)F)n3Cc2ccco2)CC1] | 1-(furan-2-ylmethyl)-4-(4-methylpiperazin-1-yl)-2-(trifluoromethyl)-1H-indole | Method A (analysis in basic gradient): 99.70%, 364.3 [M + H]⁺, retention time: 3.79 min.; |

-continued

| ADN | Cpd No | Structure | Name | Analytical Data |
|---|---|---|---|---|
| 4240 | 22 | 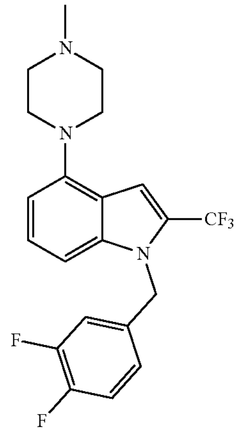 | 1-(3,4-difluorobenzyl)-4-(4-methylpiperazin-1-yl)-2-(trifluoromethyl)-1H-indole | Method A (analysis in basic gradient): 94.70%, 409.8 [M + H]+, retention time: 4.00 min.; |
| 4241 | 23 | 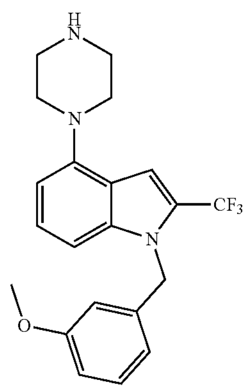 [SMILES: COc1cccc(Cn2c(C(F)(F)F)cc3c(N4CCNCC4)cccc32)c1] | 1-(3-methoxybenzyl)-4-(piperazin-1-yl)-2-(trifluoromethyl)-1H-indole* | Method A (analysis in basic gradient): 98.7%, 389.41 [M + H]+, retention time: 3.73 min.; |
| 4242 | 24 | 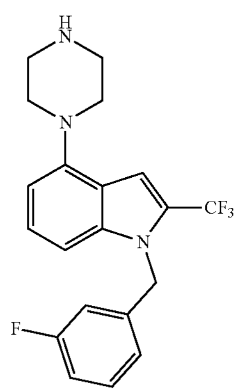 [SMILES: Fc1cccc(Cn2c(C(F)(F)F)cc3c(N4CCNCC4)cccc32)c1] | 1-(3-fluorobenzyl)-4-(4-methylpiperazin-1-yl)-2-(trifluoromethyl)-1H-indole* | Method A (analysis in basic gradient): 99.2%, 391.41 [M + H]+, retention time: 6.51 min.; |

-continued

| ADN | Cpd No | Structure | Name | Analytical Data |
|---|---|---|---|---|
| 4243 | 25 | 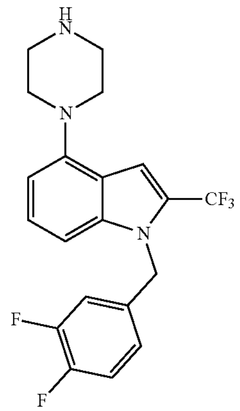 [SMILES: Fc1ccc(Cn2c(C(F)(F)F)cc3c(N4CCNCC4)cccc32)cc1F] | 1-(3,4-difluorobenzyl)-4-(piperazin-1-yl)-2-(trifluoromethyl)-1H-indole | Method A (analysis in basic gradient): 96.75%, 395.9 [M + H]$^+$, retention time: 3.75 min.; |
| 4244 | 26 | 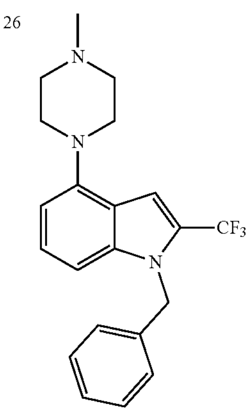 | 1-benzyl-4-(4-methylpiperazin-1-yl)-2-(trifluoromethyl)-1H-indole | Method A (analysis in basic gradient): 99.6%, 374.98 [M + H]$^+$, retention time: 4.011 min.; |
| 4245 | 27 | 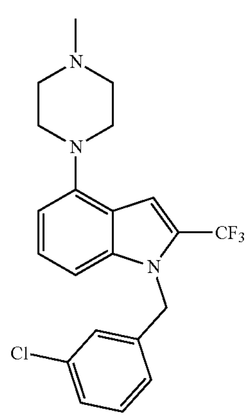 [SMILES: CN1CCN(c2cccc3c2cc(C(F)(F)F)n3Cc2cccc(Cl)c2)CC1] | 1-(3-chlorobenzyl)-4-(4-methylpiperazin-1-yl)-2-(trifluoromethyl)-1H-indole* | Method A (analysis in basic gradient): 97.95%, 407.86 [M + H]$^+$, retention time: 4.10 min.; |

-continued

| ADN | Cpd No | Structure | Name | Analytical Data |
|---|---|---|---|---|
| 4250 | 28 | 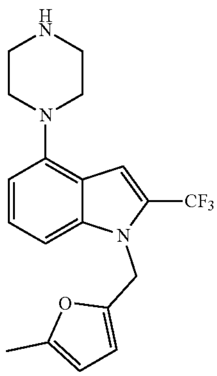 [SMILES: Cc1ccc(Cn2c(C(F)(F)F)cc3c(N4CCNCC4)cccc32)o1] | 1-[(5-methylfuran-2-yl)methyl]-4-(piperazin-1-yl)-2-(trifluoromethyl)-1H-indole | Method A (analysis in basic gradient): 99%, 363.91 [M + H]+, retention time: 3.849 min.; |
| 4251 | 29 | 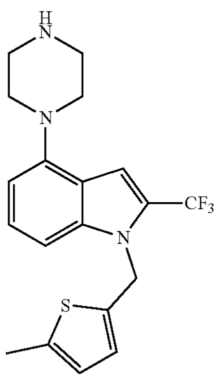 [SMILES: Cc1ccc(Cn2c(C(F)(F)F)cc3c(N4CCNCC4)cccc32)s1] | 1-[(5-methylthiophen-2-yl)methyl]-4-(piperazin-1-yl)-2-(trifluoromethyl)-1H-indole | Method A (analysis in basic gradient): 96.65%, 380.30 [M + H]+, retention time: 3.934 min.; |
| 4252 | 30 | 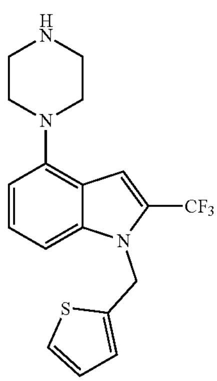 [SMILES: FC(F)(F)c1cc2c(N3CCNCC3)cccc2n1Cc1cccs1] | 4-(piperazin-1-yl)-1-(thiophen-2-ylmethyl)-2-(trifluoromethyl)-1H-indole* | Method A (analysis in basic gradient): 95%, 365.57 [M + H]+, retention time: 3.74 min.; |
| 4253 | 31 | 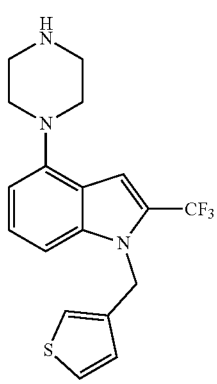 [SMILES: FC(F)(F)c1cc2c(N3CCNCC3)cccc2n1Cc1ccsc1] | 4-(piperazin-1-yl)-1-(thiophen-3-ylmethyl)-2-(trifluoromethyl)-1H-indole* | Method A (analysis in basic gradient): 96.5%, 365.82 [M + H]+, retention time: 3.75 min.; |

-continued

| ADN | Cpd No | Structure | Name | Analytical Data |
|---|---|---|---|---|
| 4254 | 32 | 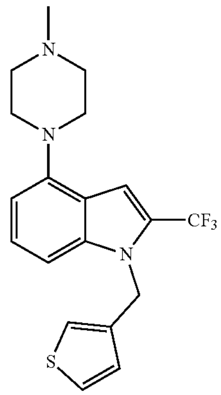 [SMILES: CN1CCN(c2cccc3c2cc(C(F)(F)F)n3Cc2ccsc2)CC1] | 4-(4-methylpiperazin-1-yl)-1-(thiophen-3-ylmethyl)-2-(trifluoromethyl)-1H-indole* | Method A (analysis in basic gradient): 95%, 379.86 [M + H]+, retention time: 3.99 min.; |
| 4255 | 33 | 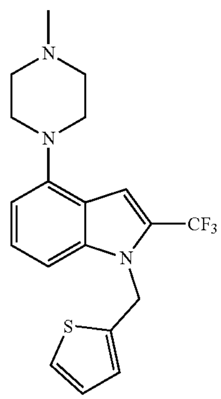 [SMILES: CN1CCN(c2cccc3c2cc(C(F)(F)F)n3Cc2cccs2)CC1] | 4-(4-methylpiperazin-1-yl)-1-(thiophen-2-ylmethyl)-2-(trifluoromethyl)-1H-indole* | Method A (analysis in basic gradient): 98.5%, 379.51 [M + H]+, retention time: 3.98 min.; |
| 4288 | 34 | 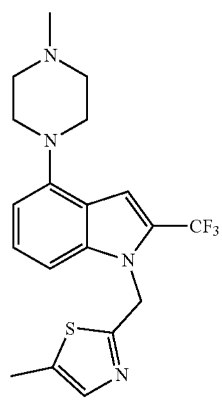 [SMILES: Cc1cnc(Cn2c(C(F)(F)F)cc3c(N4CCN(C)CC4)cccc32)s1] | 4-(4-methylpiperazin-1-yl)-1-[(5-methyl-1,3-thiazol-2-yl)methyl]-2-(trifluoromethyl)-1H-indole | Method A (analysis in basic gradient): 99.7%, 395.4 [M + H]+, retention time: 3.738 min.; |

*Compounds obtained in form of hydrochloride salt

Biological Examples

Biological Example 1. Receptor Binding Assays

Preparation of solutions of test and reference compounds. 1 mM stock solutions of tested compounds were prepared in DMSO. Serial dilutions of compounds were prepared in 96-well microplate in assay buffers using automated pipetting system epMotion 5070 (Eppendorf). Each compound was tested in 10 concentrations from 1.0E-6 to 1.0E-11M (final concentration).

5-HT$_{2A}$ Receptor Binding Assay. Radioligand binding was performed using membranes from CHO K$_1$ cells stably transfected with the human 5-HT$_{2A}$ receptor (PerkinElmer). All assays were carried out in duplicates. 50 μl working solution of the tested compounds, 50 μl [3H]-ketanserin (final concentration 1 nM) and 150 μl diluted membranes (7 μg protein per well) prepared in assay buffer (50 mM Tris, pH 7.4, 4 mM CaCl2, 0.1% ascorbic acid) were transferred to polypropylene 96-well microplate using 96-wells pipetting station Rainin Liquidator (MettlerToledo). Mianserin (10 μM) was used to define nonspecific binding. Microplate was covered with a sealing tape, mixed and incubated for 60 minutes at 27° C. The reaction was terminated by rapid filtration through GF/B filter mate presoaked with 0.5% polyethyleneimine for 30 minutes. Ten rapid washes with 200 μl 50 mM Tris buffer (4° C., pH 7.4) were performed using automated harvester system Harvester-96

MACH III FM (Tomtec). The filter mates were dried at 37° C. in forced air fan incubator and then solid scintillator MeltiLex was melted on filter mates at 90° C. for 5 minutes. Radioactivity was counted in MicroBeta2 scintillation counter (PerkinElmer). Data were fitted to a one-site curve-fitting equation with Prism 6 (GraphPad Software) and Ki values were estimated from the Cheng-Prusoff equation.

5-HT6 Receptor Binding Assay. Radioligand binding was performed using membranes from CHO-$K_1$ cells stably transfected with the human 5-$HT_6$ receptor (PerkinElmer). All assays were carried out in duplicates. 50 µl working solution of the tested compounds, 50 µl [3H]-LSD (final concentration 1 nM) and 150 µl diluted membranes (8 µg protein per well) prepared in assay buffer (50 mM Tris, pH 7.4, 10 mM MgCl2, 0.1 mM EDTA) were transferred to polypropylene 96 well microplate using 96-wells pipetting station Rainin Liquidator (MettlerToledo). Methiothepin (10 µM) was used to define nonspecific binding. Microplate was covered with a sealing tape, mixed and incubated for 60 minutes at 37° C. The reaction was terminated by rapid filtration through GF/A filter mate presoaked with 0.5% polyethyleneimine for 30 minutes. Ten rapid washes with 200 µl 50 mM Tris buffer (4° C., pH 7.4) were performed using automated harvester system Harvester-96 MACH III FM (Tomtec). The filter mates were dried at 37° C. in forced air fan incubator and then solid scintillator MeltiLex was melted on filter mates at 90° C. for 5 minutes. Radioactivity was counted in MicroBeta2 scintillation counter (PerkinElmer). Data were fitted to a one-site curve-fitting equation with Prism 6 (GraphPad Software) and Ki values were estimated from the Cheng-Prusoff equation.

| | in vitro binding affinity | |
|---|---|---|
| | 5-HT6 Ki [nM] | 5-HT2A Ki [nM] |
| 1 | 1.3 | 4.2 |
| 2 | 2.2 | 3.1 |
| 6 | 1.7 | 3.8 |
| 7 | 1.6 | 2.9 |
| 8 | 2 | 2.9 |
| 12 | 0.29 | 2.1 |
| 13 | 0.98 | 2.6 |
| 14 | 0.65 | 0.39 |
| 16 | 0.62 | 0.82 |
| 17 | 0.62 | 1.6 |
| 18 | 0.27 | 4.2 |
| 19 | 0.35 | 1.3 |
| 20 | 0.53 | 2.2 |
| 21 | 0.18 | 0.54 |
| 22 | 0.5 | 0.45 |
| 24 | 0.092 | 0.73 |
| 25 | 0.37 | 0.71 |
| 26 | 0.087 | 0.91 |
| 28 | 4 | 0.48 |
| 29 | 0.11 | 0.37 |
| 30 | 0.071 | 0.33 |
| 31 | 0.11 | 1.5 |
| 32 | 0.061 | 2.3 |
| 33 | 0.069 | 0.17 |

The results presented above confirm that all the tested compounds possess high affinity for both the 5-$HT_{2A}$ and 5-$HT_6$ receptors, confirming their dual receptor ligand properties.

Biological Example 2. Functional Activity Assays

Preparation of solutions of test and reference compounds. 1 mM stock solutions of the tested compounds were prepared in DMSO. Serial dilutions were prepared in 96-well microplate in assay buffers using automated pipetting system epMotion 5070 (Eppendorf). Two independent experiments in duplicates were performed and 6 to 10 concentrations were tested.

5-$HT_{2A}$ and 5-$HT_6$ Functional Activity Assays. Cellular aequorin-based functional assays were performed with γ-irradiated recombinant CHO-$K_1$ cells expressing mitochondrially-targeted Aequorin, human GPCR (5-HT2A or 5-HT6) and the promiscuous G protein α16 (PerkinElmer). Assays were performed according to the standard protocol provided by the manufacturer. After thawing, cells were transferred to assay buffer (DMEM/HAM's F12 with 0.1% protease-free BSA) and centrifuged. Cell pellet was resuspended in assay buffer and coelenterazine h was added at final concentrations of 5 µM. Cell suspension was incubated at 21° C., protected from light with constant agitation, for 4 hours and then diluted with assay buffer to a concentration of 250,000 cells/ml. After 1 hour incubation 50 µl cell suspension was dispensed using automatic injectors built in radiometric and luminescence plate counter MicroBeta2 LumiJET (PerkinElmer, USA) into white opaque 96-well microplate preloaded with tested compounds. Immediate light emission generated following calcium mobilization was recorded for 30-60 seconds. In antagonist mode, after 15-30 minutes incubation reference agonist was added to the above assay mix and light emission was recorded again. Final concentration of reference agonist was equal EC80: serotonin 40 nM for 5-$HT_6$ receptor and α-methylserotonin 30 nM for 5-$HT_{2A}$ receptor. The assays were performed in the agonist mode (5-HT6 AGO and 5-HT2A AGO) as well as antagonist mode (5-HT6 ANT and 5-HT2A ANT).

IC50 and EC50 were determined by non-linear regression analysis using GraphPad Prism 6.0 software. The logIC50 was used to obtain the Kb by applying the Cheng-Prusoff approximation.

| | In vitro functional activity | | | |
|---|---|---|---|---|
| | 5-HT6 AGO EC50 [nM] | 5-HT6 ANT Kb [nM] | 5-HT2A AGO EC50 [nM] | 5-HT2A ANT Kb [nM] |
| 1 | N.C. | 2.5 | N,C. | 18 |
| 7 | N.C. | 1.9 | N.C. | 22 |
| 12 | N.C. | 0.49 | N.C. | 31 |
| 13 | N.C | 9.1 | N.C. | N.T. |
| 14 | N.C. | 5.5 | N.C. | 59 |
| 16 | N.C. | 4.4 | N.C. | 55 |
| 17 | N.C. | 0.47 | N.C. | 10 |
| 19 | N.C. | 0.14 | N.C. | 21 |
| 20 | N.C. | 1.2 | N.C. | 53 |
| 21 | N.C. | 0.27 | N.C. | 4.3 |
| 22 | N.C. | 4.8 | N.C. | 26 |
| 23 | N.C. | 0.26 | N.C. | 28 |
| 24 | N.C. | 1.1 | N.C. | 28 |
| 25 | N.C. | 0.65 | N.C. | 20 |
| 27 | N.C. | 0.31 | N.C. | 56 |
| 28 | N.C. | 0.25 | N.C. | 16 |
| 29 | N.C. | 0.051 | N.C. | 9.8 |
| 30 | N.C. | 0.65 | N.C. | 5.5 |
| 31 | N.C. | 0.2 | N.C. | 16 |
| 32 | N.C. | 0.37 | N.C. | 11 |
| 33 | N.C. | 0.28 | N.C. | 9.7 |

N.T. - not tested,
N.C. - non calculable (calculation of EC50 values was impossible because the compounds did not exert any agonist effect)

The results presented above confirm that all the tested compounds possess high antagonistic properties at both the 5-HT2A and 5-HT6 receptors, confirming their dual receptor antagonist properties.

Biological Example 3. Effects of Compounds 1 and 17, On Head Twitches Induced by a 5-HT$_{2A/C}$ Receptor Agonist, 1-(2,5-Dimethoxy-4-Iodophenyl)-2-Aminopropane Hydrochloride (DOI) in Wistar Rats A. Subjects Drug-naive male Wistar rats (Charles River, Sulzfeld, Germany) were used. Rats were housed four per standard plastic cage and kept in a room with constant environmental conditions (22±1° C., relative humidity 60%, a 12:12 light-dark cycle with lights on at 07:00 a.m.). Animals were supplied by the breeder 2 weeks before the onset of behavioral procedures. During this time, the subjects were weighted and handled several times. The rats were also habituated to p.o. administration of tested compounds in form of hydrochloride salt by gavage dosing of distilled water (1-2 mL). Tap water and standard lab chow (Labofeed H, WPIK, Kcynia, Poland) was available ad libitum.

Treatment of rats in the present study was in full accordance with the ethical standards laid down in respective Polish and European (Directive no. 2010/63/EU) regulations. All procedures were reviewed and approved by an ethics committee.

B. DOI-Induced Head Twitches

All tests were carried out in a sound-attenuated experimental room between 10:00 a.m. and 04:00 p.m. DOI-induced head twitches were scored as described by Millan et al. (2000). Rats were injected with DOI (2.5 mg/kg, i.p.) and placed in glass observation cages (25×25×40 cm, W×H×L) with wood chip bedding on the floor. Five minutes later, head twitches were counted for 5 min. (300 s) by a trained observer. Tested compounds in form of hydrochloride salt were administered p.o. 180 min. before the start of the observation period to different groups of drug naive subjects.

C. Drugs

DOI was dissolved in sterile physiological saline (Baxter, Warsaw, Poland) and administered i.p. in a volume of 1.0 ml/kg. Tested compounds in form of hydrochloride salt were dissolved in 0.5% tween and administered p.o. in a volume of 2.0 ml/kg. All solutions were prepared immediately prior to use and protected from the light.

D. Data Analysis:

Total numbers of head twitches (n/5 min.) were analyzed with the aid of the Kruskal-Wallis analysis of variance (ANOVA). The Mann-Whitney U test was used for individual post hoc comparisons (Table 1). P values lower than 0.05 were considered significant. The Statistica 12.0 software package for Windows (StatSoft, Tulsa, OK, USA) was used to analyze all data.

Results

Both tested compounds, dose-dependently attenuated DOI (2.5 mg/kg)-induced head twitches with a minimum effective dose (MED) of 3.0 mg/kg for Compound 1 and 1.0 mg/kg for Compound 17.

Biological Example 4. Effects of Compounds 1 and 17, On Scopolamine-Induced Deficits in Learning and Memory in the Passive Avoidance Test in Wistar Rats A. Subjects Drug-naive male Wistar rats (Charles River, Sulzfeld, Germany) were used. Rats were housed four per standard plastic cage and kept in a room with constant environmental conditions (22±1° C., relative humidity 60%, a 12:12 light-dark cycle with lights on at 7:00 a.m.). Animals were supplied by the breeder 2-3 weeks before the onset of behavioral procedures. During this time, the subjects were weighted and handled several times. The rats were also habituated to p.o. administration of tested compounds in form of hydrochloride salt by gavage dosing of distilled water (1-2 mL). Tap water and standard lab chow (Labofeed H, WPIK, Kcynia, Poland) was available ad libitum.

Treatment of rats in the present study was in full accordance with the ethical standards laid down in respective Polish and European (Directive no. 2010/63/EU) regulations. All procedures were reviewed and approved by a local ethics committee.

B. Step-Through Passive Avoidance Test

Effects of tested compounds on learning and memory function were evaluated using a step-through passive avoidance test (Ishiyama et al., 2007). The passive avoidance apparatus (PACS-30, Columbus Instruments, Columbus, OH, USA) comprised four identical stainless-steel cages with black Plexiglas covers. Each cage consisted of a lighted and dark compartment (23×23×23 cm) and a stainless-steel grid floor. The two compartments were separated by the automated sliding door (PACS-30, Columbus).

In the training (acquisition) session, the animals were individually placed in the lighted compartment and allowed to explore it freely for 10 s. The sliding door was then opened, and the step-through latency for animals to enter the dark compartment was measured with a 300-s cut-off time. As soon as the animals entered the dark compartment, the door was closed. An inescapable foot-shock (0.5 mA for 3 s) was delivered 3 s later through the grid floor with a constant current shock generator (Columbus). Scopolamine (0.3 mg/kg) was administered i.p. 30 min. before the training session. Tested compounds in form of hydrochloride salt, or their vehicle, were administered p.o. 180 min. before the start of the training session.

The test (expression) session was performed 24 h after the training session using the same paradigm but without any foot-shock or drug injections. Step-through latencies for animals to enter the dark compartment were measured with a 300-s cut-off time. Tested compounds-induced changes in step-through latencies to enter the dark compartment in the test session were treated as a measure of its promnesic or amnestic effects (Ishiyama et al., 2007).

C. Drugs

Scopolamine (provided by Adamed) was dissolved in sterile physiological saline (0.9% NaCl; Baxter, Warsaw, Poland) and administered i.p. in a volume of 2.0 ml/kg. Tested compounds in form of hydrochloride salt were dissolved in 0.5% Tween and administered p.o. in a volume of 2.0 ml/kg. All solutions were prepared immediately prior to use and protected from the light.

D. Data Presentation and Analysis

Body weights (g) and training/test latencies (s) were analyzed with the aid of a one-way analysis of variance (ANOVA). As passive avoidance data were not normally distributed, step-through latencies were also analyzed with the aid of the Kruskal-Wallis ANOVA and Mann-Whitney U test. P values less than 0.05 were considered significant. The Statistica 12.0 software package for Windows (StatSoft, Tulsa, OK, USA) was used to analyze all data.

Results

Both tested compounds, administered in combination with scopolamine (0.3 mg/kg), significantly elongated step-through latencies to enter the dark compartment in the test session. The minimal effective dose (MED) was 3.0 mg/kg for Compound 1 and 1.0 mg/kg for Compound 17.

REFERENCES

Amano, N., Inuzuka, S., Ogihara, T., 2009. Behavioral and psychological symptoms of dementia and medical treatment. Psychogeriatr. Off. J. Jpn. Psychogeriatr. Soc. 9, 45-49. https://doi.org/10.1111/j.1479-8301.2009.00284.x Ballard, C., Waite, J., 2006. The effectiveness of atypical antipsychotics for the treatment of aggression and psychosis in Alzheimer's disease. Cochrane Database Syst. Rev. CD003476. https://doi.org/10.1002/14651858.CD003476.pub2

Carson, S., McDonagh, M. S., Peterson, K., 2006. A systematic review of the efficacy and safety of atypical antipsychotics in patients with psychological and behavioral symptoms of dementia. J. Am. Geriatr. Soc. 54, 354-361. https://doi.org/10.1111/j.1532-5415.2005.00566.x De Deyn, P., Jeste, D. V., Swanink, R., Kostic, D., Breder, C., Carson, W. H., Iwamoto, T., 2005. Aripiprazole for the treatment of psychosis in patients with Alzheimer's disease: a randomized, placebo-controlled study. J. Clin. Psychopharmacol. 25, 463-467.

Fasano, A., Plotnik, M., Bove, F., Berardelli, A., 2012. The neurobiology of falls. Neurol. Sci. Off. J. Ital. Neurol. Soc. Ital. Soc. Clin. Neurophysiol. 33, 1215-1223. https://doi.org/10.1007/s10072-012-1126-6

Ferri, C. P., Prince, M., Brayne, C., Brodaty, H., Fratiglioni, L., Ganguli, M., Hall, K., Hasegawa, K., Hendrie, H., Huang, Y., Jorm, A., Mathers, C., Menezes, P. R., Rimmer, E., Scazufca, M., Alzheimer's Disease International, 2005. Global prevalence of dementia: a Delphi consensus study. Lancet Lond. Engl. 366, 2112-2117. https://doi.org/10.1016/S0140-6736(05)67889-0

Fijal, K., Popik, P., Nikiforuk, A., 2014. Co-administration of 5-$HT_6$ receptor antagonists with clozapine, risperidone, and a 5-$HT_{2A}$ receptor antagonist: effects on prepulse inhibition in rats. Psychopharmacology (Berl.) 231, 269-281. https://doi.org/10.1007/s00213-013-3234-2

Gauthier, S., Cummings, J., Ballard, C., Brodaty, H., Grossberg, G., Robert, P., Lyketsos, C., 2010. Management of behavioral problems in Alzheimer's disease. Int. Psychogeriatr. 22, 346-372. https://doi.org/10.1017/S1041610209991505

Hersch, E. C., Falzgraf, S., 2007. Management of the behavioral and psychological symptoms of dementia. Clin. Interv. Aging 2, 611-621.

Holmes, C., Arranz, M. J., Powell, J. F., Collier, D. A., Lovestone, S., 1998. 5-HT2A and 5-HT2C receptor polymorphisms and psychopathology in late onset Alzheimer's disease. Hum. Mol. Genet. 7, 1507-1509.

Home|Cochrane Library [WWW Document], n.d. URL http://www.cochranelibrary.com/(accessed 2.7.18).

Jeste, D. V., Blazer, D., Casey, D., Meeks, T., Salzman, C., Schneider, L., Tariot, P., Yaffe, K., 2008. ACNP White Paper: update on use of antipsychotic drugs in elderly persons with dementia. Neuropsychopharmacol. Off. Publ. Am. Coll. Neuropsychopharmacol. 33, 957-970. https://doi.org/10.1038/sj.npp.1301492

Jeste, D. V., Finkel, S. I., 2000. Psychosis of Alzheimer's disease and related dementias. Diagnostic criteria for a distinct syndrome. Am. J. Geriatr. Psychiatry Off. J. Am. Assoc. Geriatr. Psychiatry 8, 29-34.

Jones, C. A., Watson, D. J. G., Fone, K. C. F., 2011. Animal models of schizophrenia. Br. J. Pharmacol. 164, 1162-1194. https://doi.org/10.1111/j.1476-5381.2011.01386.x Liperoti, R., Pedone, C., Corsonello, A., 2008. Antipsychotics for the treatment of behavioral and psychological symptoms of dementia (BPSD). Curr. Neuropharmacol. 6, 117-124. https://doi.org/10.2174/157015908784533860

Liu, K. G., Robichaud, A. J., 2009. 5-$HT_6$ antagonists as potential treatment for cognitive dysfunction. Drug Dev. Res. 70, 145-168. https://doi.org/10.1002/ddr.20293

Lorke, D. E., Lu, G., Cho, E., Yew, D. T., 2006. Serotonin 5-$HT_{2A}$ and 5-$HT_6$ receptors in the prefrontal cortex of Alzheimer and normal aging patients. BMC Neurosci. 7, 36. https://doi.org/10.1186/1471-2202-7-36

Maehara, S., Hikichi, H., Satow, A., Okuda, S., Ohta, H., 2008. Antipsychotic property of a muscarinic receptor agonist in animal models for schizophrenia. Pharmacol. Biochem. Behav. 91, 140-149. https://doi.org/10.1016/j.pbb.2008.06.023

Marcos, B., Garcia-Alloza, M., Gil-Bea, F. J., Chuang, T. T., Francis, P. T., Chen, C. P., Tsang, S. W. T. Y., Lai, M. K. P., Ramirez, M. J., 2008. Involvement of an altered 5-HT -{6} receptor function in behavioral symptoms of Alzheimer's disease. J. Alzheimers Dis. JAD 14, 43-50.

Marsh, A., 1979. Visual hallucinations during hallucinogenic experience and schizophrenia. Schizophr. Bull. 5, 627-630.

Murray, P. S., Kirkwood, C. M., Gray, M. C., Fish, K. N., Ikonomovic, M. D., Hamilton, R. L., Kofler, J. K., Klunk, W. E., Lopez, O. L., Sweet, R. A., 2014. Hyperphosphorylated tau is elevated in Alzheimer's disease with psychosis. J. Alzheimers Dis. JAD 39, 759-773. https://doi.org/10.3233/JAD-131166

Nichols, D. E., 2004. Hallucinogens. Pharmacol. Ther. 101, 131-181. https://doi.org/10.1016/j.pharmthera.2003.11.002

Nobili, A., Pasina, L., Trevisan, S., Riva, E., Lucca, U., Tettamanti, M., Matucci, M., Tarantola, M., 2009. Use and misuse of antipsychotic drugs in patients with dementia in Alzheimer special care units. Int. Clin. Psychopharmacol. 24, 97-104.

Riemer, C., Borroni, E., Levet-Trafit, B., Martin, J. R., Poli, S., Porter, R. H. P., Bös, M., 2003. Influence of the 5-$HT_6$ receptor on acetylcholine release in the cortex: pharmacological characterization of 4-(2-bromo-6-pyrrolidin-1-ylpyridine-4-sulfonyl)phenylamine, a potent and selective 5-$HT_6$ receptor antagonist. J. Med. Chem. 46, 1273-1276. https://doi.org/10.1021/jm021085c Schneider, L. S., Tariot, P. N., Dagerman, K. S., Davis, S. M., Hsiao, J. K., Ismail, M. S., Lebowitz, B. D., Lyketsos, C. G., Ryan, J. M., Stroup, T. S., Sultzer, D. L., Weintraub, D., Lieberman, J. A., CATIE-AD Study Group, 2006. Effectiveness of atypical antipsychotic drugs in patients with Alzheimer's disease. N. Engl. J. Med. 355, 1525-1538. https://doi.org/10.1056/NEJMoa061240

Schulze, J., Glaeske, G., van den Bussche, H., Kaduszkiewicz, H., Koller, D., Wiese, B., Hoffmann, F., 2013a. Prescribing of antipsychotic drugs in patients with dementia: a comparison with age-matched and sex-

The invention claimed is:

1. A pharmaceutical composition comprising a compound having the structure:

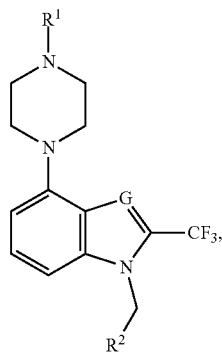

wherein:
G is CH or N;
R1 is H, C1-C4-alkyl, HO-$C_1$-$C_4$-alkyl or $C_1$-$C_4$-alkyl-O—$C_1$-$C_4$-alkyl; and
$R^2$ is selected from group consisting of:
(a) phenyl group unsubstituted or substituted with at least one substituent, or
(b) 5-or 6-membered heteroaryl group unsubstituted or substituted with at least one substituent,
wherein the substituent is selected from a group consisting of F, Cl, Br, $C_1$-$C_4$-alkyl-, and $C_1$-$C_4$-alkyl -O—;
or a pharmaceutically acceptable salt thereof, and scopolamine.

2. The pharmaceutical composition of claim 1, wherein $R^1$ is H, methyl, or 2-hydroxyethyl.

3. The pharmaceutical composition of claim 1, wherein the 5-or 6-membered heteroaryl is furyl, thienyl, thiazolyl, or pyridyl.

4. The pharmaceutical composition of claim 1, wherein the substituent is selected from a group consisting of F, Cl, methyl and methoxy.

5. The pharmaceutical composition of claim 1, wherein the compound is selected from a group consisting of the following:
1-benzyl-4-(piperazin-1-yl)-2-(trifluoromethyl)-1H -benzimidazole;
1-benzyl-4-(4-methylpiperazin-1-yl)-2-(trifluoromethyl)-1H -benzimidazole;
2-{4-[1-benzyl-2-(trifluoromethyl)-1H-benzimidazol-4-yl]piperazin-1-yl}ethanol;
1-(furan-2-ylmethyl)-4-(piperazin-1-yl)-2-(trifluoromethyl)-1H -benzimidazole;
1-[(5-methylfuran-2-yl) methyl]-4-(piperazin-1-yl)-2-(trifluoromethyl)-1H-benzimidazole;
1-(3-chlorobenzyl)-4-(piperazin-1-yl)-2-(trifluoromethyl)-1H -benzimidazole;
1-(3-fluorobenzyl)-4-(piperazin-1-yl)-2-(trifluoromethyl)-1H -benzimidazole;
1-(3, 4-dichlorobenzyl)-4-(piperazin-1-yl)-2-(trifluoromethyl) -1H-benzo [d]imidazole;
1-(3-chloro-4-fluorobenzyl)-4-(piperazin-1-yl)-2-(trifluoromethyl)-1H-benzo [d]imidazole;
1-(3, 4-difluorobenzyl)-4-(piperazin-1-yl)-2-(trifluoromethyl) -1H-benzo [d]imidazole;
1-(3, 5-dichlorobenzyl)-4-(piperazin-1-yl)-2-(trifluoromethyl) -1H-benzo [d]imidazole;
1-benzyl-4-(piperazin-1-yl)-2-(trifluoromethyl)-1H-indole;
1-(3, 4-dichlorobenzyl)-4-(4-methylpiperazin-1-yl)-2-(trifluoromethyl)-1H-indole;
1-(4-chloro-3-fluorobenzyl)-4-(4-methylpiperazin-1-yl)-2-(trifluoromethyl)-1H-indole;
4-(piperazin-1-yl)-1-(1,3-thiazol-2-ylmethyl)-2-(trifluoromethyl)-1H-indole;
1-(4-chloro-3-fluorobenzyl)-4-(piperazin-1-yl)-2-(trifluoromethyl)-1H-indole;
1-(furan-2-ylmethyl)-4-(piperazin-1-yl)-2-(trifluoromethyl)-1H -indole;
1-(3-methoxybenzyl)-4-(4-methylpiperazin-1-yl)-2-(trifluoromethyl)-1H-indole;
1-(3-fluorobenzyl)-4-(piperazin-1-yl)-2-(trifluoromethyl)-1H -indole;
1-(3-chloobenzyl)-4-(piperazin-1-yl)-2-(trifluoromethyl)-1H -indole;
1-(furan-2-ylmethyl)-4-(4-methylpiperazin-1-yl)-2-(trifluoromethyl)-1H-indole;

1-(3, 4-difluorobenzyl)-4-(4-methylpiperazin-1-yl)-2-(trifluoromethyl)-1H-indole;
1-(3-methoxybenzyl)-4-(piperazin-1-yl)-2-(trifluoromethyl)-1H-indole;
1-(3-fluorobenzyl)-4-(4-methylpiperazin-1-yl)-2-(trifluoromethyl)-1H-indole;
1-(3, 4-difluorobenzyl)-4-(piperazin-1-yl)-2-(trifluoromethyl)-1H-indole;
1-benzyl-4-(4-methylpiperazin-1-yl)-2-(trifluoromethyl)-1H-indole;
1-(3-chlorobenzyl)-4-(4-methylpiperazin-1-yl)-2-(trifluoromethyl)-1H-indole;
1-[(5-methylfuran-2-yl) methyl]-4-(piperazin-1-yl)-2-(trifluoromethyl)-1H-indole;
1-[(5-methylthiophen-2-yl) methyl]-4-(piperazin-1-yl)-2-(trifluoromethyl)-1H-indole; 4-(piperazin-1-yl)-1-(thiophen-2-ylmethyl)-2-(trifluoromethyl)-1H-indole;
4-(piperazin-1-yl)-1-(thiophen-3-ylmethyl)-2-(trifluoromethyl)-1H-indole;
4-(4-methylpiperazin-1-yl)-1-(thiophen-3-ylmethyl)-2-(trifluoromethyl)-1H-indole;
4-(4-methylpiperazin-1-yl)-1-(thiophen-2-ylmethyl)-2-(trifluoromethyl)-1H-indole; and
4-(4-methylpiperazin-1-yl)-1-[(5-methyl-1, 3-thiazol-2-yl) methyl]-2-(trifluoromethyl)-1H-indole, or pharmaceutically acceptable salt thereof.

6. The pharmaceutical composition of claim 1, wherein the pharmaceutical composition comprises

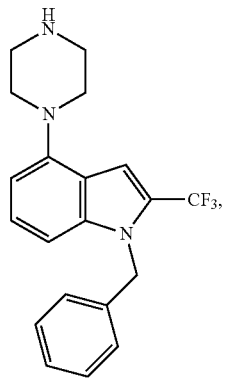 [SMILES: FC(F)(F)c1cc2c(N3CCNCC3)cccc2n1Cc1ccccc1]

or pharmaceutically acceptable salt thereof; and scopolamine.

7. The pharmaceutical composition of claim 1, wherein the pharmaceutical composition comprises the hydrochloride salt of

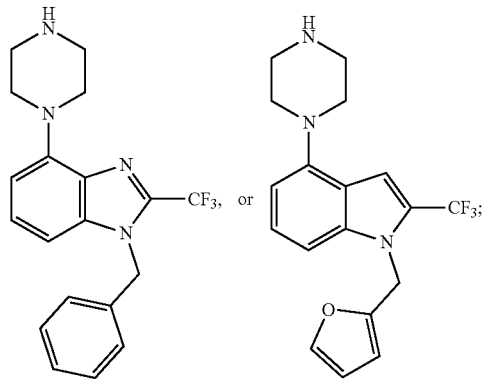 [SMILES: FC(F)(F)c1nc2c(N3CCNCC3)cccc2n1Cc1ccccc1 ; FC(F)(F)c1cc2c(N3CCNCC3)cccc2n1Cc1ccco1]

and scopolamine.

8. The pharmaceutical composition of claim 1, wherein the pharmaceutical composition comprises the hydrochloride salt of

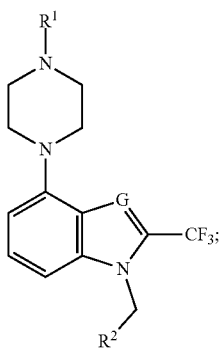

and scopolamine.

9. The pharmaceutical composition of claim 6, wherein the pharmaceutical composition comprises 0.1-1000 mg of

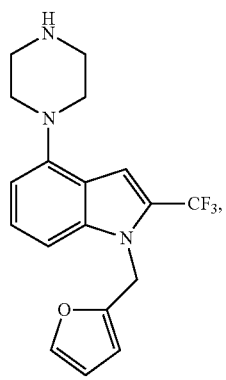

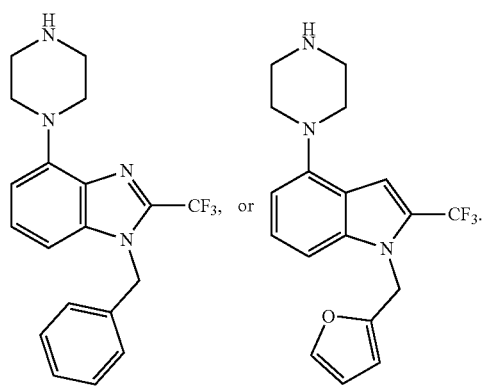 [SMILES: FC(F)(F)c1nc2c(N3CCNCC3)cccc2n1Cc1ccccc1 ; FC(F)(F)c1cc2c(N3CCNCC3)cccc2n1Cc1ccco1]

10. The pharmaceutical composition of claim 9, wherein the pharmaceutical composition comprises 0.1-10 mg of

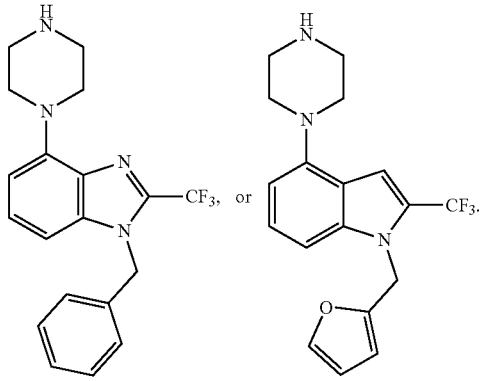 [SMILES: FC(F)(F)c1nc2c(N3CCNCC3)cccc2n1Cc1ccccc1 ; FC(F)(F)c1cc2c(N3CCNCC3)cccc2n1Cc1ccco1]

11. The pharmaceutical composition of claim 9, wherein the pharmaceutical composition comprises 10-100 mg of

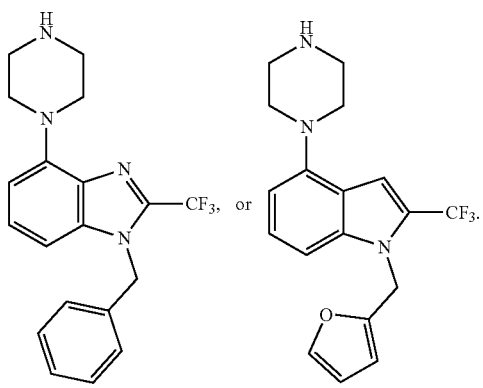 [SMILES: FC(F)(F)c1nc2c(N3CCNCC3)cccc2n1Cc1ccccc1 ; FC(F)(F)c1cc2c(N3CCNCC3)cccc2n1Cc1ccco1]

12. The pharmaceutical composition of claim 7, wherein the pharmaceutical composition comprises 0.1-1000 mg of the hydrochloride salt of

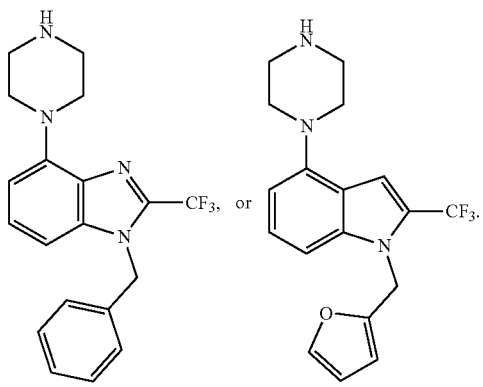 [SMILES: FC(F)(F)c1nc2c(N3CCNCC3)cccc2n1Cc1ccccc1 ; FC(F)(F)c1cc2c(N3CCNCC3)cccc2n1Cc1ccco1]

13. The pharmaceutical composition of claim 12, wherein the pharmaceutical composition comprises 0.1-10 mg of the hydrochloride salt of

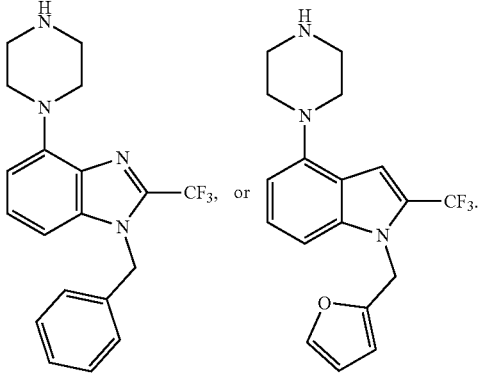 [SMILES: FC(F)(F)c1nc2c(N3CCNCC3)cccc2n1Cc1ccccc1 ; FC(F)(F)c1cc2c(N3CCNCC3)cccc2n1Cc1ccco1]

14. The pharmaceutical composition of claim 12, wherein the pharmaceutical composition comprises 10-100 mg of the hydrochloride salt of

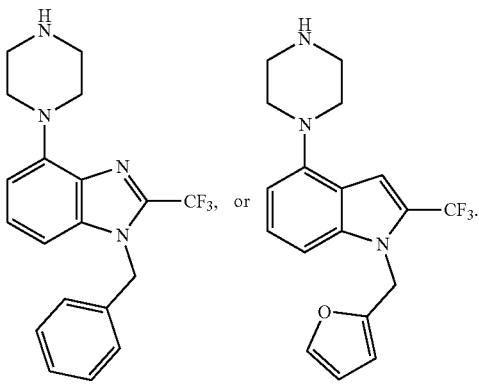 [SMILES: FC(F)(F)c1nc2c(N3CCNCC3)cccc2n1Cc1ccccc1 ; FC(F)(F)c1cc2c(N3CCNCC3)cccc2n1Cc1ccco1]

15. The pharmaceutical composition of claim 1, wherein the pharmaceutical composition comprises

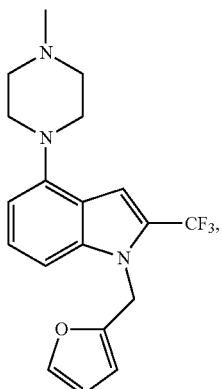

or

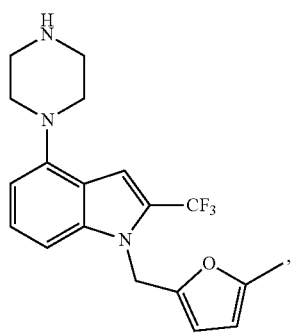 [SMILES: Cc1ccc(Cn2c(C(F)(F)F)cc3c(N4CCNCC4)cccc32)o1]

or pharmaceutically acceptable salt thereof; and scopolamine.

16. The pharmaceutical composition of claim 15, wherein the pharmaceutical composition comprises 0.1-1000 mg of

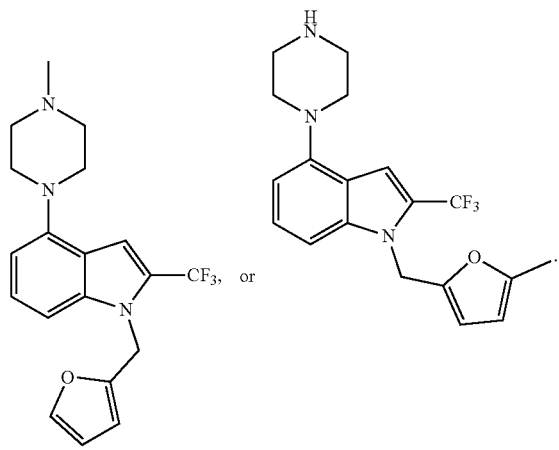 [SMILES: CN1CCN(c2cccc3c2cc(C(F)(F)F)n3Cc2ccco2)CC1 ; Cc1ccc(Cn2c(C(F)(F)F)cc3c(N4CCNCC4)cccc32)o1]

17. The pharmaceutical composition of claim 16, wherein the pharmaceutical composition comprises 0.1-10 mg of

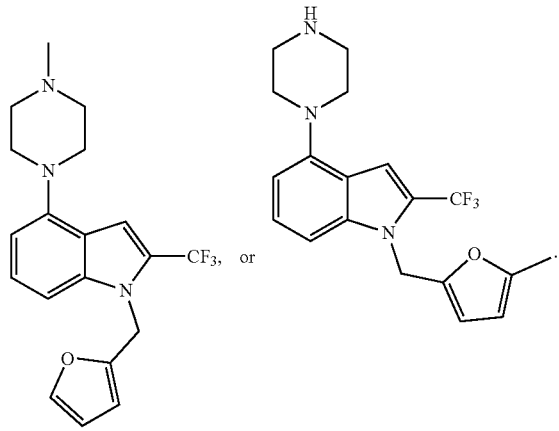 [SMILES: CN1CCN(c2cccc3c2cc(C(F)(F)F)n3Cc2ccco2)CC1 ; Cc1ccc(Cn2c(C(F)(F)F)cc3c(N4CCNCC4)cccc32)o1]

18. The pharmaceutical composition of claim 16, wherein the pharmaceutical composition comprises 10-100 mg of

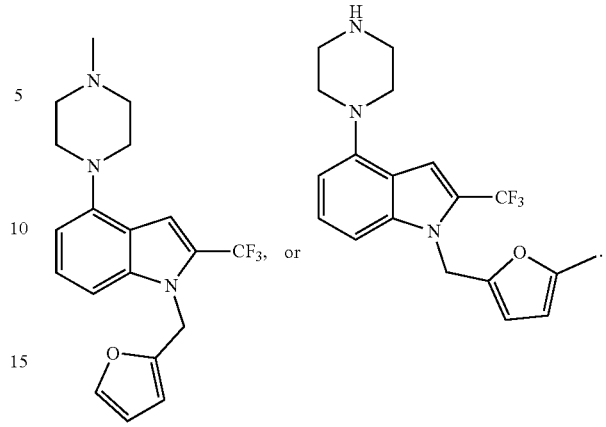

19. The pharmaceutical composition of claim 15, wherein the pharmaceutical composition comprises the hydrochloride salt of

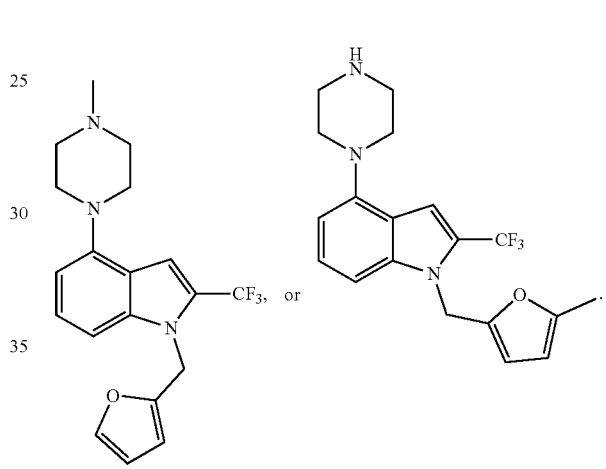

20. The pharmaceutical composition of claim 19, wherein the pharmaceutical composition comprises 0.1-1000 mg of the hydrochloride salt of

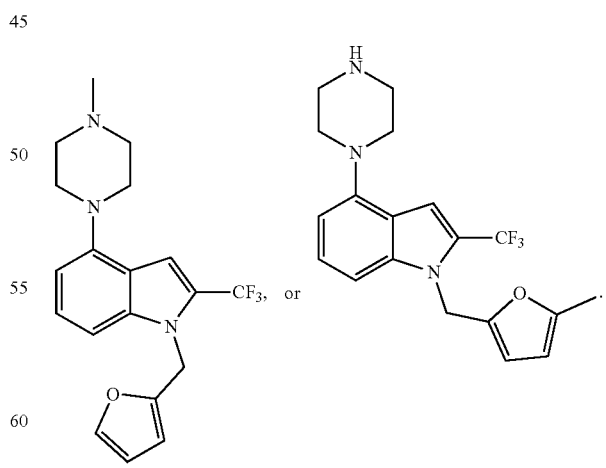

* * * * *